(12) United States Patent
Jeong et al.

(10) Patent No.: US 12,180,287 B2
(45) Date of Patent: Dec. 31, 2024

(54) ANTI-C-MET ANTIBODY SHOWING ENHANCED STABILITY OR ANTIGEN-BINDING FRAGMENTS THEREOF

(71) Applicant: HELIXMITH CO., LTD, Seoul (KR)

(72) Inventors: Jae-Gyun Jeong, Seoul (KR); Junghun Lee, Seoul (KR); Sang Ho Kwon, Seoul (KR)

(73) Assignee: HELIXMITH CO., LTD, Seoul (KR)

( * ) Notice: Subject to any disclaimer, the term of this patent is extended or adjusted under 35 U.S.C. 154(b) by 825 days.

(21) Appl. No.: 17/293,703

(22) PCT Filed: Nov. 13, 2019

(86) PCT No.: PCT/KR2019/015475
§ 371 (c)(1),
(2) Date: May 13, 2021

(87) PCT Pub. No.: WO2020/101365
PCT Pub. Date: May 22, 2020

(65) Prior Publication Data
US 2021/0403576 A1     Dec. 30, 2021

(30) Foreign Application Priority Data
Nov. 14, 2018  (KR) .................. 10-2018-0140196

(51) Int. Cl.
C07K 16/28  (2006.01)
(52) U.S. Cl.
CPC ...... *C07K 16/2863* (2013.01); *C07K 2317/24* (2013.01); *C07K 2317/52* (2013.01); *C07K 2317/565* (2013.01); *C07K 2317/567* (2013.01); *C07K 2317/70* (2013.01); *C07K 2317/92* (2013.01); *C07K 2317/94* (2013.01)
(58) Field of Classification Search
CPC ............ C07K 16/2863; C07K 2317/24; C07K 2317/52; C07K 2317/565; C07K 2317/567; C07K 2317/70; C07K 2317/92; C07K 2317/94
See application file for complete search history.

(56) References Cited

U.S. PATENT DOCUMENTS

| | | |
|---|---|---|
| 9,090,694 B2 | 7/2015 | Duffy et al. |
| 9,212,227 B2 | 12/2015 | Duffy et al. |
| 9,631,020 B2 | 4/2017 | Park et al. |
| 9,951,137 B2 | 4/2018 | Duffy et al. |
| 10,106,622 B2 | 10/2018 | Yoo et al. |
| 10,221,249 B2 | 3/2019 | States et al. |
| 10,450,377 B2 | 10/2019 | Duffy et al. |
| 10,927,177 B2 | 2/2021 | Yu et al. |
| 11,352,426 B2 | 6/2022 | Tan et al. |
| 2011/0239316 A1 | 9/2011 | Goetsch et al. |
| 2013/0287777 A1 | 10/2013 | Duffy et al. |
| 2013/0336980 A1 | 12/2013 | Duffy et al. |
| 2014/0193431 A1 | 7/2014 | Park et al. |
| 2017/0066831 A1 | 3/2017 | Duffy et al. |
| 2017/0073432 A1 | 3/2017 | States et al. |
| 2017/0233492 A1 | 8/2017 | Yoo et al. |
| 2017/0348429 A1 | 12/2017 | Reilly et al. |
| 2018/0273622 A1 | 9/2018 | Tan et al. |
| 2019/0062439 A1 | 2/2019 | Duffy et al. |
| 2019/0292275 A1 | 9/2019 | States et al. |
| 2019/0315872 A1 | 10/2019 | Yu et al. |
| 2019/0330354 A1 | 10/2019 | Coronella et al. |

FOREIGN PATENT DOCUMENTS

| | | |
|---|---|---|
| CN | 108601834 A | 9/2018 |
| JP | 2015-516817 A | 6/2015 |
| JP | 2018-501297 A | 1/2018 |
| JP | 2018-526034 A | 9/2018 |
| JP | 2018-531000 A | 10/2018 |
| KR | 10-2012-0134938 A | 12/2012 |
| KR | 10-2016-0017918 A | 2/2016 |
| WO | WO-2016/021864 A1 | 2/2016 |
| WO | WO-2017/135791 A1 | 8/2017 |
| WO | WO-2018/062402 A1 | 4/2018 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi. 1996.0548).*
Casset et al (2003) Biochemical and Biophysical Research Communications, 307:198-205. (doi: 10.1016/S0006-291X(03)01131-8).*
Chen et al. (1995) EMBO J., 14(12):2784-2794. (doi: 10.1002/j.1460-2075.1995.tb07278.x).*
International Search Report from corresponding PCT Application No. PCT/KR2019/015475, dated Mar. 16, 2020.

(Continued)

*Primary Examiner* — Robert S Landsman
(74) *Attorney, Agent, or Firm* — Harness, Dickey & Pierce, P.L.C.

(57) ABSTRACT

The present invention relates to an anti-c-Met antibody showing enhanced stability or antigen-binding fragments thereof, and the use thereof. Compared to 1E4 which is a parent antibody, the anti-c-Met antibody showing enhanced stability or antigen-binding reduced immunogenicity. Therefore, the anti-c-Met antibody or antigen-binding fragments thereof according to the present invention exhibits, in anti-c-Met antibody development, excellent properties such as reduced production cost, inhibition of reduced efficacy, reduced side effects and the like.

5 Claims, 28 Drawing Sheets

Specification includes a Sequence Listing.

(56) References Cited

OTHER PUBLICATIONS

Yaghoub Safdari, Safar Farajnia, Mohammad Asgharzadeh & Masoumeh Khalili (2013) Antibody humanization methods—a review and update, Biotechnology and Genetic Engineering Reviews, 29:2, 175-186, DOI: 10.1080/02648725.2013.801235.

Han, C., et al.; "c-Met signaling pathway and related inhibitors: research progress", J Int Pharm Res., vol. 45, No. 2, 2018, pp. 94-101.

Lu. R. M., et al.; "Single chain anti-c-Met antibody conjugated nanoparticles for in vivo tumor-targeted imaging and drug delivery", Biomaterials 32 (2011) 3265-3274.

Office Action from corresponding Chinese Patent Application No. 201980075213.1, dated Mar. 28, 2023.

Office Action from corresponding Japanese Patent Application No. 2021-526711, dated Jun. 15, 2022.

Grant of Patent from corresponding Korean Patent Application No. 10-2018-0140196, dated Nov. 11, 2021.

\* cited by examiner

FIG. 2h

Heavy Chain

```
                            10                  20                  30                  40              50  52 A
VH_(VH0)(SEQ ID No: 11)    QVQLVQSGAEVKKPGESLRI SCQGSGYSFPTHWM TWRQMPGKGLEWMGTI DPTDSYNFY

IgHv5-51-01 Germline       EVQLVQSGAEVKKPGESLRI SCKGSGYSFTSYW  VRQMPGKGLEWMGII YPGDSDTRY
VH2(SEQ ID No: 12)         EVQLVQSGAEVKKPGESLRI SCKGSGYSFTSYW  TWRQMPGKGLEWMGTI DPTDSYNFY
                                                               (SEQ ID No: 1)

IgHv1-69-02 Germline       QVQLVQSGAEVKKPGSSVKVSCKASGGTFSSYT  SWRQAPGQGLEWMGRI EPILGIANY
VH3(SEQ ID No: 13)         YQLVQSGAEVKKPGSSVKVSCQGSGYSFPTHWM TWRQAPGQGLEWMGTI DPTDSYNFY
VH4(SEQ ID No: 14)         YQLVQSGAEVKKPGSSVKVSCQGSGYSFPTHWM TWRQAPGQGLEWMGTI DPTDSYNFY
VH5(SEQ ID No: 15)         YQLVQSGAEVKKPGSSVKVSCQGSGYSFPTHWM TWRQAPGQGLEWMGTI DPTDSYNFY
VH6(SEQ ID No: 16)         YQLVQSGAEVKKPGSSVKVSCKASGYSFPTHWM TWRQAPGQGLEWMGTI DPTDSYNFY
                                                                                (SEQ ID No: 2)
```

FIG. 3a

Heavy Chain

| | 60 | 70 | 80 82A B C | 90 | 100 A B C D E F G H I |
|---|---|---|---|---|---|
| VH_(VH0)(SEQ ID No: 11) | GPSFQGHVTI | SADSSSSTAYL | QWSSLKASDTAMYY | CARDGNYYDSRGYYYDTFDMWGQGT | |
| IgHV5-51-01 Germline VH2(SEQ ID No: 12) | SPSFQGQVTI | SADKSISTAYL | QWSSLKASDTAMYY | CAR | |
| IgHV1-69-02 Germline VH3(SEQ ID No: 13) | GPSFQGQVTI | SADKSLSTAYL | QWSSLKASDTAMYY | CAR | |
| VH3(SEQ ID No: 13) | AQKFQGRVTI | TADKSTSTAYM | ELSSLRSEDTAMYY | CARDGNYYDSRGYYYDTFDMWGQGT | |
| VH4(SEQ ID No: 14) | GPSFQGRVTI | TADSSTSTAYL | QWSSLRSEDTAMYY | CARDGNYYDSRGYYYDTFDMWGQGT | |
| VH5(SEQ ID No: 15) | GPSFQGRVTI | TADSSTSTAYM | ELSSLRSEDTAMYY | CARDGNYYDSRGYYYDTFDMWGQGT | |
| VH6(SEQ ID No: 16) | GPSFQGRVTI | TADKSTSTAYM | ELSSLRSEDTAMYY | CARDGNYYDSRGYYYDTFDMWGQGT | |
| | GPSFQGRVTI | TADKSTSTAYM | ELSSLRSEDTAMYY | CARDGNYYDSRGYYYDTFDMWGQGT (SEQ ID No: 3) | |

FIG. 3b

Heavy Chain

|  | 110 | 113 |
|---|---|---|
| VH_(VH0)(SEQ ID No: 11) | L V T V S S | |

IgHV5-51-01 Germline

| VH2(SEQ ID No: 12) | L V T V S S |

IgHV1-69-02 Germline

| VH3(SEQ ID No: 13) | L V T V S S |
| VH4(SEQ ID No: 14) | L V T V S S |
| VH5(SEQ ID No: 15) | L V T V S S |
| VH6(SEQ ID No: 16) | L V T V S S |

FIG. 3c

Light Chain

```
                                    10                    20                    30                    40                    50                    60
VK_(VK0)(SEQ ID No: 17)    DI QMTQSPSFLSASVGDRVTI TCRASQGI STYLAWYQQKPGTAPKLLI YSASTLESGVPS
IgKV1-39-01 Germline
VK2(SEQ ID No: 18)         DI QMTQSPSSLSASVGDRVTI TCRASQSI SSYLNWYQQKPGKAPKLLI YAASSLQSGVPS
                           DI QMTQSPSSLSASVGDRVTI TCRASQGI STYLAWYQQKPGKAPKLLI YSASTLESGVPS
IgKV2-28-01 Germline       EI VMTQSPGTLSLSPGERATLSCRASQSVSSSYLAWYQQKPGQAPRLLI YGASSRATGIPD
VK3(SEQ ID No: 19)         DI QMTQSPGTLSLSPGERATLSCRASQGI STYLAWYQQKPGQAPRLLI YSASTLESGVPD
VK4(SEQ ID No: 20)         DI QMTQSPGTLSLSPGERATLSCRASQGI STYLAWYQQKPGQAPRLLI YSASTLESGVPD
VK5(SEQ ID No: 21)         EI VMTQSPGTLSLSPGERATLSCRASQGI STYLAWYQQKPGQAPRLLI YSASTLESGVPD
                                                    (SEQ ID No: 4)                              (SEQ ID No: 5)
```

FIG. 3d

Light Chain

```
                                        70               80              90            100      106 A
VK_(VK0)(SEQ ID No: 17)     RF SGSGSGTDFTLTI SSLQPEDSATYYCQQADSFPLTFGGGTKVEIK

IgKV1-39-01 Germline
VK2(SEQ ID No: 18)          RF SGSGSGTDFTLTI SSLQPEDFATYYCQQSYSTP
                            RF SGSGSGTDFTLTI SSLQPEDFATYYCQQADSFPLTFGGGTKVEIK IgKV3-20-01 Germline
VK3(SEQ ID No: 19)          RF SGSGSGTDFTLTI SRLEPEDFAVYYCQQYGSSP
VK4(SEQ ID No: 20)          RF SGSGSGTDFTLTI SRLEPEDFATYYCQQADSFPLTFGGGTKVEIK
VK5(SEQ ID No: 21)          RF SGSGSGTDFTLTI SRLEPEDFATYYCQQADSFPLTFGGGTKVEIK
                            RF SGSGSGTDFTLTI SRLEPEDFATYYCQQADSFPLTFGGGTKVEIK
                                                                  (SEQ ID No: 6)
```

FIG. 3e

Light Chain

```
                              70                  80                   90              100      106 A
VK_(VK0)(SEQ ID No: 17)   RFSGSGSGTDFTLTISSLQPEDSATYYCQQSATQPEDSFPLTFGGGTKVEIK

IgKV1-39-01 Germline
VK2(SEQ ID No: 18)        RFSGSGSGTDFTLTISSLQPEDFATYYCQQSYSTP
                          RFSGSGSGTDFTLTISSLQPEDFATYYCQQADSFPLTFGGGTKVEIK IgKV3-20-01 Germline
VK3(SEQ ID No: 19)        RFSGSGSGTDFTLTISRLEPEDFAVYYCQQYGSSP
VK4(SEQ ID No: 20)        RFSGSGSGTDFTLTISRLEPEDFATYYCQQADSFPLTFGGGTKVEIK
VK5(SEQ ID No: 21)        RFSGSGSGTDFTLTISRLEPEDFATYYCQQADSFPLTFGGGTKVEIK
                          RFSGSGSGTDFTLTISRLEPEDFATYYCQQADSFPLTFGGGTKVEIK
                                                                    (SEQ ID No: 6)
```

FIG. 7a

```
                                    190              200              210              220              230              240
                                    |                |                |                |                |                |
(SEQ ID No: 7)  1E4 C Domain        STYRVVSVLTVLHQDWLNGKEYKCKVSNKALPAPIEKTISKAKGQPREPQVYTLPPSREE
(SEQ ID No: 9)  G1m(3) Allotype     STYRVVSVLTVLHQDWLNGKEYKCKVSNKALPAPIEKTISKAKGQPREPQVYTLPPSREE
                G1m(17,1) Allotype  STYRVVSVLTVLHQDWLNGKEYKCKVSNKALPAPIEKTISKAKGQPREPQVYTLPPSRDE
                                                                                                                        *

250              260              270              280              290              300
                                    |                |                |                |                |                |
(SEQ ID No: 7)  1E4 C Domain        MTKNQVSLTCLVKGFYPSDIAVEWESNGQPENNYKTTPPVLDSDGSFFLYSKLTVDKSRW
(SEQ ID No: 9)  G1m(3) Allotype     MTKNQVSLTCLVKGFYPSDIAVEWESNGQPENNYKTTPPVLDSDGSFFLYSKLTVDKSRW
                G1m(17,1) Allotype  LTKNQVSLTCLVKGFYPSDIAVEWESNGQPENNYKTTPPVLDSDGSFFLYSKLTVDKSRW
                                    *

310              320              330
                                    |                |                |
(SEQ ID No: 7)  1E4 C Domain        QQGNVFSCSVMHEALHNHYTQKSLSLSPGK
(SEQ ID No: 9)  G1m(3) Allotype     QQGNVFSCSVMHEALHNHYTQKSLSLSPGK
                G1m(17,1) Allotype  QQGNVFSCSVMHEALHNHYTQKSLSLSPGK
```

\* Indicated difference from 1E4 sequence

FIG. 7b (SEQ ID No: 8) 1E4 Kappa Domain SVAAPSVFIFPPSDEQLKSGTASVVCLLNNFYPREAKVQWKVDNALQSGNSQESVTEQDS
(SEQ ID No: 10) Km3 Allotype       TVAAPSVFIFPPSDEQLKSGTASVVCLLNNFYPREAKVQWKVDNALQSGNSQESVTEQDS
                                    *

(SEQ ID No: 8) 1E4 Kappa Domain KDSTYSLSSTLTLSKADYEKHKVYACEVTHQGLSSPVTKSFNRGEC
(SEQ ID No: 10) Km3 Allotype       KDSTYSLSSTLTLSKADYEKHKVYACEVTHQGLSSPVTKSFNRGEC \* Indicated difference from 1E4 sequence

FIG. 7c

SEQUENCE LISTING

```
<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: CDRH1 of anti c-Met Antibody 1E4

<400> SEQUENCE: 1

Thr His Trp Ile Thr
1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2 of anti c-Met Antibody 1E4

<400> SEQUENCE: 2

Thr Ile Asp Pro Thr Asp Ser Tyr Asn Phe Tyr Gly Pro Ser Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: CDRH3 of anti c-Met Antibody 1E4

<400> SEQUENCE: 3

Asp Gly Asn Tyr Tyr Asp Ser Arg Gly Tyr Tyr Tyr Asp Thr Phe Asp
1               5                   10                  15

Met

<210> SEQ ID NO 4
<211> LENGTH: 11
<212> TYPE: PRT
<213> ORGANISM: Artificial Sequence
<220> FEATURE:
<223> OTHER INFORMATION: CDRL1 of anti c-Met Antibody 1E4
```

```
<400> SEQUENCE: 4

Arg Ala Ser Gln Gly Ile Ser Thr Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDRL2 of anti c-Met Antibody 1E4

<400> SEQUENCE: 5

Ser Ala Ser Thr Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3 of anti c-Met Antibody 1E4

<400> SEQUENCE: 6

Gln Gln Ala Asp Ser Phe Pro Leu Thr
1               5

<210> SEQ ID NO 7
<211> LENGTH: 98
<212> TYPE: PRT
<213> ORGANISM: Artificial Sequence
<220> FEATURE:
<223> OTHER INFORMATION: Constant domain 1 of heavy chain (CH1) of anti
      c-Met Antibody 1E4(VH)

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 8
<211> LENGTH: 107
<212> TYPE: PRT
<213> ORGANISM: Artificial Sequence
<220> FEATURE:
<223> OTHER INFORMATION: Kappa-constant domain (Ck) of anti c-Met
      Antibody 1E4(Ck)

<400> SEQUENCE: 8

Arg Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 9
<211> LENGTH: 98
<212> TYPE: PRT
<213> ORGANISM: Artificial Sequence
<220> FEATURE:
<223> OTHER INFORMATION: Variant CH1 of anti c-Met Antibody 1E4(VH0)

<400> SEQUENCE: 9

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val

<210> SEQ ID NO 10
<211> LENGTH: 107
<212> TYPE: PRT
<213> ORGANISM: Artificial Sequence
<220> FEATURE:
<223> OTHER INFORMATION: Variant Kappa constant domain of anti c-Met
      Antibody 1E4(Ck0)

<400> SEQUENCE: 10

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 11

```
<211> LENGTH: 126
<212> TYPE: PRT
<213> ORGANISM: Artificial Sequence
<220> FEATURE:
<223> OTHER INFORMATION: Heavy chain variable of 1E4 (VH or VH0)

<400> SEQUENCE: 11

Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser
        115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Variant Heavy chain variable of 1E4 (VH2)

<400> SEQUENCE: 12

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser
        115                 120                 125

<210> SEQ ID NO 13
<211> LENGTH: 126
<212> TYPE: PRT
<213> ORGANISM: Artificial Sequence
<220> FEATURE:
<223> OTHER INFORMATION: Variant Heavy chain variable of 1E4 (VH3)

<400> SEQUENCE: 13

Gln Val Gln Leu Val Gln Ser Gly Ala Glu Val Lys Lys Pro Gly Ser
1               5                   10                  15
```

Ser Val Lys Val Ser Cys Gln Gly Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Ser Ser Thr Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Tyr Asp Thr
                100                 105                 110

Phe Asp Met Trp Gly Gln Gly Thr Leu Val Thr Val Ser Ser
            115                 120                 125

<210> SEQ ID NO 14
<211> LENGTH: 126
<212> TYPE: PRT
<213> ORGANISM: Artificial Sequence
<220> FEATURE:
<223> OTHER INFORMATION: Variant Heavy chain variable of 1E4 (VH4)

<400> SEQUENCE: 14

Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Ser Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Asp Gly Asn Tyr Tyr Asp Ser Arg Gly Tyr Tyr Tyr Asp Thr
                100                 105                 110

Phe Asp Met Trp Gly Gln Gly Thr Leu Val Thr Val Ser Ser
            115                 120                 125

<210> SEQ ID NO 15
<211> LENGTH: 126
<212> TYPE: PRT
<213> ORGANISM: Artificial Sequence
<220> FEATURE:
<223> OTHER INFORMATION: Variant Heavy chain variable of 1E4 (VH5)

<400> SEQUENCE: 15

Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Ser Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser
        115                 120                 125

<210> SEQ ID NO 16
<211> LENGTH: 126
<212> TYPE: PRT
<213> ORGANISM: Artificial Sequence
<220> FEATURE:
<223> OTHER INFORMATION: Variant Heavy chain variable of 1E4 (VH6)

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser
        115                 120                 125

<210> SEQ ID NO 17
<211> LENGTH: 107
<212> TYPE: PRT
<213> ORGANISM: Artificial Sequence
<220> FEATURE:
<223> OTHER INFORMATION: Kappa chain variable of 1E4 (Vk or Vk0)

<400> SEQUENCE: 17

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Thr Ala Pro Lys Leu Leu Ile
        35                  40                  45

Tyr Ser Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asp Ser Phe Pro Leu
                85                  90                  95

Thr Phe Gly Gly Gly Thr Lys Val Glu Ile Lys
            100                 105

<210> SEQ ID NO 18
<211> LENGTH: 107
<212> TYPE: PRT

```
<213> ORGANISM: Artificial Sequence
<220> FEATURE:
<223> OTHER INFORMATION: Variant Kappa chain variable of 1E4 (Vk2)

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Lys Leu Leu Ile
        35                  40                  45

Tyr Ser Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Variant Kappa chain variable of 1E4 (Vk3)

<400> SEQUENCE: 19

Asp Ile Gln Met Thr Gln Ser Pro Gly Phe Leu Ser Leu Ser Pro Gly
1               5                   10                  15

Glu Arg Ala Thr Leu Ser Cys Arg Ala Ser Gln Gly Ile Ser Thr Tyr
            20                  25                  30

Leu Ala Trp Tyr Gln Gln Lys Pro Gly Gln Ala Pro Arg Leu Leu Ile
        35                  40                  45

Tyr Ser Ala Ser Thr Leu Glu Ser Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Variant Kappa chain variable of 1E4 (Vk4)

<400> SEQUENCE: 20

Glu Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Thr Tyr
            20                  25                  30

Leu Ala Trp Tyr Gln Gln Lys Pro Gly Gln Ala Pro Arg Leu Leu Ile
        35                  40                  45

Tyr Ser Ala Ser Thr Leu Glu Ser Gly Val Pro Asp Arg Phe Ser Gly
    50                  55                  60
```

```
Ser Gly Ser Gly Thr Asp Phe Thr Leu Thr Ile Ser Arg Leu Glu Pro
 65                  70                  75                  80

Glu Asp Phe Ala Thr Tyr Tyr Cys Gln Gln Ala Asp Ser Phe Pro Leu
                 85                  90                  95

Thr Phe Gly Gly Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Variant Kappa chain variable of 1E4 (Vk5)

<400> SEQUENCE: 21

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gly Ile Ser Thr Tyr
                20                  25                  30

Leu Ala Trp Tyr Gln Gln Lys Pro Gly Gln Ala Pro Arg Leu Leu Ile
            35                  40                  45

Tyr Ser Ala Ser Thr Leu Glu Ser Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Thr Tyr Tyr Cys Gln Gln Ala Asp Ser Phe Pro Leu
                 85                  90                  95

Thr Phe Gly Gly Gly Thr Lys Val Glu Ile Lys
            100                 105

<210> SEQ ID NO 22
<211> LENGTH: 378
<212> TYPE: DNA
<213> ORGANISM: Artificial Sequence
<220> FEATURE:
<223> OTHER INFORMATION: Heavy chain variable of 1E4 (VH or VH0)

<400> SEQUENCE: 22
caggtgcagc tggtgcagtc tggcgccgaa gtgaagaagc ccggcgaatc cctgcggatc      60
tcctgccagg gctccggcta ctccttcccc acccactgga tcacctgggt gcgacagatg     120
cccggcaagg gcctggaatg gatgggcacc atcgacccca ccgactccta caacttctac     180
ggccccagct tccagggcca cgtgaccatc tccgccgact cctccagctc caccgcctac     240
ctgcagtggt cctccctgaa ggcctccgac accgccatgt actactgcgc cagggacggc     300
aactactacg actcccgggg ctactactac gataccttcg acatgtgggg ccagggcacc     360
ctggtcaccg tctcctca                                                   378

<210> SEQ ID NO 23
<211> LENGTH: 378
<212> TYPE: DNA
<213> ORGANISM: Artificial Sequence
<220> FEATURE:
<223> OTHER INFORMATION: Variant Heavy chain variable of 1E4 (VH2)

<400> SEQUENCE: 23
gaggtgcagc tggtgcagtc tggcgccgaa gtgaagaagc ccggcgaatc cctgaagatc      60
tcctgcaagg gctccggcta ctccttcccc acccactgga tcacctgggt gcgacagatg     120
```

```
cccggcaagg gcctggaatg gatgggcacc atcgacccca ccgactccta caacttctac    180
ggccccagct tccagggcca agtgaccatc tccgccgaca agtccatctc caccgcctac    240
ctgcagtggt cctccctgaa ggcctccgac accgccatgt actactgcgc cagggacggc    300
aactactacg actcccgggg ctactactac gataccttcg acatgtgggg ccagggcacc    360
ctggtcaccg tctcctca                                                 378

<210> SEQ ID NO 24
<211> LENGTH: 378
<212> TYPE: DNA
<213> ORGANISM: Artificial Sequence
<220> FEATURE:
<223> OTHER INFORMATION: Variant Heavy chain variable of 1E4 (VH3)

<400> SEQUENCE: 24
caggtgcagc tggtgcagtc tggcgccgaa gtgaagaagc ccggctcctc cgtgaaggtc     60
tcctgccagg gctccggcta ctccttcccc acccactgga tcacctgggt gcgacaggcc    120
cccggccaag gcctggaatg gatgggcacc atcgacccca ccgactccta caacttctac    180
ggccccagct tccagggcag agtgaccatc accgccgact cctccacgtc caccgcctac    240
ctgcagtggt cctccctgaa ggcctccgac accgccatgt actactgcgc cagggacggc    300
aactactacg actcccgggg ctactactac gataccttcg acatgtgggg ccagggcacc    360
ctggtcaccg tctcctca                                                 378

<210> SEQ ID NO 25
<211> LENGTH: 378
<212> TYPE: DNA
<213> ORGANISM: Artificial Sequence
<220> FEATURE:
<223> OTHER INFORMATION: Variant Heavy chain variable of 1E4 (VH4)

<400> SEQUENCE: 25
caggtgcagc tggtgcagtc tggcgccgaa gtgaagaagc ccggctcctc cgtgaaggtc     60
tcctgccagg gctccggcta ctccttcccc acccactgga tcacctgggt gcgacaggcc    120
cccggccaag gcctggaatg gatgggcacc atcgacccca ccgactccta caacttctac    180
ggccccagct tccagggcag agtgaccatc accgccgact cctccacgtc caccgcctac    240
atggagctgt cctccctgag atctgaggac accgccatgt actactgcgc cagggacggc    300
aactactacg actcccgggg ctactactac gataccttcg acatgtgggg ccagggcacc    360
ctggtcaccg tctcctca                                                 378

<210> SEQ ID NO 26
<211> LENGTH: 378
<212> TYPE: DNA
<213> ORGANISM: Artificial Sequence
<220> FEATURE:
<223> OTHER INFORMATION: Variant Heavy chain variable of 1E4 (VH5)

<400> SEQUENCE: 26
caggtgcagc tggtgcagtc tggcgccgaa gtgaagaagc ccggctcctc cgtgaaggtc     60
tcctgccagg gctccggcta ctccttcccc acccactgga tcacctgggt gcgacaggcc    120
cccggccaag gcctggaatg gatgggcacc atcgacccca ccgactccta caacttctac    180
ggccccagct tccagggcag agtgaccatc accgccgact cctccacgtc caccgcctac    240
atggagctgt cctccctgag atctgaggac accgccgtgt actactgcgc cagggacggc    300
aactactacg actcccgggg ctactactac gataccttcg acatgtgggg ccagggcacc    360
```
ctggtcaccg tctcctca                                                  378

<210> SEQ ID NO 27
<211> LENGTH: 378
<212> TYPE: DNA
<213> ORGANISM: Artificial Sequence
<220> FEATURE:
<223> OTHER INFORMATION: Variant Heavy chain variable of 1E4 (VH6)

<400> SEQUENCE: 27
caggtgcagc tggtgcagtc tggcgccgaa gtgaagaagc ccggctcctc cgtgaaggtc    60
tcctgcaagg cttccggcta ctccttcccc acccactgga tcacctgggt gcgacaggcc   120
cccggccaag gcctggaatg gatgggcacc atcgacccca ccgactccta caacttctac   180
ggccccagct tccagggcag agtgaccatc accgccgaca gtccacgtc caccgcctac    240 atggagctgt cctccctgag atctgaggac accgccgtgt actactgcgc cagggacggc   300
aactactacg actcccgggg ctactactac gataccttcg acatgtgggg ccagggcacc   360
ctggtcaccg tctcctca                                                  378

<210> SEQ ID NO 28
<211> LENGTH: 321
<212> TYPE: DNA
<213> ORGANISM: Artificial Sequence
<220> FEATURE:
<223> OTHER INFORMATION: Kappa chain variable of 1E4 (Vk or Vk0)

<400> SEQUENCE: 28
gacatccaga tgacccagtc ccccagcttc ctgtccgcct ccgtgggcga cagagtgacc    60
atcacctgtc gggcctccca gggcatctcc acctacctgg cctggtatca gcagaagccc   120
ggcaccgccc ccaagctgct gatctactcc gcctccaccc tggaatccgg cgtgccctcc   180
agattctccg gctccggctc tggcaccgac ttcaccctga ccatctccag cctgcagccc   240
gaggactccg ccacctacta ctgccagcag gccgactcct tcccccctgac cttcggcgga   300 ggcaccaagg tggaaatcaa a                                              321

<210> SEQ ID NO 29
<211> LENGTH: 321
<212> TYPE: DNA
<213> ORGANISM: Artificial Sequence
<220> FEATURE:
<223> OTHER INFORMATION: Variant Kappa chain variable of 1E4 (Vk2)

<400> SEQUENCE: 29
gacatccaga tgacccagtc ccccagctcc ctgtccgcct ccgtgggcga cagagtgacc    60
atcacctgtc gggcctccca gggcatctcc acctacctgg cctggtatca gcagaagccc   120
ggcaaagccc ccaagctgct gatctactcc gcctccaccc tggaatccgg cgtgccctcc   180
agattctccg gctccggctc tggcaccgac ttcaccctga ccatctccag cctgcagccc   240
gaggactttg ccacctacta ctgccagcag gccgactcct tcccccctgac cttcggcgga   300 ggcaccaagg tggaaatcaa a                                              321

<210> SEQ ID NO 30
<211> LENGTH: 321
<212> TYPE: DNA
<213> ORGANISM: Artificial Sequence
<220> FEATURE:
<223> OTHER INFORMATION: Variant Kappa chain variable of 1E4 (Vk3)

<400> SEQUENCE: 30

```
gacatccaga tgacccagtc ccccggcttc ctgtccttgt ccccaggcga aagagccacc    60
ctctcctgtc gggcctccca gggcatctcc acctacctgg cctggtatca gcagaagccc   120
ggccaggccc ccaggctgct gatctactcc gcctccaccc tggaatccgg cgtgcccgac   180
agattctccg gctccggctc tggcaccgac ttcaccctga ccatctccag actggagccc   240
gaggactttg ccacctacta ctgccagcag gccgactcct tcccccctga cttcggcgga   300
ggcaccaagg tggaaatcaa a                                             321
```

<210> SEQ ID NO 31
<211> LENGTH: 321
<212> TYPE: DNA
<213> ORGANISM: Artificial Sequence
<220> FEATURE:
<223> OTHER INFORMATION: Variant Kappa chain variable of 1E4 (Vk4)

<400> SEQUENCE: 31

```
gaaatccaga tgacccagtc ccccggcacc ctgtccttgt ccccaggcga aagagccacc    60
ctctcctgtc gggcctccca gggcatctcc acctacctgg cctggtatca gcagaagccc   120
ggccaggccc ccaggctgct gatctactcc gcctccaccc tggaatccgg cgtgcccgac   180
agattctccg gctccggctc tggcaccgac ttcaccctga ccatctccag actggagccc   240
gaggactttg ccacctacta ctgccagcag gccgactcct tcccccctga cttcggcgga   300
ggcaccaagg tggaaatcaa a                                             321
```

<210> SEQ ID NO 32
<211> LENGTH: 321
<212> TYPE: DNA
<213> ORGANISM: Artificial Sequence
<220> FEATURE:
<223> OTHER INFORMATION: Variant Kappa chain variable of 1E4 (Vk5)

<400> SEQUENCE: 32

```
gaaatcgtgt tgacccagtc ccccggcacc ctgtccttgt ccccaggcga aagagccacc    60
ctctcctgtc gggcctccca gggcatctcc acctacctgg cctggtatca gcagaagccc   120
ggccaggccc ccaggctgct gatctactcc gcctccaccc tggaatccgg catccccgac   180
agattctccg gctccggctc tggcaccgac ttcaccctga ccatctccag actggagccc   240
gaggactttg ccacctacta ctgccagcag gccgactcct tcccccctga cttcggcgga   300
ggcaccaagg tggaaatcaa a                                             321
```

<210> SEQ ID NO 33
<211> LENGTH: 456
<212> TYPE: PRT
<213> ORGANISM: Artificial Sequence
<220> FEATURE:
<223> OTHER INFORMATION: Heavy chain of 1E4(VH)

<400> SEQUENCE: 33

```
Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60
```

Gln Gly His Val Thr Ile Ser Ala Asp Ser Ser Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 34
<211> LENGTH: 456

<212> TYPE: PRT
<213> ORGANISM: Artificial Sequence
<220> FEATURE:
<223> OTHER INFORMATION: Heavy chain of 1E4 variant (VH0)

<400> SEQUENCE: 34

```
Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Asp Thr
            100                 105                 110

Phe Asp Met Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380
```

-continued

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 35
<211> LENGTH: 456
<212> TYPE: PRT
<213> ORGANISM: Artificial Sequence
<220> FEATURE:
<223> OTHER INFORMATION: Heavy chain of 1E4 variant (VH2)

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285
```

```
Asp Gly Val Glu Val His Asn Ala Lys Thr Lys Pro Arg Glu Glu Gln
    290                 295                 300

Tyr Asn Ser Thr Tyr Arg Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 36
<211> LENGTH: 456
<212> TYPE: PRT
<213> ORGANISM: Artificial Sequence
<220> FEATURE:
<223> OTHER INFORMATION: Heavy chain of 1E4 variant (VH3)

<400> SEQUENCE: 36

Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
                20                  25                  30

Trp Ile Thr Trp Val Arg Gln Ala Pro Gly Gln Gly Leu Glu Trp Met
            35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Ser Ser Thr Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190
```

```
Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 37
<211> LENGTH: 456
<212> TYPE: PRT
<213> ORGANISM: Artificial Sequence
<220> FEATURE:
<223> OTHER INFORMATION: Heavy chain of 1E4 variant (VH4)

<400> SEQUENCE: 37

Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
                20                  25                  30

Trp Ile Thr Trp Val Arg Gln Ala Pro Gly Gln Gly Leu Glu Trp Met
            35                  40                  45

Gly Thr Ile Asp Pro Thr Asp Ser Tyr Asn Phe Tyr Gly Pro Ser Phe
        50                  55                  60

Gln Gly Arg Val Thr Ile Thr Ala Asp Ser Ser Thr Ser Thr Ala Tyr
65                  70                  75                  80

Met Glu Leu Ser Ser Leu Arg Ser Glu Asp Thr Ala Met Tyr Tyr Cys
                85                  90                  95
```

```
Ala Arg Asp Gly Asn Tyr Tyr Asp Ser Arg Gly Tyr Tyr Asp Thr
            100                 105                 110

Phe Asp Met Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
450                 455
```

<210> SEQ ID NO 38
<211> LENGTH: 456
<212> TYPE: PRT
<213> ORGANISM: Artificial Sequence
<220> FEATURE:
<223> OTHER INFORMATION: Heavy chain of 1E4 variant (VH5)

<400> SEQUENCE: 38

```
Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
            20                  25                  30

Trp Ile Thr Trp Val Arg Gln Ala Pro Gly Gln Gly Leu Glu Trp Met
            35                  40                  45

Gly Thr Ile Asp Pro Thr Asp Ser Tyr Asn Phe Tyr Gly Pro Ser Phe
50                  55                  60

Gln Gly Arg Val Thr Ile Thr Ala Asp Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Arg Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
```

-continued

```
                420                 425                 430
Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 39
<211> LENGTH: 456
<212> TYPE: PRT
<213> ORGANISM: Artificial Sequence
<220> FEATURE:
<223> OTHER INFORMATION: Heavy chain of 1E4 variant (VH6)

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
```

```
                    325                 330                 335
Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 40
<211> LENGTH: 214
<212> TYPE: PRT
<213> ORGANISM: Artificial Sequence
<220> FEATURE:
<223> OTHER INFORMATION: Light chain of 1E4 (Vk)

<400> SEQUENCE: 40

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Thr Ala Pro Lys Leu Leu Ile
        35                  40                  45

Tyr Ser Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asp Ser Phe Pro Leu
                85                  90                  95

Thr Phe Gly Gly Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 41
<211> LENGTH: 214
<212> TYPE: PRT
<213> ORGANISM: Artificial Sequence
<220> FEATURE:
<223> OTHER INFORMATION: Light chain of 1E4 variant (Vk0)

<400> SEQUENCE: 41
```

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Thr Ala Pro Lys Leu Leu Ile
        35                  40                  45

Tyr Ser Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asp Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 42
<211> LENGTH: 214
<212> TYPE: PRT
<213> ORGANISM: Artificial Sequence
<220> FEATURE:
<223> OTHER INFORMATION: Light chain of 1E4 variant (Vk2)

<400> SEQUENCE: 42
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Lys Leu Leu Ile
        35                  40                  45

Tyr Ser Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Leu
                85                  90                  95

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 43
<211> LENGTH: 214
<212> TYPE: PRT
<213> ORGANISM: Artificial Sequence
<220> FEATURE:
<223> OTHER INFORMATION: Light chain of 1E4 variant (Vk3)

<400> SEQUENCE: 43

```
Glu Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Thr Tyr
            20                  25                  30

Leu Ala Trp Tyr Gln Gln Lys Pro Gly Gln Ala Pro Arg Leu Leu Ile
        35                  40                  45

Tyr Ser Ala Ser Thr Leu Glu Ser Gly Val Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 44
<211> LENGTH: 214

```
<212> TYPE: PRT
<213> ORGANISM: Artificial Sequence
<220> FEATURE:
<223> OTHER INFORMATION: Light chain of 1E4 variant (Vk4)

<400> SEQUENCE: 44
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Thr Tyr
            20                  25                  30

Leu Ala Trp Tyr Gln Gln Lys Pro Gly Gln Ala Pro Arg Leu Leu Ile
        35                  40                  45

Tyr Ser Ala Ser Thr Leu Glu Ser Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 45
<211> LENGTH: 214
<212> TYPE: PRT
<213> ORGANISM: Artificial Sequence
<220> FEATURE:
<223> OTHER INFORMATION: Light chain of 1E4 variant (Vk5)

<400> SEQUENCE: 45
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Thr Tyr
            20                  25                  30

Leu Ala Trp Tyr Gln Gln Lys Pro Gly Gln Ala Pro Arg Leu Leu Ile
        35                  40                  45

Tyr Ser Ala Ser Thr Leu Glu Ser Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
    115                   120                   125

Thr Ala Ser Val Val Cys Leu Leu Asn Asn Phe Tyr Pro Arg Glu Ala
    130                   135                   140

Lys Val Gln Trp Lys Val Asp Asn Ala Leu Gln Ser Gly Asn Ser Gln
145                150               155                   160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
    180                 185                   190

Ala Cys Glu Val Thr His Gln Gly Leu Ser Ser Pro Val Thr Lys Ser
    195                 200               205

Phe Asn Arg Gly Glu Cys
    210

<210> SEQ ID NO 46
<211> LENGTH: 1371
<212> TYPE: DNA
<213> ORGANISM: Artificial Sequence
<220> FEATURE:
<223> OTHER INFORMATION: Heavy chain of 1E4(VH)

<400> SEQUENCE: 46

```
caggtgcagc tggtgcagtc tggcgccgaa gtgaagaagc cggcgagtc cctgcggatc      60
tcctgccagg gctccggcta ctccttcccc acccactgga tcacctgggt gcgacagatg     120
cccggcaagg gcctggaatg gatgggcacc atcgacccca ccgactccta caacttctac     180
ggccccagct ccagggcca cgtgaccatc tccgccgact cctccagctc accgcctac       240
ctgcagtggt cctccctgaa ggcctccgac accgccatgt actactgcgc cagggacggc     300
aactactacg actcccgggg ctactactac gataccttcg acatgtgggg ccagggcacc     360
ctggtgacag tgtcctctgc ctctaccaag ggccctttcg tgttcccct ggcccctcc       420
agcaagtcca cctctggcgg caccgctgcc ctgggctgcc tggtgaaaga ctacttcccc     480
gagcccgtga ccgtgtcctg gaactctggc gccctgacct ccggcgtgca caccttccct     540
gccgtgctgc agtcctccgg cctgtactcc ctgtcctccg tggtgaccgt gccctccagc     600
tctctgggca cccagaccta catctgcaac gtgaaccaca gccctccaa caccaaggtg      660
gacaagaagg tggaacccaa gtcctgcgac aagacccaca cctgtccccc ctgccctgcc    720
cctgaactgc tgggcggacc ctccgtgttc ctgttcccc caaagcccaa ggacaccctg      780
atgatctccc ggacccccga agtgacctgc gtggtggtgg acgtgtccca cgaggaccct    840
gaagtgaagt tcaattggta cgtggacggc gtggaagtgc acaacgccaa gaccaagccc    900
agagaggaac agtacaactc cacctaccgg gtggtgtctg tgctgaccgt gctgcaccag    960
gactggctga acggcaaaga gtacaagtgc aaggtctcca acaaggccct gcctgccccc   1020
atcgaaaaga ccatctccaa ggccaagggc cagccccgcg agccccaggt gtacacactg   1080
cccccctagcc gggaagagat gaccaagaac caggtgtccc tgacctgtct ggtgaaaggc   1140
ttctacccct ccgacattgc cgtggaatgg gagtccaacg ccagcccga gaacaactac    1200
aagaccaccc cccctgtgct ggactccgac ggctcattct tcctgtactc caagctgacc   1260
gtggacaagt cccggtggca gcagggcaac gtgttctcct gctccgtgat gcacgaggcc   1320
ctgcacaacc actacaccca gaagtccctg tccctgagcc ccggcaagtg a             1371
```

<210> SEQ ID NO 47
<211> LENGTH: 1371
<212> TYPE: DNA
<213> ORGANISM: Artificial Sequence
<220> FEATURE:
<223> OTHER INFORMATION: Heavy chain of 1E4 variant (VH0)

<400> SEQUENCE: 47

| | |
|---|---|
| caggtgcagc tggtgcagtc tggcgccgaa gtgaagaagc ccggcgaatc cctgcggatc | 60 |
| tcctgccagg gctccggcta ctccttcccc acccactgga tcacctgggt gcgacagatg | 120 |
| cccggcaagg gcctggaatg gatgggcacc atcgacccca ccgactccta caacttctac | 180 |
| ggccccagct ccagggcca cgtgaccatc tccgccgact cctccagctc caccgcctac | 240 |
| ctgcagtggt cctccctgaa ggcctccgac accgccatgt actactgcgc cagggacggc | 300 |
| aactactacg actcccgggg ctactactac gataccttcg acatgtgggg ccagggcacc | 360 |
| ctggtcaccg tctcctcagc ctccaccaag ggcccatcgg tcttcccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagagag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |
| gaggtcaagt tcaactggta cgtggacggc gtggaggtgc ataatgccaa gacaaagccg | 900 |
| cgggaggagc agtacaacag cacgtaccgt gtggtcagcg tcctcaccgt cctgcaccag | 960 |
| gactggctga atggcaagga gtacaagtgc aaggtctcca acaaagccct cccagccccc | 1020 |
| atcgagaaaa ccatctccaa agccaaaggt cagccccgag aaccacaggt gtacaccctg | 1080 |
| cccccatccc gggaagagat gaccaagaac caggtcagcc tgacctgcct ggtcaaaggc | 1140 |
| ttctatccca gcgacatcgc cgtggagtgg gagagcaatg ggcagccgga gaacaactac | 1200 |
| aagaccacgc ctcccgtgct ggactccgac ggctccttct tcctctatag caagctcacc | 1260 |
| gtggacaaga gcaggtggca gcaggggaac gtcttctcat gctccgtgat gcatgaggct | 1320 |
| ctgcacaacc actacacgca gaagagcctc tccctgtctc cgggtaaatg a | 1371 |

<210> SEQ ID NO 48
<211> LENGTH: 1371
<212> TYPE: DNA
<213> ORGANISM: Artificial Sequence
<220> FEATURE:
<223> OTHER INFORMATION: Heavy chain of 1E4 variant (VH2)

<400> SEQUENCE: 48

| | |
|---|---|
| gaggtgcagc tggtgcagtc tggcgccgaa gtgaagaagc ccggcgaatc cctgaagatc | 60 |
| tcctgcaagg gctccggcta ctccttcccc acccactgga tcacctgggt gcgacagatg | 120 |
| cccggcaagg gcctggaatg gatgggcacc atcgacccca ccgactccta caacttctac | 180 |
| ggccccagct ccagggcca agtgaccatc tccgccgaca gtccatctc caccgcctac | 240 |
| ctgcagtggt cctccctgaa ggcctccgac accgccatgt actactgcgc cagggacggc | 300 |
| aactactacg actcccgggg ctactactac gataccttcg acatgtgggg ccagggcacc | 360 |
| ctggtcaccg tctcctcagc ctccaccaag ggcccatcgg tcttcccccct ggcaccctcc | 420 |

```
tccaagagca cctctggggg cacagcggcc ctgggctgcc tggtcaagga ctacttcccc      480
gaaccggtga cggtgtcgtg gaactcaggc gccctgacca gcggcgtgca ccttcccg        540 gctgtcctac agtcctcagg actctactcc ctcagcagcg tggtgaccgt gccctccagc      600
agcttgggca cccagaccta catctgcaac gtgaatcaca agcccagcaa caccaaggtg      660
gacaagagag ttgagcccaa atcttgtgac aaaactcaca catgcccacc gtgcccagca      720
cctgaactcc tggggggacc gtcagtcttc ctcttccccc caaaacccaa ggacaccctc      780
atgatctccc ggacccctga ggtcacatgc gtggtggtgg acgtgagcca cgaagaccct      840
gaggtcaagt tcaactggta cgtggacggc gtggaggtgc ataatgccaa gacaaagccg      900
cgggaggagc agtacaacag cacgtaccgt gtggtcagcg tcctcaccgt cctgcaccag      960
gactggctga atggcaagga gtacaagtgc aaggtctcca acaaagccct cccagccccc     1020
atcgagaaaa ccatctccaa agccaaaggt cagccccgag aaccacaggt gtacaccctg     1080
cccccatccc gggaagagat gaccaagaac caggtcagcc tgacctgcct ggtcaaaggc     1140
ttctatccca gcgacatcgc cgtggagtgg gagagcaatg ggcagccgga gaacaactac     1200
aagaccacgc ctcccgtgct ggactccgac ggctccttct tcctctatag caagctcacc     1260
gtggacaaga gcaggtggca gcaggggaac gtcttctcat gctccgtgat gcatgaggct     1320
ctgcacaacc actacacgca gaagagcctc tccctgtctc cgggtaaatg a              1371
```

<210> SEQ ID NO 49
<211> LENGTH: 1371
<212> TYPE: DNA
<213> ORGANISM: Artificial Sequence
<220> FEATURE:
<223> OTHER INFORMATION: Heavy chain of 1E4 variant (VH3)

<400> SEQUENCE: 49

```
caggtgcagc tggtgcagtc tggcgccgaa gtgaagaagc ccggctcctc cgtgaaggtc       60
tcctgccagg ctccggcta ctccttcccc acccactgga tcacctgggt gcgacaggcc      120
cccggccaag gctggaatg gatgggcacc atcgacccca ccgactccta caacttctac      180
ggccccagct tccagggcag agtgaccatc accgccgact cctccacgtc caccgcctac      240
ctgcagtggt cctccctgaa ggcctccgac accgccatgt actactgcgc cagggacggc      300
aactactacg actcccgggg ctactactac gatacccttcg acatgtgggg ccagggcacc      360
ctggtcaccg tctcctcagc ctccaccaag ggcccatcgg tcttccccct ggcaccctcc      420
tccaagagca cctctggggg cacagcggcc ctgggctgcc tggtcaagga ctacttcccc      480
gaaccggtga cggtgtcgtg gaactcaggc gccctgacca gcggcgtgca ccttcccg        540 gctgtcctac agtcctcagg actctactcc ctcagcagcg tggtgaccgt gccctccagc      600
agcttgggca cccagaccta catctgcaac gtgaatcaca agcccagcaa caccaaggtg      660
gacaagagag ttgagcccaa atcttgtgac aaaactcaca catgcccacc gtgcccagca      720
cctgaactcc tggggggacc gtcagtcttc ctcttccccc caaaacccaa ggacaccctc      780
atgatctccc ggacccctga ggtcacatgc gtggtggtgg acgtgagcca cgaagaccct      840
gaggtcaagt tcaactggta cgtggacggc gtggaggtgc ataatgccaa gacaaagccg      900
cgggaggagc agtacaacag cacgtaccgt gtggtcagcg tcctcaccgt cctgcaccag      960
gactggctga atggcaagga gtacaagtgc aaggtctcca acaaagccct cccagccccc     1020
atcgagaaaa ccatctccaa agccaaaggt cagccccgag aaccacaggt gtacaccctg     1080
cccccatccc gggaagagat gaccaagaac caggtcagcc tgacctgcct ggtcaaaggc     1140
```

| | |
|---|---|
| ttctatccca gcgacatcgc cgtggagtgg gagagcaatg gcagccgga gaacaactac | 1200 |
| aagaccacgc ctcccgtgct ggactccgac ggctccttct tcctctatag caagctcacc | 1260 |
| gtggacaaga gcaggtggca gcaggggaac gtcttctcat gctccgtgat gcatgaggct | 1320 |
| ctgcacaacc actacacgca gaagagcctc tccctgtctc cgggtaaatg a | 1371 |

<210> SEQ ID NO 50
<211> LENGTH: 1371
<212> TYPE: DNA
<213> ORGANISM: Artificial Sequence
<220> FEATURE:
<223> OTHER INFORMATION: Heavy chain of 1E4 variant (VH4)

<400> SEQUENCE: 50

| | |
|---|---|
| caggtgcagc tggtgcagtc tggcgccgaa gtgaagaagc ccggctcctc cgtgaaggtc | 60 |
| tcctgccagg gctccggcta ctccttcccc acccactgga tcacctgggt gcgacaggcc | 120 |
| cccggccaag gctggaatg gatgggcacc atcgaccca ccgactccta caacttctac | 180 |
| ggccccagct ccagggcag agtgaccatc accgccgact cctccacgtc accgcctac | 240 |
| atggagctgt cctccctgag atctgaggac accgccatgt actactgcgc cagggacggc | 300 |
| aactactacg actcccgggg ctactactac gataccttcg acatgtgggg ccagggcacc | 360 |
| ctggtcaccg tctcctcagc ctccaccaag ggcccatcgg tcttcccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagagag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |
| gaggtcaagt tcaactggta cgtggacggc gtggaggtgc ataatgccaa gacaaagccg | 900 |
| cgggaggagc agtacaacag cacgtaccgt gtggtcagcg tcctcaccgt cctgcaccag | 960 |
| gactggctga atggcaagga gtacaagtgc aaggtctcca acaaagccct cccagccccc | 1020 |
| atcgagaaaa ccatctccaa agccaaaggt cagccccgag aaccacaggt gtacaccctg | 1080 |
| cccccatccc gggaagagat gaccaagaac caggtcagcc tgacctgcct ggtcaaaggc | 1140 |
| ttctatccca gcgacatcgc cgtggagtgg gagagcaatg gcagccgga gaacaactac | 1200 |
| aagaccacgc ctcccgtgct ggactccgac ggctccttct tcctctatag caagctcacc | 1260 |
| gtggacaaga gcaggtggca gcaggggaac gtcttctcat gctccgtgat gcatgaggct | 1320 |
| ctgcacaacc actacacgca gaagagcctc tccctgtctc cgggtaaatg a | 1371 |

<210> SEQ ID NO 51
<211> LENGTH: 1371
<212> TYPE: DNA
<213> ORGANISM: Artificial Sequence
<220> FEATURE:
<223> OTHER INFORMATION: Heavy chain of 1E4 variant (VH5)

<400> SEQUENCE: 51

| | |
|---|---|
| caggtgcagc tggtgcagtc tggcgccgaa gtgaagaagc ccggctcctc cgtgaaggtc | 60 |
| tcctgccagg gctccggcta ctccttcccc acccactgga tcacctgggt gcgacaggcc | 120 |

| | |
|---|---|
| cccggccaag gcctggaatg gatgggcacc atcgacccca ccgactccta caacttctac | 180 |
| ggccccagct tccagggcag agtgaccatc accgccgact cctccacgtc caccgcctac | 240 |
| atggagctgt cctccctgag atctgaggac accgccgtgt actactgcgc cagggacggc | 300 |
| aactactacg actcccgggg ctactactac gataccttcg acatgtgggg ccagggcacc | 360 |
| ctggtcaccg tctcctcagc ctccaccaag ggcccatcgg tcttccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca ccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagagag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |
| gaggtcaagt tcaactggta cgtggacggc gtggaggtgc ataatgccaa gacaaagccg | 900 |
| cgggaggagc agtacaacag cacgtaccgt gtggtcagcg tcctcaccgt cctgcaccag | 960 |
| gactggctga atggcaagga gtacaagtgc aaggtctcca acaaagccct cccagccccc | 1020 |
| atcgagaaaa ccatctccaa agccaaaggt cagccccgag aaccacaggt gtacaccctg | 1080 |
| cccccatccc gggaagagat gaccaagaac caggtcagcc tgacctgcct ggtcaaaggc | 1140 |
| ttctatccca gcgacatcgc cgtggagtgg gagagcaatg ggcagccgga gaacaactac | 1200 |
| aagaccacgc ctcccgtgct ggactccgac ggctccttct cctctatag caagctcacc | 1260 |
| gtggacaaga gcaggtggca gcaggggaac gtcttctcat gctccgtgat gcatgaggct | 1320 |
| ctgcacaacc actacacgca gaagagcctc tccctgtctc cgggtaaatg a | 1371 |

<210> SEQ ID NO 52
<211> LENGTH: 1371
<212> TYPE: DNA
<213> ORGANISM: Artificial Sequence
<220> FEATURE:
<223> OTHER INFORMATION: Heavy chain of 1E4 variant (VH6)

<400> SEQUENCE: 52

| | |
|---|---|
| caggtgcagc tggtgcagtc tggcgccgaa gtgaagaagc ccggctcctc cgtgaaggtc | 60 |
| tcctgcaagg cttccggcta ctccttcccc acccactgga tcacctgggt gcgacaggcc | 120 |
| cccgccaag gcctggaatg gatgggcacc atcgacccca ccgactccta caacttctac | 180 |
| ggccccagct tccagggcag agtgaccatc accgccgaca gtccacgtc caccgcctac | 240 |
| atggagctgt cctccctgag atctgaggac accgccgtgt actactgcgc cagggacggc | 300 |
| aactactacg actcccgggg ctactactac gataccttcg acatgtgggg ccagggcacc | 360 |
| ctggtcaccg tctcctcagc ctccaccaag ggcccatcgg tcttccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca ccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagagag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |

```
gaggtcaagt tcaactggta cgtggacggc gtggaggtgc ataatgccaa gacaaagccg      900
cgggaggagc agtacaacag cacgtaccgt gtggtcagcg tcctcaccgt cctgcaccag      960
gactggctga atggcaagga gtacaagtgc aaggtctcca acaaagccct cccagccccc     1020
atcgagaaaa ccatctccaa agccaaaggt cagccccgag aaccacaggt gtacaccctg     1080
cccccatccc gggaagagat gaccaagaac caggtcagcc tgacctgcct ggtcaaaggc     1140
ttctatccca gcgacatcgc cgtggagtgg gagagcaatg gcagccgga gaacaactac      1200 aagaccacgc ctcccgtgct ggactccgac ggctccttct tcctctatag caagctcacc     1260
gtggacaaga gcaggtggca gcaggggaac gtcttctcat gctccgtgat gcatgaggct     1320
ctgcacaacc actacacgca gaagagcctc tccctgtctc cgggtaaatg a              1371
```

<210> SEQ ID NO 53
<211> LENGTH: 645
<212> TYPE: DNA
<213> ORGANISM: Artificial Sequence
<220> FEATURE:
<223> OTHER INFORMATION: Light chain of 1E4 (Vk)

<400> SEQUENCE: 53

```
gacatccaga tgacccagtc ccccagcttc ctgtccgcct ccgtgggcga cagagtgacc       60
atcacctgtc gggcctccca gggcatctcc acctacctgg cctggtatca gcagaagccc      120
ggcaccgccc ccaagctgct gatctactcc gcctccaccc tggaatccgg cgtgccctcc      180
agattctccg gctccggctc tggcaccgac ttcaccctga ccatctccag cctgcagccc      240
gaggactccg ccacctacta ctgccagcag gccgactcct tcccctgac cttcggcgga      300 ggcaccaagg tggaaatcaa agatccgtg ccgctccct ccgtgttcat cttcccaccc       360
tccgacgagc agctgaagtc tggcaccgcc agcgtggtct gcctgctgaa caacttctac      420
ccccgcgagg ccaaggtgca gtggaaggtg gacaacgccc tgcagtccgg caactcccag      480
gaatccgtca ccgagcagga ctccaaggac agcacctact ccctgtccag cacccctgacc     540 ctgtccaagg ccgactacga gaagcacaag gtgtacgcct gcgaagtgac ccaccagggc      600
ctgtccagcc ctgtgaccaa gtccttcaac cggggcgagt gctga                     645
```

<210> SEQ ID NO 54
<211> LENGTH: 645
<212> TYPE: DNA
<213> ORGANISM: Artificial Sequence
<220> FEATURE:
<223> OTHER INFORMATION: Light chain of 1E4 variant (Vk0)

<400> SEQUENCE: 54

```
gacatccaga tgacccagtc ccccagcttc ctgtccgcct ccgtgggcga cagagtgacc       60
atcacctgtc gggcctccca gggcatctcc acctacctgg cctggtatca gcagaagccc      120
ggcaccgccc ccaagctgct gatctactcc gcctccaccc tggaatccgg cgtgccctcc      180
agattctccg gctccggctc tggcaccgac ttcaccctga ccatctccag cctgcagccc      240
gaggactccg ccacctacta ctgccagcag gccgactcct tcccctgac cttcggcgga      300 ggcaccaagg tggaaatcaa acgtactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg ataacgccc tccaatcggg taactcccag       480
gagagtgtca cagagcagga cagcaaggac agcacctaca gcctcagcag caccctgacg      540
```

```
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 55
<211> LENGTH: 645
<212> TYPE: DNA
<213> ORGANISM: Artificial Sequence
<220> FEATURE:
<223> OTHER INFORMATION: Light chain of 1E4 variant (Vk2)

<400> SEQUENCE: 55

```
gacatccaga tgacccagtc ccccagctcc ctgtccgcct ccgtgggcga cagagtgacc     60
atcacctgtc gggcctccca gggcatctcc acctacctgg cctggtatca gcagaagccc    120
ggcaaagccc ccaagctgct gatctactcc gcctccaccc tggaatccgg cgtgccctcc    180
agattctccg gctccggctc tggcaccgac ttcaccctga ccatctccag cctgcagccc    240
gaggactttg ccacctacta ctgccagcag gccgactcct tcccccctga cttcggcgga    300
ggcaccaagg tggaaatcaa acgtactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 56
<211> LENGTH: 645
<212> TYPE: DNA
<213> ORGANISM: Artificial Sequence
<220> FEATURE:
<223> OTHER INFORMATION: Light chain of 1E4 variant (Vk3)

<400> SEQUENCE: 56

```
gacatccaga tgacccagtc cccccggcttc ctgtccttgt ccccaggcga aagagccacc    60
ctctcctgtc gggcctccca gggcatctcc acctacctgg cctggtatca gcagaagccc    120
ggccaggccc ccaggctgct gatctactcc gcctccaccc tggaatccgg cgtgcccgac    180
agattctccg gctccggctc tggcaccgac ttcaccctga ccatctccag actggagccc    240
gaggactttg ccacctacta ctgccagcag gccgactcct tcccccctga cttcggcgga    300
ggcaccaagg tggaaatcaa acgtactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 57
<211> LENGTH: 645
<212> TYPE: DNA
<213> ORGANISM: Artificial Sequence
<220> FEATURE:
<223> OTHER INFORMATION: Light chain of 1E4 variant (Vk4)

<400> SEQUENCE: 57

```
gaaatccaga tgacccagtc ccccggcacc ctgtccttgt ccccaggcga aagagccacc    60
```

```
ctctcctgtc gggcctccca gggcatctcc acctacctgg cctggtatca gcagaagccc    120
ggccaggccc ccaggctgct gatctactcc gcctccaccc tggaatccgg cgtgcccgac    180
agattctccg gctccggctc tggcaccgac ttcaccctga ccatctccag actggagccc    240
gaggactttg ccacctacta ctgccagcag gccgactcct tcccctgac cttcggcgga    300
ggcaccaagg tggaaatcaa acgtactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacacaaa gtctacgcct gcgaagtcac ccatcagggc    600
ctgagctcgc ccgtcacaaa gagcttcaac aggggagagt gttag                   645

<210> SEQ ID NO 58
<211> LENGTH: 645
<212> TYPE: DNA
<213> ORGANISM: Artificial Sequence
<220> FEATURE:
<223> OTHER INFORMATION: Light chain of 1E4 variant (Vk5)

<400> SEQUENCE: 58
gaaatcgtgt tgacccagtc ccccggcacc ctgtccttgt ccccaggcga aagagccacc     60
ctctcctgtc gggcctccca gggcatctcc acctacctgg cctggtatca gcagaagccc    120
ggccaggccc ccaggctgct gatctactcc gcctccaccc tggaatccgg catcccgac     180
agattctccg gctccggctc tggcaccgac ttcaccctga ccatctccag actggagccc    240
gaggactttg ccacctacta ctgccagcag gccgactcct tcccctgac cttcggcgga    300
ggcaccaagg tggaaatcaa acgtactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacacaaa gtctacgcct gcgaagtcac ccatcagggc    600
ctgagctcgc ccgtcacaaa gagcttcaac aggggagagt gttag                   645
```

ANTI-C-MET ANTIBODY SHOWING ENHANCED STABILITY OR ANTIGEN-BINDING FRAGMENTS THEREOF

CROSS-REFERENCE TO RELATED APPLICATIONS

This application is a national phase application of PCT Application No. PCT/KR2019/015475 filed on Nov. 13, 2019, which claims the benefit of and priority to Korean Patent Application No. 10-2018-0140196 filed on Nov. 14, 2018. The entire disclosures of the applications identified in this paragraph are incorporated herein by references.

TECHNICAL FIELD

The present disclosure was made with the support of the Ministry of Health and Welfare, Republic of Korea, under Project No. H117C1693, which is conducted by the Seoul Metropolitan Government Seoul National University Borame Hospital Medical Center in the research project named "Non-clinical Development and Mechanism Study of Biomedical Product for Kidney Disease by Using Anti-Met Antibody" in the research program titled "Development of Technique for Disease Treatment" under management of the Korea Health Industry Development Institute, from 10 Apr. 2017 to 31 Dec. 2019.

BACKGROUND ART c-Met (mesenchymal-epithelial transition factor), which is expressed on a cell surface, is a receptor tyrosine kinase that is encoded by Met proto-oncogene. Structurally, c-Met is a disulfide-linked heterodimer consisting of an extracellular alpha subunit (50 kDa) and a transmembrane beta subunit (140 kDa) and is characterized by an extracellular domain for ligand binding, a membrane-spanning segment, and a tyrosine kinase catalytic motif involved in phosphorylation of tyrosine residues within an intracellular domain (Dean et al., Nature, 4: 318 (6044): 385, 1985; Park et al., PNAS, 84 (18): 6379, 1976; Maggiora et al., J. Cell Physiol., 173:183, 1997).

Upon binding to the ligand HGF (hepatocyte growth factor), c-Met dimerizes and autophosphorylates cytoplasmic tyrosine residues, then in turn interacts with various proteins that mediate downstream signaling pathways. c-Met activation results in a variety of biological responses which lead to increased cell growth, scattering and motility, invasion, protection from apoptosis, branching morphogenesis, and angiogenesis. Under pathological conditions, improper activation of c-Met may confer proliferative, survival and invasive/metastatic abilities of cancer cells. Given the variety of biological and physiological functions impacted by c-Met activity, the c-Met protein has become a versatile therapeutic target.

The present inventors developed c-Met immunoglobulins which bind to and activate the c-Met protein and which are prophylactically and/or therapeutically effective in a variety of disorders or diseases (WO2016/021864A1; and WO2017/135791A1). However, the IgG1-based anti-c-Met antibody 1E4 developed by the present inventors (WO2016/021864A1; and WO2017/135791A1) exhibits structural instability during a production process thereof although having high affinity for c-Met. Intensive and through research into the development of a structurally stable antibody retaining the affinity and biopotency of the conventional antibody has been conducted by the present inventors, leading to the present disclosure.

Numerous papers and patent documents (WO2016/021864 A1; and WO2017/135791 A1) are referenced and cited throughout this description. The disclosures of the cited papers and patent documents are incorporated herein by reference in their entirety to better understand the state of the art to which the present disclosure pertains and the content of the present disclosure.

RELATED ART DOCUMENTS

Non-Patent Literature (Non-patent literature 1) Perry, L. C. A., Jones, T. D. & Baker, M. P., 2008. New approaches to prediction of immune responses to therapeutic proteins during pre-clinical development. Drugs in R&D, 9(6), pp. 385-96

(Non-patent literature 2) Bryson, C. J., Jones, T. D. & Baker, M. P., 2010. Prediction of immunogenicity of therapeutic proteins: validity of computation tools. BioDrugs: clinical immunotherapeutics, biopharmaceuticals and gene therapy, 24(1), pp. 1-8

SUMMARY

Technical Problem

The present inventors have made intensive and thorough research into the development of an antibody having structural stability while retaining the affinity and biopotency of the previously developed anti-c-Met antibody 1E4. Structural stability of antibodies is an important consideration in the commercial development of drugs. If not structurally stable, an antibody suffers from the problems of disadvantageous quality control, poor efficiency, and increased side effects. In order to maintain the affinity of the conventional anti-c-Met antibody 1E4 for c-Met, the present inventors conducted CDR grafting by which complementarity determining regions (CDRs) are grafted into more stable framework regions and, as a result, found an antibody or an antigen binding fragment structurally more stable than the conventional antibody, which led to the present disclosure.

Therefore, an aspect of the present disclosure is to provide an anti-c-Met antibody or an antigen-binding fragment thereof that exhibits improved stability.

Another aspect of the present disclosure is to provide a nucleic acid molecule encoding the anti-c-Met antibody or the antigen-binding fragment thereof which exhibits improved stability.

A further aspect of the present disclosure is to provide a recombinant vector carrying the nucleic acid molecule.

A still further aspect of the present disclosure is to provide a host cell transformed with the recombinant vector.

A still another aspect of the present disclosure is to provide a pharmaceutical composition for treatment of an ischemic disease, stroke, a kidney injury or disease, a retinal neovascularization disorder, neurological disorder or disease, or a wound.

An additional aspect of the present disclosure is to provide a method for treatment of an ischemic disease, stroke, a kidney injury or disease, a retinal neovascularization disorder, neurological disorder or disease, or a wound.

Other purposes and advantages of the present disclosure will be apparent with reference to the following description, claims, and drawings.

Technical Solution

With the aim of improving structural stability in the previously developed anti-c-Met antibody 1E4 (see WO2016/021864A1; and WO2017/135791A1), the present inventors performed CDR grafting to construct a 1E4 antibody variant that exhibits high affinity for an antigen, low immunogenicity, and high stability and biopotency.

As used herein, the term "antibody" refers to an antibody specific for c-Met and is intended to encompass an antigen-binding fragment of the antibody molecule as well as an intact antibody form.

An intact antibody consists of two full-length light chains and two full-length heavy chain, with disulfide linkages therebetween. Heavy chain constant domains are classified into gamma ($\gamma$), mu ($\mu$), alpha ($\alpha$), delta ($\delta$), and epsilon ($\epsilon$) types, with the subclassification of the gamma type into gamma 1 ($\gamma$1), gamma 2 ($\gamma$2), gamma 3 ($\gamma$3), and gamma 4 ($\gamma$4), and the alpha type into alpha 1 ($\alpha$1) and alpha 2 ($\alpha$2). Antibodies can be further classified by kappa ($\kappa$) and lambda ($\lambda$) types for light chain constant domains (Cellular and Molecular Immunology, Wonsiewicz, M. J., Ed., Chapter 45, pp. 41-50, W. B. Saunders Co. Philadelphia, PA (1991); Nisonoff, A., Introduction to Molecular Immunology, 2nd Ed., Chapter 4, pp. 45-65, Sinauer Associates, Inc., Sunderland, MA (1984)).

As used herein, the term "antigen-binding fragment" means a fragment retaining the function of binding to an antigen and is intended to encompass Fab, F(ab'), F(ab')$_2$, chemically linked F(ab')$_2$, Fv, and so on. Of the antibody fragments, Fab has one antigen-binding site which takes on the structure composed of light chain and heavy chain variable domains, a light chain constant domain, and the first constant domain (CH1 domain) of the heavy chain. Fab' is different from Fab in that the former has a hinge region containing at least one cysteine residue at the C terminus of the heavy chain CH1 domain. An F(ab')$_2$ antibody is produced in such a way that a cysteine residue of the hinge region of Fab' forms disulfide bonding. Fv is a minimum antibody fragment having only a heavy chain variable domain and a light chain variable domain. A recombination technology for producing an Fv fragment is disclosed in the International Patent Publication filed under the patent cooperation treaty (PCT) WO 88/10649, WO 88/106630, WO 88/07085, WO 88/07086, and WO 88/09344. In case of two-chain Fv, a heavy chain variable domain and a light chain variable domain are linked to each other by means of non-covalent bonding while single-chain Fv consists of a heavy chain variable domain and a single chain variable domain which are linked to each other by means of covalent bonding generally via a peptide linker, or directly linked to each other at C-terminus, and thus may form a structure like a dimer, as shown in the two-chain Fv. Such antibody fragments may be obtained by using protease (for example, Fab may be obtained by performing restriction digestion of a whole antibody with papain, while F(ab')$_2$ fragment may be obtained by doing so with pepsin), and may be prepared by means of a gene recombination technology.

The antibody in the present disclosure is preferably in the form of scFv or in an intact form. In addition, the heavy chain constant domain may be any one isotype selected from gamma ($\gamma$), mu ($\mu$), alpha ($\alpha$), delta ($\delta$), and epsilon ($\epsilon$). Preferably, the constant domain may be a gamma 1 (IgG1), gamma 3 (IgG3), or gamma 4 (IgG4) isotype, with most preference for gamma 1 (IgG1) isotype. The light chain constant domain may be a kappa or lambda isotype, with preference for kappa isotype. Therefore, a preferred antibody of the present disclosure is in the form of scFv or IgG1 including a kappa ($\kappa$) light chain and a gamma 1 ($\gamma$1) heavy chain.

The term "heavy chain", as used herein, refers to a full-length heavy chain including: a variable domain V$_H$, which comprises amino acid sequences having enough variable domain sequences to allow the specificity to an antigen; and the three constant domains, C$_H$1, C$_H$2, and C$_H$3, and to any fragment thereof. As used herein, the term "light chain" refers to a full-length light chain including: a variable domain V$_L$ (Vk), which comprises amino acid sequences having enough variable domain sequences to allow the specificity to an antigen; and a constant domain, CL (Ok) and to any fragment thereof.

The term "CDR" (complementarity determining region), as used herein, refers to an amino acid sequence in a hypervariable region of an immunoglobulin heavy chain or light chain (Kabat et al., Sequences of Proteins of Immunological Interest, 4$^{th}$ Ed., U.S. Department of Health and Human Services, National Institutes of Health (1987)). Three CDRs exist in each of the heavy chain (CDRH1, CDRH2, and CDRH3) and the light chain (CDRL1, CDRL2, and CDRL3). CDRs provide contact residues which play an important role in binding the antibody to an antigen or an epitope.

Examples of the antibody of the present disclosure include, but are not limited to, monoclonal antibodies, multispecific antibodies, human antibodies, humanized antibodies, chimeric antibodies, single-chain Fvs (scFV), single-chain antibodies, Fab fragments, F(ab') fragments, disulfide-linked Fvs (sdFv), anti-idiotypic (anti-Id) antibodies, and epitope-binding fragments of the antibodies.

The term "framework" or "FR", as used herein, refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL/Vk):

(a) FRH1 (framework region 1 of heavy chain)-CDRH1 (complementarity determining region 1 of Heavy chain)-FRH2-CDRH2-FRH3-CDRH3-FRH4; and (b) FRL1(framework region 1 of light chain)-CDRL1 (complementarity determining region 1 of Light chain)-FRL2-CDRL2-FRL3-CDRL3-FRL4.

The term "variable region" or "variable domain" refers to the domain of an antibody heavy or light chain responsible for binding the antibody to antigen. The variable domains of the heavy chain and light chain (VH and VL, respectively) of a native antibody generally have similar structures, with each domain comprising four conserved framework regions (FRs) and three hypervariable regions (HVRs). (Kindt et al. Kuby Immunology, 6$^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively.

The term "specifically binds" or similar expressions mean that an antibody or an antigen-binding fragment thereof, or another construct such as an scFv, forms a complex with an antigen that is relatively stable under physiologic conditions. Specific binding can be characterized by an equilibrium dissociation constant of at least about $1\times10^{-6}$ M or less (e.g., a smaller K$_D$ denotes a tighter binding). Methods for determining whether two molecules specifically bind are well known in the art and include, for example, equilibrium dialysis, surface plasmon resonance, and the like. An isolated antibody that specifically binds human c-Met may, however, exhibit cross-reactivity to other antigens such as c-Met molecules from other species.

As used herein, the term "affinity" refers to total strength of noncovalent interactions between a single binding site of a molecule (e.g., an antibody) and its binding partner (e.g., an antigen). Unless specified otherwise, "binding affinity", as used herein, refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody, which comprises non-human antigen-binding residues.

The term "chimeric" antibody, as used herein, refers to an antibody in which a portion of the heavy and/or light chain is derived from a particular source or species, while the remainder of the heavy and/or light chain is derived from a different source or species.

In order to confer improved structural stability on the IgG1-based anti-c-Met antibody 1E4 disclosed in WO2016/021864A1 and WO2017/135791A1 while preserving characteristics of the anti-c-Met antibody, advantage was taken of a CDR grafting method by which the complementarity determining regions (CDRs) of a preexisting antibody are grafted into a framework more stable than that of the preexisting antibody.

"CDR grafting" is one of the most representative methods for humanizing non-human antibodies, developed to solve the problem that when used in a human patient, a mouse monoclonal antibody is neutralized by an immune response induced thereby. CDR grafting refers to grafting a CDR region of an animal antibody to the framework of a human antibody.

In order to select an optimal framework region, an application was made to the CDR grafting method in accordance with the present disclosure. In this regard, sequence homology was examined between amino acid sequences of the heavy chain variable domain and light chain variable domain of a human antibody and the heavy chain variable domain (VH) and light chain variable domain (Vk) of the anti-c-Met antibody 1E4 and candidate sequences, and the amino sequences were screened for candidate sequences having high sequence homology from which variants of an anti-c-Met antibody or antigen-binding fragments thereof having improved stability were constructed according to the present disclosure.

Provided according to an aspect of the present disclosure is an anti-c-Met antibody or an antigen-binding fragment comprising:
(a) an immunoglobulin heavy chain variable domain including the structure of FRH1-CDRH1-FRH2-CDRH2-FRH3-CDRH3-FRH4; and
(b) an immunoglobulin light chain variable domain including the structure of FRL1-CDRL1-FRL2-CDRL2-FRL3-CDRL3-FRL4:
wherein the CDRH1 (complementarity determining region 1 of heavy chain), the CDRH2, and the CDRH3 include the amino acid sequences of SEQ ID NOS: 1, 2, and 3, respectively, and the CDRL1 (complementarity determining ing region 1 of light chain), CDRL2, and CDRL3 include the amino acid sequences of SEQ ID NOS: 4, 5, and 6, respectively.

According to an embodiment, the FRH1 (framework region 1 of heavy chain) of the heavy chain variable domain of (a) in the anti-c-Met antibody or antigen-binding fragment of the present disclosure comprises the amino acid sequence of i):

i) 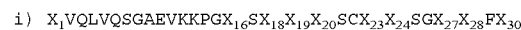

wherein, $X_1$ is Q or E;
$X_{16}$ is E or S;
$X_{18}$ is L or V;
$X_{19}$ is R or K;
$X_{20}$ is I or V;
$X_{23}$ is Q or K;
$X_{24}$ is G or A;
$X_{27}$ is Y;
$X_{28}$ is S; and
$X_{30}$ is P, independently.

As used herein, the symbols represented by those such as "$X_n$", "$X_m$", etc. refer to amino acids at positions n, m, etc. in the sequences i) to viii) given below. In the symbols, n and m are integers indicating positions of amino acids from the N-terminus on the sequence. For example, $X_3$ and $X_7$ represent amino acids at positions 3 and 7 from the n-terminus of the sequence, respectively.

In one embodiment according to an aspect of the present disclosure, $X_n$ in sequence i) is independently selected from the group of interchangeable amino acids given thereto. It should be understood to a person skilled in the art that $X_n$ is selected from the amino acid residues as interchangeable residues given thereto and that the selection is independent of that for the amino acid of $X_m$ wherein n and m are different from each other. Therefore, an independent combination may be made between any of the residues given for $X_n$ position and any of the residues given for other various positions.

In an exemplary embodiment of the present disclosure, the sequence of i) comprises specific amino acid residues selected as follows:

$X_1$ is Q; $X_{16}$ is E; $X_{18}$ is L; $X_{19}$ is R; $X_{20}$ is I; $X_{23}$ is Q; $X_{24}$ is G; $X_{27}$ is Y; $X_{28}$ is S; and $X_{30}$ is P.

In another exemplary embodiment, the sequence of i) comprises specific amino acid residues selected as follows:

$X_1$ is E, $X_{19}$ is K, $X_{23}$ is K, and $X_{30}$ is P;
$X_{16}$ is S, $X_{18}$ is V, $X_{19}$ is K, and $X_{20}$ is V; or
$X_{16}$ is S, $X_{18}$ is V, $X_{19}$ is K, $X_{20}$ is V, $X_{23}$ is K, and $X_{24}$ is A.

According to another embodiment of the present disclosure, the FRH2 (framework region 2 of heavy chain) of the heavy chain variable domain of (a) in the anti-c-Met antibody or antigen-binding fragment of the present disclosure comprises the amino acid sequence of ii):

ii) 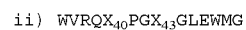

wherein, $X_{40}$ is M or A; and
$X_{43}$ is K or Q, independently.

According to an exemplary embodiment of the present disclosure, the sequence of ii) comprises specific amino acid residues selected as follows:

$X_{40}$ is M; and $X_{43}$ is K.

According to another exemplary embodiment of the present disclosure, the sequence of ii) comprises specific amino acid residues selected as follows:

$X_{40}$ is A, and $X_{43}$ is Q.

According to another embodiment of the present disclosure, the FRH3 (framework region 3 of heavy chain) of the heavy chain variable domain of (a) in the anti-c-Met antibody or antigen-binding fragment of the present disclosure comprises the amino acid sequence of iii):

iii) $X_{67}$VTI$X_{71}$AD$X_{74}$S$X_{76}$STAY$X_{81}X_{82}X_{83}$SSL$X_{87}X_{88}X_{89}$DTA$X_{93}$YYCAR wherein, $X_{67}$ is H, Q, or R;
$X_{71}$ is S or T;
$X_{74}$ is S or K;
$X_{76}$ is S, I, or T;
$X_{81}$ is L or M;
$X_{82}$ is Q or E;
$X_{83}$ is W or L;
$X_{87}$ is K or R;
$X_{88}$ is A or S;
$X_{89}$ is S or E;
$X_{93}$ is M or V, independently.

According to an exemplary embodiment of the present disclosure, the sequence of iii) comprises specific amino acid residues selected as follows:

$X_{67}$ is H; $X_{71}$ is S; $X_{74}$ is S; $X_{76}$ is S; $X_{81}$ is L; $X_{82}$ is Q; $X_{83}$ is W; $X_{87}$ is K; $X_{88}$ is A; $X_{89}$ is S; and $X_{93}$ is M.

According to an exemplary embodiment of the present disclosure, the sequence of iii) comprises specific amino acid residues selected as follows:

$X_{67}$ is Q, $X_{74}$ is K, and $X_{76}$ is I;
$X_{67}$ is R, $X_{71}$ is T, and $X_{76}$ is T;
$X_{67}$ is R, $X_{71}$ is T, $X_{76}$ is T, $X_{81}$ is M, $X_{82}$ is E, $X_{83}$ is L, $X_{87}$ is R, $X_{88}$ is S, and $X_{89}$ is E;
$X_{67}$ is R, $X_{71}$ is T, $X_{76}$ is T, $X_{81}$ is M, $X_{82}$ is E, $X_{83}$ is L, $X_{87}$ is R, $X_{88}$ is S, $X_{89}$ is E, and $X_{93}$ is V; or
$X_{67}$ is R, $X_{71}$ is T, $X_{74}$ is K, $X_{76}$ is T, $X_{81}$ is M, $X_{82}$ is E, $X_{83}$ is L, $X_{87}$ is R, $X_{88}$ is S, $X_{89}$ is E, and $X_{93}$ is V.

According to another embodiment of the present disclosure, the FRH4 (framework region 4 of heavy chain) of the heavy chain variable domain of (a) in the anti-c-Met antibody or antigen-binding fragment of the present disclosure comprises the amino acid sequence of iv):

iv) WGQGTLVTVSS

According to another embodiment of the present disclosure, the FRL1 (framework region 1 of light chain) of the light chain variable domain of (b) in the anti-c-Met antibody or antigen-binding fragment of the present disclosure comprises the amino acid sequence of v):

v) $X_1$I$X_3X_4$TQSP$X_9X_{10}$LS$X_{13}$S$X_{15}$G$X_{17}$R$X_{19}$T$X_{21}X_{22}$C wherein, $X_1$ is D or E;
$X_3$ is Q or V;
$X_4$ is M or L;
$X_9$ is S or G;
$X_{10}$ is F, S, or T;
$X_{13}$ is A or L;
$X_{15}$ is V or P;
$X_{17}$ is D or E;
$X_{19}$ is V or A;
$X_{21}$ is I or L; and
$X_{22}$ is T or S, independently.

According to an exemplary embodiment of the present disclosure, the sequence of v) comprises specific amino acid residues selected as follows:

$X_1$ is D; $X_3$ is Q; $X_4$ is M; $X_9$ is S; $X_{10}$ is F; $X_{13}$ is A; $X_{15}$ is V; $X_{17}$ is D; $X_{19}$ is V; $X_{21}$ is I; and $X_{22}$ is T.

According to an exemplary embodiment of the present disclosure, the sequence of v) comprises specific amino acid residues selected as follows:

$X_{10}$ is S;
$X_9$ is G, $X_{13}$ is L, $X_{15}$ is P, $X_{17}$ is E, $X_{19}$ is A, $X_{21}$ is L, and $X_{22}$ is S;
$X_1$ is E, $X_9$ is G, $X_{10}$ is T, $X_{13}$ is L, $X_{15}$ is P, $X_{17}$ is E, $X_{19}$ is A, $X_{21}$ is L, and $X_{22}$ is S; or
$X_1$ is E, $X_3$ is V, $X_4$ is L, $X_9$ is G, $X_{10}$ is T, $X_{13}$ is L, $X_{15}$ is P, $X_{17}$ is E, $X_{19}$ is A, $X_{21}$ is L, and $X_{22}$ is S.

According to another embodiment of the present disclosure, the FRL2 (framework region 2 of light chain) of the light chain variable domain of (b) in the anti-c-Met antibody or antigen-binding fragment of the present disclosure comprises the amino acid sequence of vi):

vi) WYQQKPG$X_{42}$AP$X_{45}$LLIY wherein $X_{42}$ is T, K, or Q; and
$X_{45}$ is K or R.

According to an exemplary embodiment of the present disclosure, the sequence of vi) comprises specific amino acid residues selected as follows:

$X_{42}$ is T; and $X_{45}$ is K.

According to an exemplary embodiment of the present disclosure, the sequence of vi) comprises specific amino acid residues substituted as follows:

$X_{42}$ is K; or
$X_{42}$ is Q, and $X_{45}$ is R.

According to another embodiment of the present disclosure, the FRL3 (framework region 3 of light chain) of the light chain variable domain of (b) in the anti-c-Met antibody or antigen-binding fragment of the present disclosure comprises the amino acid sequence of vii):

vii) G$X_{58}$P$X_{60}$RFSGSGSGTDFTLTIS$X_{77}$L$X_{79}$PED$X_{83}$ATYYC $X_{58}$ is V or I;
$X_{60}$ is S or D;
$X_{77}$ is S or R;
$X_{79}$ is Q or E; and
$X_{83}$ is S or F.

In the sequence of vii) according to an exemplary embodiment of the present disclosure, $X_{58}$ is V; $X_{60}$ is S; $X_{77}$ is S; $X_{79}$ is Q; and $X_{83}$ is S.

According to an exemplary embodiment of the present disclosure, the sequence of vii) comprises specific amino acid residues selected as follows:

$X_{83}$ is F;
$X_{60}$ is D, $X_{77}$ is R, $X_{79}$ is E, and $X_{83}$ is F; or
$X_{58}$ is I, $X_{60}$ is D, $X_{77}$ is R, $X_{79}$ is E, and $X_{83}$ is F.

According to another embodiment of the present disclosure, the FRL4 (framework region 4 of light chain) of the light chain variable domain of (b) in the anti-c-Met antibody or antigen-binding fragment of the present disclosure comprises the amino acid sequence of viii):

```
viii) FGGGTKVEIK
``` which is a common framework region of the light chain variable region of the antibody in the present disclosure. This sequence represents the last 10 amino acids of the light chain variable region sequences listed as SEQ ID NOs: 17, 18, 19, 20, and 21 (i.e., amino acids 98-107 of SEQ ID NOs: 17, 18, 19, 20, and 21).

In accordance with an exemplary embodiment of the present disclosure, the anti-c-Met antibody or antigen-binding fragment of the present disclosure comprises:
  any one selected from amino acid sequences of SEQ ID NOS: 11 to 16 and SEQ ID NOS: 34 to 39; and
  any one selected from amino acid sequences of SEQ ID NOS: 17 to 21 and SEQ ID NOS: 41 to 45.

In accordance with another aspect thereof, the present disclosure provides an anti-c-Met antibody or an antigen-binding fragment thereof, comprising:
  (a) a heavy chain variable domain including CDRH1 (complementarity determining region 1 of heavy chain) of SEQ ID NO: 1, CDRH2 of SEQ ID NO: 2, and CDRH3 of SEQ ID NO: 3;
  (b) an immunoglobulin heavy chain constant domain including CH1 (constant domain 1 of heavy chain) of SEQ ID NO: 7;
  (c) an immunoglobulin light chain variable domain including CDRL1 (complementarity determining region 1 of Light chain) of SEQ ID NO: 4, CDRL2 of SEQ ID NO: 5, and CDRL3 of SEQ ID NO: 6; and
  (d) an immunoglobulin light chain constant domain including Ck (kappa-constant domain) of SEQ ID NO: 8,
  wherein at least one of the amino acid residue at position 97 in CH1 of SEQ ID NO: 7 and the amino acid residue at position 2 in Ck of SEQ ID NO: 8 is mutated by substitution with arginine or threonine.

In the anti-c-Met antibody or the antigen-binding fragment thereof according to an embodiment of the present disclosure, the amino acid residue at position 97 in CH1 of SEQ ID NO: 7 and the amino acid residue at position 2 in Ck of SEQ ID NO: 8 are mutated by substitution with arginine and threonine, respectively.

The CH1 of SEQ ID NO: 7 in which the amino acid residue at position 97 is mutated by substitution with arginine and the Ck of SEQ ID NO: 8 in which the amino acid residue at position 2 is mutated by substitution with threonine are identical to the CH1 of SEQ ID NO: 9 and the Ck of SEQ ID NO: 8, respectively.

The substitution mutation for the amino acid residues is intended to construct the constant domain of the conventional anti-c-Met antibody 1E4 into a sequence identical to those of the human germ-line. CH1 of SEQ ID NO: 7 and Ck of SEQ ID NO: 8, which are the constant domain sequences in the conventional anti-c-Met antibody 1E4, contain sequences that are not found in a general human population.

According to another embodiment of the present disclosure, (a) the immunoglobulin heavy chain variable domain in the anti-c-Met antibody or antigen-binding fragment of the present disclosure includes any one of the amino acid sequences of SEQ ID NOS: 11 to 16.

The amino acid sequence of SEQ ID NO: 11 amounts to the heavy chain variable domain (VH or VH0) of the conventional anti-c-Met antibody 1E4. The amino acid sequence of SEQ ID NO: 12 is a candidate sequence (VH2) derived from IGHV5-51*01, which is a candidate sequence for a human heavy chain variable domain screened for the CDR grafting of the anti-c-Met antibody in the present disclosure. The amino acid sequences of SEQ ID NOS: 13 to 16 are respective candidate sequences (VH3, VH4, VH5, and VH6) derived from IGHV1-69*02, which is a candidate sequence for a human heavy chain variable domain According to an exemplary embodiment of the present disclosure, (a) the immunoglobulin heavy chain variable domain of the anti-c-Met antibody or antigen-binding fragment in the present disclosure includes any one of the amino acid sequences of SEQ ID NOS: 11 and 14 to 16, and more particularly any one of the amino acid sequences of SEQ ID NOS: 14 to 16.

According to another embodiment of the present disclosure, (c) the immunoglobulin light chain variable domain of the anti-c-Met antibody or antigen-binding fragment in the present disclosure includes any of the amino acid sequences of SEQ ID NOS: 17 to 21.

The amino acid sequence of SEQ ID NO: 17 amounts to the light chain variable domain (Vk or Vk0) of the conventional anti-c-Met antibody 1E4. The amino acid sequence of SEQ ID NO: 18 is a candidate sequence (Vk2) derived from IGKV1-39*01, which is a candidate sequence for a human light chain variable domain screened for the CDR grafting of the anti-c-Met antibody in the present disclosure. The amino acid sequences of SEQ ID NOS: 19 to 21 are respective candidate sequences (Vk3, Vk4, and Vk5)) derived from IGKV3-20*01, which is a candidate sequence for a human light chain variable domain.

According to an exemplary embodiment of the present disclosure, (c) the immunoglobulin light chain variable domain of the anti-c-Met antibody or antigen-binding fragment in the present disclosure includes any of the amino acid sequence of SEQ ID NO: 17 or 18.

In the anti-c-Met antibody or antigen-binding fragment according to another embodiment of the present disclosure, (a) the immunoglobulin heavy chain variable domain includes any one of the amino acid sequences of SEQ ID NOS: 14 to 16 and (c) the immunoglobulin light chain variable domain includes the amino acid sequence of SEQ ID NO: 17 or 18.

In the anti-c-Met antibody or antigen-binding fragment according to another embodiment of the present disclosure, (a) the immunoglobulin heavy chain variable domain includes the amino acid sequence of SEQ ID NO: 14 and (c) the immunoglobulin light chain variable domain includes the amino acid sequence of SEQ ID NO: 18.

According to an embodiment of the present disclosure, the anti-c-Met antibody of the present disclosure is in an intact antibody form. The intact antibody form includes a heavy chain constant domain selected from any one of gamma (γ), mu (ρ), alpha (α), delta (δ), and epsilon (ε) isotypes and a light chain constant domain selected from any one of kappa and lambda isotypes, and preferably is an IgG1 form including a gamma 1 (γ1) heavy chain constant domain and a kappa (κ) light chain constant domain, but without limitations thereto.

According to another embodiment of the present embodiment, the antigen-binding fragment of the anti-c-Met antibody of the present disclosure is Fab, Fab', F(ab')$_2$, Fv, scFv, or chemically linked F(ab')$_2$ and preferably scFv, but is not limited thereto.

Another aspect of the present disclosure provides a nucleic acid molecule encoding the anti-c-Met antibody or antigen-binding fragment of the present disclosure.

As used herein, the term "nucleic acid molecule" is intended to comprehensively encompass RNA molecules as well as DNA (gDNA and cDNA), and nucleotides, which account for a basic unit of nucleic acid molecules, include not only natural nucleotides but also analogues having modified sugar or base moieties (Scheit, Nucleotide Analogs, John Wiley, New York (1980); Uhlman and Peyman, Chemical Reviews, 90:543-584(1990)).

Considering biologically equivalent variations described in the foregoing, the nucleic acid molecule coding for the amino acid sequence accounting for the antibody or antigen-binding fragment of the present disclosure is construed to encompass sequences having substantial identity to them. Sequences having the substantial identity show at least 60%, particularly at least 70%, more particularly 80%, even more particularly at least 90%, most particularly at least 95% similarity to the nucleic acid molecule of this disclosure, as measured by using one of the sequence comparison algorithms for the sequences of the present disclosure aligned to any sequence, with maximum correspondence therebetween. Methods of alignment of sequences for comparison are well-known in the art. Various programs and alignment algorithms are disclosed in: Smith and Waterman, Adv. Appl. Math. 2:482(1981); Needleman and Wunsch, J. Mol. Bio. 48:443(1970); Pearson and Lipman, Methods in Mol. Biol. 24: 307-31(1988); Higgins and Sharp, Gene 73:237-44(1988); Higgins and Sharp, CABIOS 5:151-3(1989); Corpet et al., Nuc. Acids Res. 16:10881-90(1988); Huang et al., Comp. Appl. BioSci. 8:155-65(1992) and Pearson et al., Meth. Mol. Biol. 24:307-31(1994), but without limitations thereto.

In an exemplary embodiment of the present disclosure, the nucleic acid molecule of the present disclosure includes the nucleotide sequences of SEQ ID NOS: 22 to 32, the nucleotide sequences of SEQ ID NOS: 46 to 58, fragments thereof, or a combination thereof.

Provided according to an aspect of the present disclosure is a recombinant vector carrying the nucleic acid molecule of the present disclosure described above.

As used herein, the term "vector" refers to a means for expressing a target gene in a host cell and is intended to encompass a variety of vectors including: plasmid vectors; cosmid vectors; and viral vectors such as bacteriophage vectors, adenovirus vectors, retrovirus vectors, and adeno-associated virus vectors.

According to a preferable embodiment of the present disclosure, the nucleic acid molecule coding for the light chain variable domain and the nucleic acid molecule coding for the heavy chain variable domain are operatively linked to a promoter in the vector of the present disclosure.

As used herein, "operatively linked" means that an expression control sequence (e.g., a promoter, a signal sequence, or an array of transcriptional regulatory factors) and a nucleic acid of interest are linked so that the transcription and/or translation of the nucleic acid of interest can be governed by the control sequence.

The recombinant vector system of the present disclosure can be constructed by various methods known in the art. For concrete methods, reference may be made to Sambrook et al., Molecular Cloning, A Laboratory Manual, Cold Spring Harbor Laboratory Press (2001), which is incorporated in its entirety herein by reference.

The vector of the present disclosure may be typically constructed as a vector for cloning or expression. In addition, the vector of the present disclosure may be constructed with a prokaryotic cell or an eukaryotic cell serving as a host.

For example, when the vector of the present disclosure is an expression vector, with a eukaryotic cell serving as a host, advantage is taken of a promoter derived from the genome of a mammalian cell (e.g., metallothionein promoter, β-actin promoter, human hemoglobin promoter, and human muscle creatine promoter) or a promoter derived from mammalian viruses (e.g., adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of Moloney virus, promoter of Epstein-Barr virus (EBV), and promoter of Rous sarcoma virus (RSV)), with a polyadenylated sequence commonly employed as a transcription termination sequence in the vector.

The vector of the present disclosure may be fused with the other sequences to facilitate the purification of the antibody expressed therefrom. Examples of the fusion sequence include glutathione S-transferase (Pharmacia, USA), maltose binding protein (NEB, USA), FLAG (IBI, USA), and 6X His (hexahistidine; Quiagen, USA).

Since the protein expressed by the vector of the present disclosure is an antibody, the expressed antibodies can be easily purified through protein A column or the like even without additional sequences for purification.

Meanwhile, the expression vector of the present disclosure includes, as a selective marker, an antibiotic agent-resistant gene that is ordinarily used in the art, examples of which include resistant genes against ampicillin, gentamycin, carbenicillin, chloramphenicol, streptomycin, kanamycin, geneticin, neomycin, and tetracycline.

According to another aspect of the present disclosure, the present disclosure provides a host cell transformed with the recombinant vector.

So long as it is capable of performing continuous cloning and expression while stabilizing the vector of the present disclosure, any host cell known in the art may be used, and for example, examples of eukaryotic host cells suitable for the vector include monkey kidney cells 7 (COS7), NSO cells, SP2/0, Chinese hamster ovary (CHO) cells, W138, baby hamster kidney (BHK) cells, MDCK, myeloma cell lines, HuT 78 cells, and HEK-293, but are not limited thereto.

As used herein, the term "transformed", "transduced", or "transfected" refers to pertaining to the delivery or introduction of a foreign nucleic acid into a host cell. The "transformed", "transduced", or "transfected" cells are cells into which a foreign nucleic acid is transformed, transduced, or transfected. Within the scope of the transformed, transduced, or transfected cells, the cells themselves and progeny cells thereof obtained through passages fall.

Provided in accordance with still another aspect of the present disclosure is a pharmaceutical composition for the prevention or treatment of ischemic disease, stroke, kidney injury or disease, retinal neovascularization disorder, neurological disorder or disease, or a wound, the pharmaceutical composition comprising: (a) a pharmaceutically effective amount of the anti-c-Met antibody or antigen-binding fragment of the present disclosure; and (b) a pharmaceutically acceptable carrier.

According to an embodiment of the present disclosure, the kidney injury or disease is a fibrotic condition.

According to an embodiment of the present disclosure, the kidney injury or disease is selected from the group consisting of renal fibrosis, chronic kidney fibrosis, chronic nephropathy associated with diabetes, lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, and fibrosis associated with exposure to a toxin, an irritant, and a chemotherapeutic.

According to an embodiment of the present disclosure, the retinal neovascularization disorder is caused by one selected from the group consisting of macular degeneration, histoplasmosis, pathological myopia, angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous Candida endophthalmitis, extrapapillary hamartomas of the retinal pigmented epithelium, fundus flavimaculatus, idiopathic, macular hole, malignant melanoma, membranoproliferative glomerulonephritis, type II, metallic intraocular foreign body, morning glory disc syndrome, multiple evanescent white-dot syndrome (MEWDS), neovascularization at ora serrata, operating microscope burn, optic nerve head pits, photocoagulation, punctuate inner choroidopathy, rubella, sarcoidosis, serpiginous or geographic choroiditis, subretinal fluid drainage, tilted disc syndrome, taxoplasma retinochoroiditis, tuberculosis, Vogt-Koyanagi-Harada syndrome, diabetic retinopathy, non-diabetic retinopathy, branch vein occlusion, central retinal vein occlusion, retinopathy in premature infants, rubeosis iridis, neovascular glaucoma, perifoveal telangiectasis, sickle cell retinopathy, Eale's disease, retinal vasculitis, Von Hippel Linau disease, radiation retinopathy, retinal cryoinjury, retinitis pigmentosa, retinochoroidal coloboma, corneal neovascularization due to herpes simplex keratitis, corneal ulcers, keratoplasty, pterigyia, and trauma.

According to an embodiment of the present disclosure, the retinal neovascularization disorder is choroidal neovascularization.

According to an embodiment, the neurological disorder or disease may be selected from the group consisting of traumatic brain injury, stroke, cerebral aneurism, spinal cord injury, Parkinson's disease, amyotrophic lateral sclerosis, Alzheimer's disease, diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, ophthalmoplegia, and retina or optic nerve damage.

According to an embodiment of the present disclosure, the wound is a mechanical, chemical, microbial, or thermal wound.

According to an embodiment of the present disclosure, the wound may be selected from the group consisting of incision, laceration, abrasion, puncture wound, penetration wound, and gunshot wound.

According to an embodiment of the present disclosure, the wound is a skin wound.

A pharmaceutically acceptable carrier contained in the pharmaceutical composition of the present disclosure is one typically used in drug preparation and includes, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, cyclodextrin and mineral oil. The pharmaceutical composition of the present disclosure may further include a lubricant, a humectant, a sweetening agent, a favoring agent, an emulsifier, a suspending agent, and a preserving agent besides the components above. A suitable pharmaceutically acceptable carrier and a formulation are described in Remington's Pharmaceutical Sciences (19th ed., 1995).

The pharmaceutical composition of the present disclosure may be administered orally or parentally, for example, by intravenous injection, subcutaneous injection, intramuscular injection, intraperitoneal injection, topical administration, intranasal administration, intrapulmonary administration, rectal administration, or the like.

According to an embodiment, the administration may be conducted intravenously, intravitreally, intrathecally, parenterally, subcutaneously, transdermally, or by infusion.

The appropriate dose of the pharmaceutical composition of the present disclosure varies depending on factors, such as a formulating method, a manner of administration, patient's age, body weight, sex, morbidity, food, a time of administration, a route of administration, an excretion rate, and response sensitivity. An ordinarily skilled practitioner can easily determine and prescribe the dose that is effective for the desired treatment or prevention. According to a preferable embodiment of the present disclosure, the daily dose of the pharmaceutical composition of the present disclosure is 0.0001-100 mg/kg. As used herein, the term "pharmaceutically effective amount" refers to an amount sufficient to treat an ischemic disease, stroke, a kidney injury or disease, a retinal neovascularization disorder, neurological disorder or disease, or a wound The pharmaceutical composition of the present disclosure may be formulated into a unit dosage form or may be prepared in a multi-dose container by using a pharmaceutically acceptable carrier and/or excipient according to a method that is easily conducted by a person having an ordinary skill in the art to which the present invention pertains. Here, the dosage form may be a solution in an oily or aqueous medium, a suspension, an emulsion, an extract, a pulvis, a suppository, a powder, granules, a tablet, or a capsule, and may further include a dispersant or a stabilizer.

The pharmaceutical composition of the present disclosure employs the above-mentioned anti-c-Met antibody or antigen-binding fragment of the present disclosure as an active ingredient. Thus, the common contents therebetween will be omitted from the description in order to avoid excessive complexities.

Another aspect of the present disclosure provides a method for treatment of an ischemic disease, stroke, a kidney injury or disease, a retinal neovascularization disorder, neurological disorder or disease, or a wound, comprising administering to a subject a pharmaceutical composition comprising the anti-c-Met antibody or antigen-binding fragment as an active ingredient.

As used herein, the term "administration" or "administer" refers to the direct application of a therapeutically effective amount of the composition of the present disclosure to a subject (i.e., an object) in need of the composition, thereby forming the same amount thereof in the body of the subject.

The term "therapeutically effective amount" of the composition refers to the content of the composition, which is sufficient to provide a therapeutic or preventive effect to a subject to be administered, and thus the term has a meaning including "preventively effective amount". As used herein, the term "subject" includes, but is not limited to, human, mouse, rat, guinea pig, dog, cat, horse, cow, pig, monkey, chimpanzee, beaver, or rhesus monkey. Specifically, the subject of the present disclosure is human.

Since the treatment method of the present disclosure includes the step of administering the pharmaceutical composition according to an aspect of the present disclosure, the overlapping contents therebetween are omitted to avoid excessive complexities of the description.

Advantageous Effects

Features and advantages of the present disclosure are as follows:

(a) The present disclosure provides an anti-c-Met antibody or an antigen-binding fragment thereof, a nucleic acid coding therefor, a recombinant vector carrying the recombinant vector, and a host cell transformed therewith, wherein the anti-c-Met antibody or the antigen-binding fragment is endowed with improved stability by amino acid substitution at specific positions of the prototype antibody and CDR grafting.

(b) The anti-c-Met antibody or antigen-binding fragment with improved stability according to the present disclosure is of excellent productivity and biopotency and reduced immunogenicity, compared to its prototype antibody 1E4.

(c) Therefore, the anti-c-Met antibody or antigen-binding fragment of the present disclosure exhibits a reduced production cost, retains the efficiency, and decrease in side effect in view of the development of anti-c-Met antibodies.

BRIEF DESCRIPTION OF THE DRAWINGS

Figure 2H:
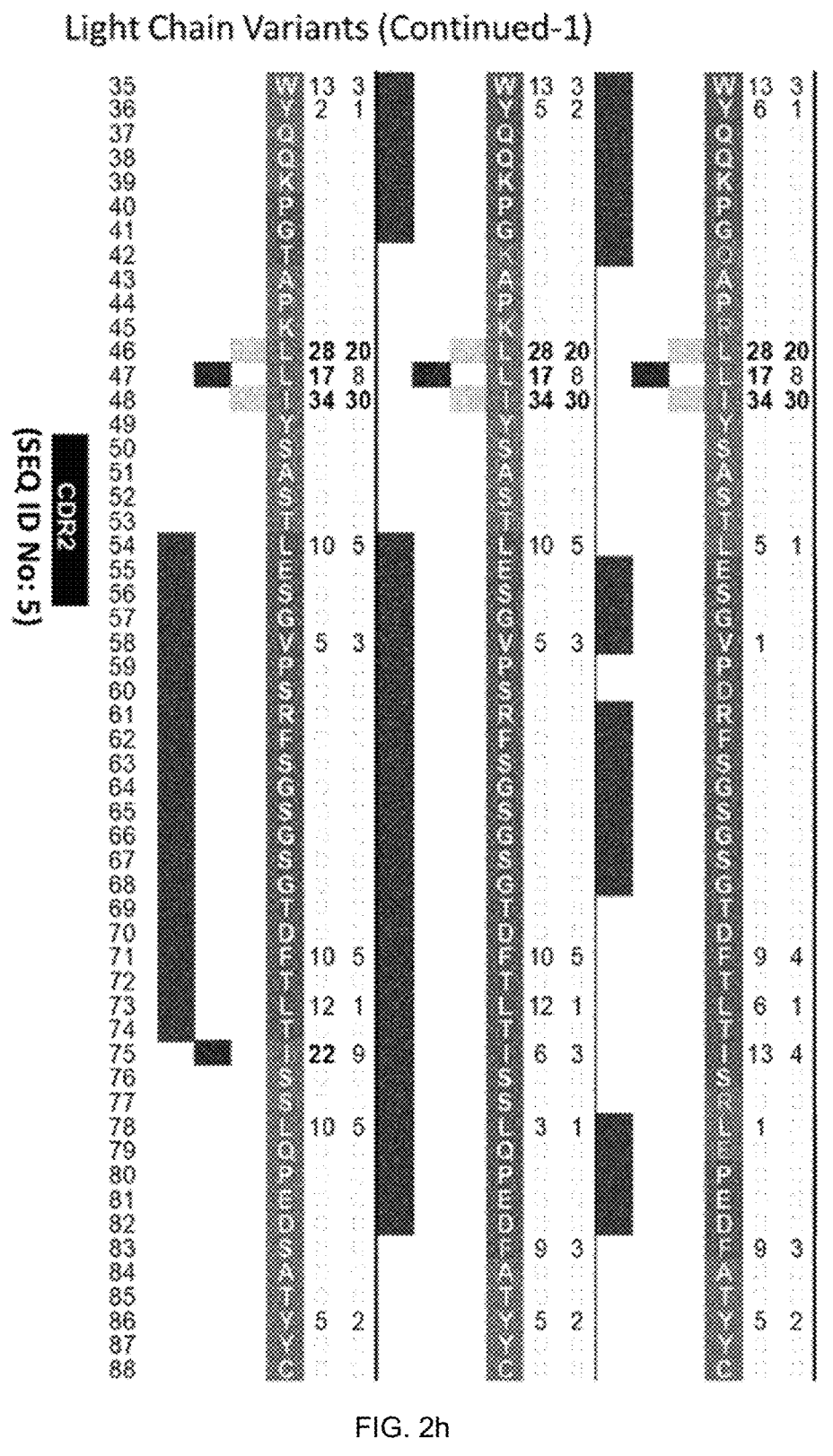

FIGS. 2a, 2b, 2c, 2d, 2e, 2f, 2g, 2h, 2i, 2j, 2k and 2l are views showing in silico assay for immunogenicity of heavy chain variable domains (2a to 2f) and light chain variable domains (2g to 2l) to select candidate sequences for CDR grafting of anti-c-Met antibodies.

FIGS. 3a, 3b, 3c, 3d and 3e are views of alignments between the reference anti-c-Met antibody, and the heavy chain variable domain candidate sequences (3a-3c) and light chain variable domain candidate sequences (3d-3e) for CDR grafting. The amino acid sequences of the antibodies are numbered according to the Kabat system, with different amino acid residues expressed in gray.

FIGS. 7a, 7b and 7c are in silico alignments of the heavy chain constant domain sequences (7a and 7b) and the light chain constant domain sequence (7c) of 1E4 with the human germline sequence.

DETAILED DESCRIPTION

Figure 1A:
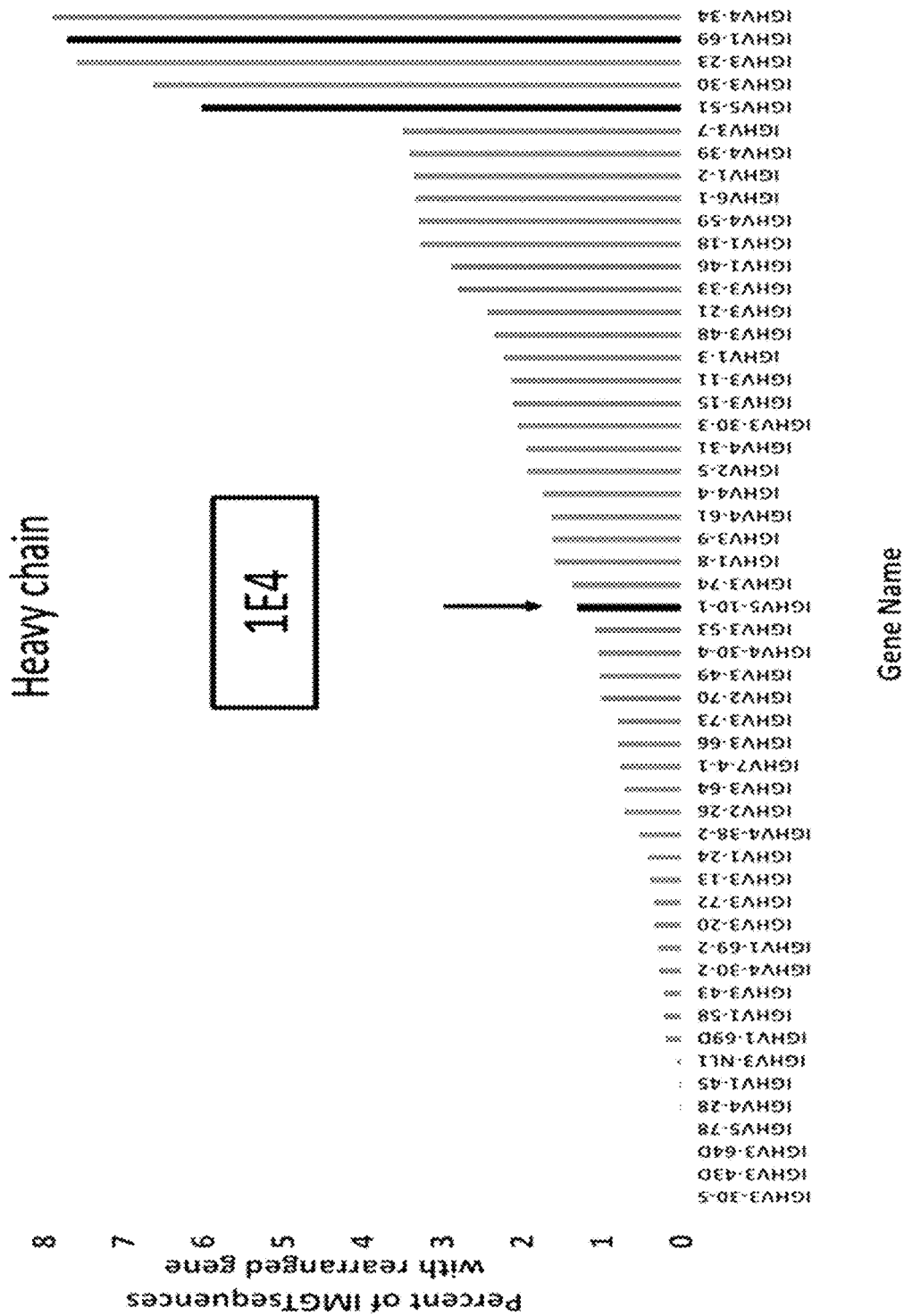
FIGS. 1a and 1b are views showing surrogate assay for stability of variable domains against occurrence frequencies of individual germline sequences to select candidate sequences for CDR grafting of anti-c-Met antibodies.

Hereinafter, the present disclosure will be described in more detail through examples. The following examples are for illustrative purposes only and it will be apparent to those of ordinary skill in the related art that the scope of this disclosure is not limited by the examples.

EXAMPLES

Throughout the description, the term "%" used to express the concentration of a specific material, unless otherwise particularly stated, refers to (wt/wt) % for solid/solid, (wt/vol) % for solid/liquid, and (vol/vol) % for liquid/liquid.

Example 1: Substitution of Constant Domain in 1E4 Antibody and Biopotency Thereof In order to enhance the structural stability of the IgG1-based anti-c-Met antibody 1E4, which is disclosed in WO2016/021864A1 and WO2017/135791A1, both issued to the present inventors, while preserving anti-c-Met antibody characteristics, complementarity determining regions (CDRs) of the conventional antibody was grafted into a framework region more stable than that of the conventional antibody by using a CDR grafting method. Prior to CDR grafting, ABZENA, UK was requested to compare sequences of the heavy chain and light chain constant domain in 1E4 with human germline sequences in silico.

As a result of analysis, the heavy chain constant domain was observed to coincide with G1 m (3) allotype except for the lysine residue (K) of CH1 domain (FIGS. 7a and 7b). The lysine (K) residue is rarely observed in G1m (17,1) allotype in the human population and includes the possibility of potential immunogenicity (Lefranc and Lefranc, 2012). In consideration of in vivo stability, therefore, the residue was substituted with arginine (R) residue so as to perfectly match the heavy chain constant domain with G1 m (3) allotype. For the light chain constant domain, serine (S) residue at position 1 in the data was substituted with threonine (T) residue to avoid potential immunogenicity. As a result, the light chain constant domain was mutated to coincide with the human germline sequence Km3 allotype (FIG. 7c).

The 1E4 antibody variant including the constant domain where the residues were substituted was designated VH0/Vk0. In addition, a HUVEC migration assay was performed to examine the biopotency of VH0/Vk0 at an in vitro level. The assay data indicated that like the positive control hepatocyte growth factor (HGF), IE4 and VH0/Vk0 both promoted at a concentration of 90 ng/ml the migration of HUVEC. Quantitatively, 1E4 and VH0/Vk0 similarly promoted cell migration to similar extents by 158% and 161%, respectively, compared to the negative control. From the results, it was confirmed that the variant still retained the biopotency in spite of the modification of the constant domain. In addition, the modification by which the constant domain perfectly coincides with the human germline sequence is expected to improve in vivo stability (immunogenicity, etc.) and safety (half-life, etc.) by reducing immunogenicity and neutralization (Reference: Lefranc, M.-P., and Lefranc, G. (2012). Human Gm, Km and Am allotypes and their molecular characterization: a remarkable demonstration of polymorphism. In immunogenetics (F. Christiansen and B. Tait, Eds.), Chap. 34. Humana Press, Springer, New York. *Methods Mol Biol.* 882, 635-680).

(VH), and the human germline sequence IGHV5-10-1*01 on which the 1E4 antibody is based, and between IGKV1-39*01 and IGKV3-20*01, which are framework regions of the light chain variable domain (Vk), and the human germline sequence IGKV1-9*01 on which 1E4 antibody is based. (Table 1).

TABLE 1

Sequence Homology between VH and Vk of anti-c-Met antibody(1E4), and heavy chain and light chain variable domains of human antibody

|  | Heavy chain | | Light chain (Kappa chain) | |
| --- | --- | --- | --- | --- |
|  | Human V region germline segment | Human J region germline segment | Human V region germline segment | Human J region germline segment |
| Homology to closest matching human germline | IGHV5-10-1*01 (86.7%) | IGHJ4*01 (92.9%) | IGKV1-9*01 (89.5%) | IGKJ4*01 (100%) |
| Homology to germlines selected for humanization | IGHV5-51*01 (82.7%) IGHV1-69*02 (62.2%) | IGHJ4*01 (92.9%) IGHJ4*01 (92.9%) | IGKV1-39*01 (87.4%) IGKV3-20*01 (67.7%) | IGKJ4*01 (100%) IGKJ4*01 (100%) |

* IGHV5-51*01: IGHV: heavy chain variable
1) IGHV 5: Gene group
2) 51: Gene localization (Gene locus)
3) *01: Reference sequence
* IGHV1-69*02
IGHV: heavy chain variable
1) IGHV 1: Gene group
2) 69: Gene localization (Gene locus)
3) *02: Sequence variant
* IGKV1-39*01
IGKV: kappa light chain variable
1) IGHV 1: Gene group
2) 39: Gene localization
3) *01: Reference sequence
* IGKV3-20*01
IGKV: kappa light chain variable
1) IGHV 3: Gene group
2) 20: Gene localization
3) *01: Reference sequence

Example 2: Searching for Optimal Framework for CDR Grafting

In relation to 1E4, which is the IgG1-based anti-c-Met antibody disclosed in WO2016/021864A1 and WO2017/135791A1, both issued to the present inventors, an improvement was made of structural stability while preserving the anti-c-Met antibody characteristics. In this regard, CDR grafting was utilized to graft the complementarity determining regions (CDRs) of the conventional antibody to a framework region more stable than that of the conventional antibody.

First, an optimal framework region was selected. To this end, heavy chain variable domain (hereinafter referred to as "VH") and light chain variable domain (hereinafter referred to as "Vk") amino acid sequences were compared with a database of human germline variable (V) and junction (J) segment sequences to examine sequence homologies between the heavy chain and light chain variable domains of human antibodies and the heavy chain variable domain (VH) and light chain variable domain (Vk) of the anti-c-Met antibody 1E4.

As a result, a sequence homology of 60% or more was detected between IGHV5-51*01 and IGHV1-69*02, which are framework regions of the heavy chain variable domain (VH), and the human germline sequence IGHV5-10-1*01 on which the 1E4 antibody is based, and between IGKV1-39*01 and IGKV3-20*01, which are framework regions of the light chain variable domain (Vk), and the human germline sequence IGKV1-9*01 on which 1E4 antibody is based.

Next, the framework candidates primarily adopted on the basis of the sequence homology were further divided with reference to the stability of human germline sequences known previously. In this regard, analysis was conducted with reference to surrogates for the stability of variable domains against occurrence frequencies of individual germline sequences. As a result, the heavy chain variable domains IGHV5-51*01 and IGHV1-69*02, and the light chain variable domains IGKV1-39*01 and IGKV3-20*01 were detected to have high occurrence frequencies compared to 1E4 antibody (FIG. 1).

Figure 1B:
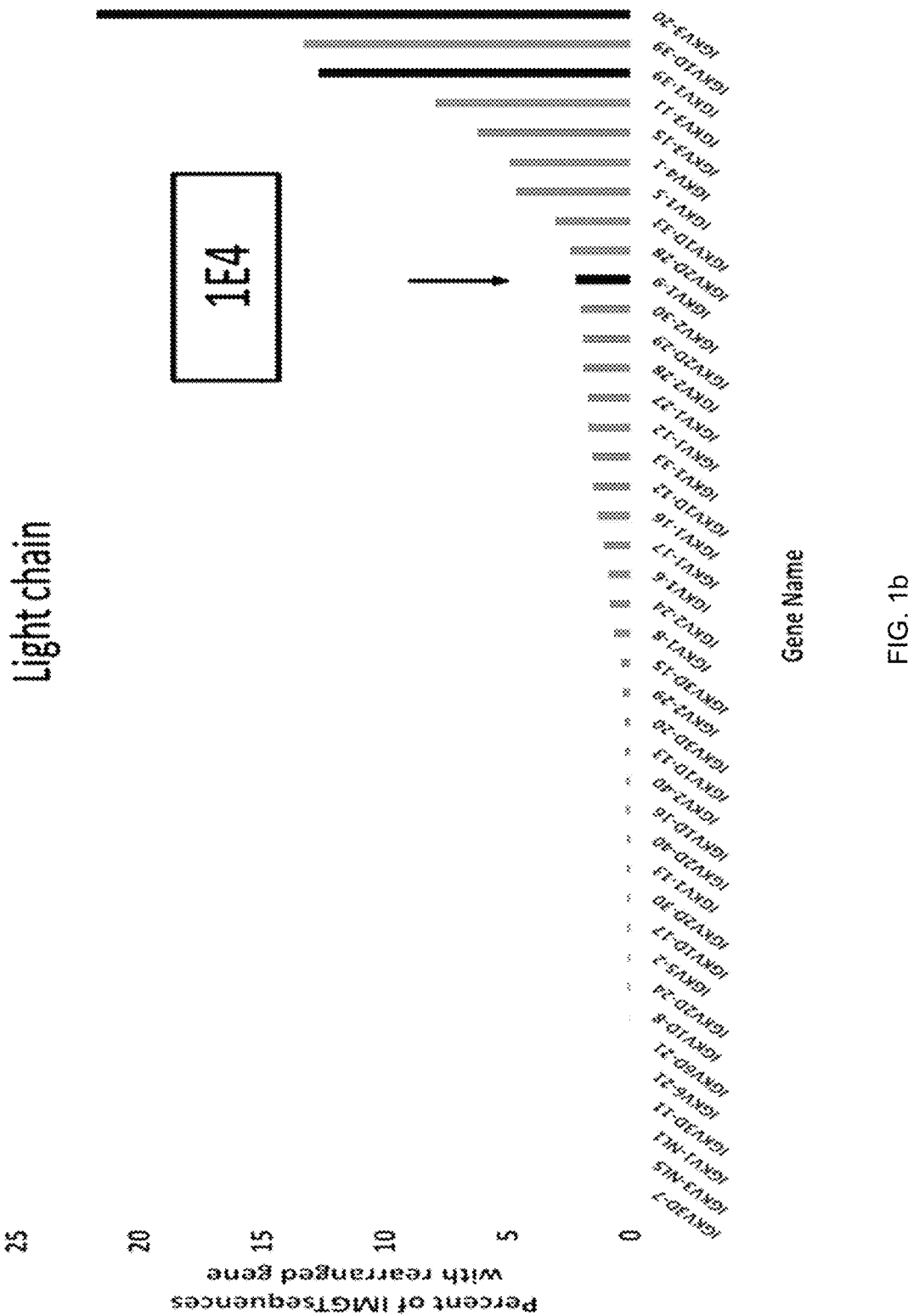
Figure 2A:
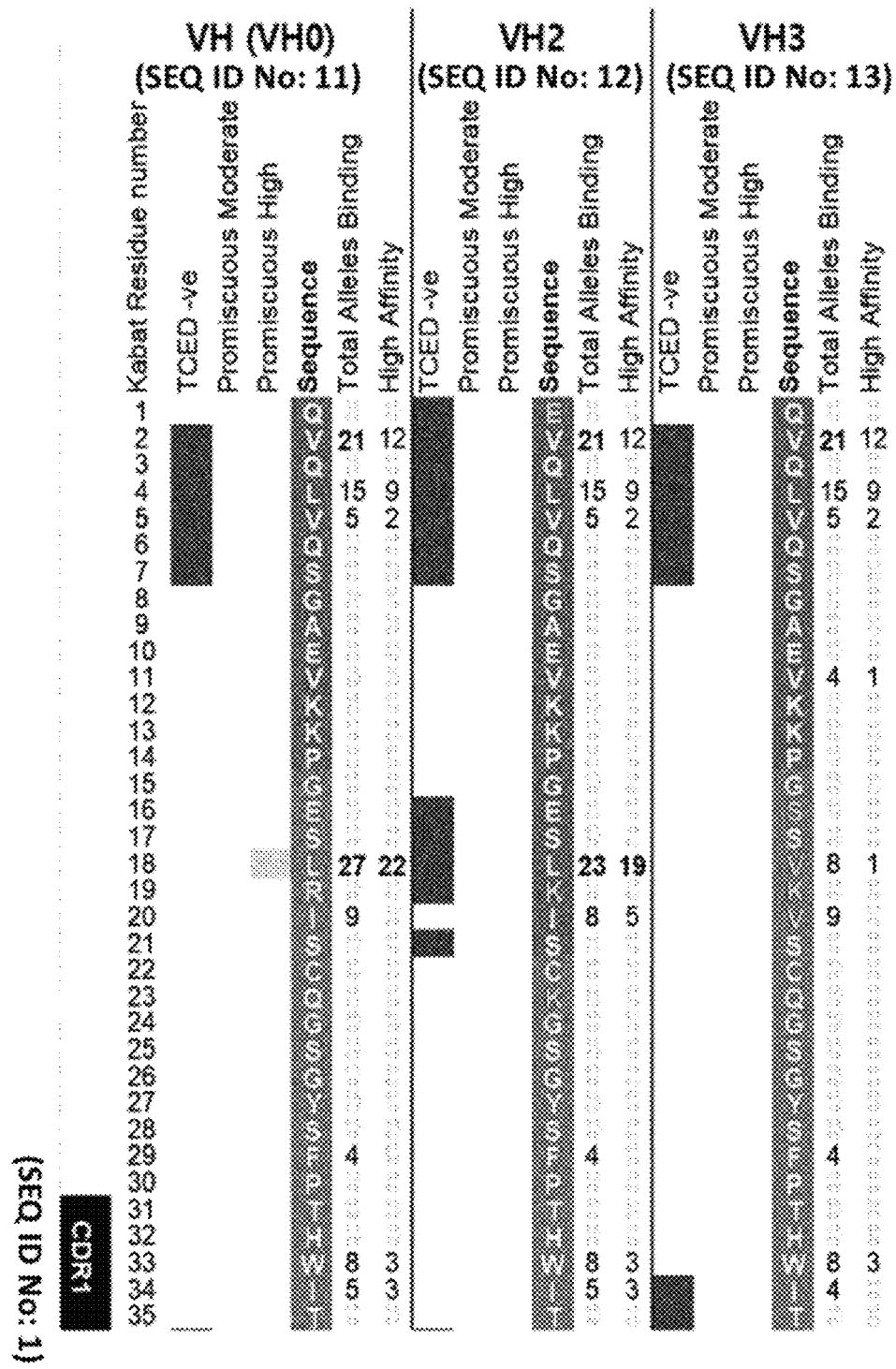
Figure 2B:
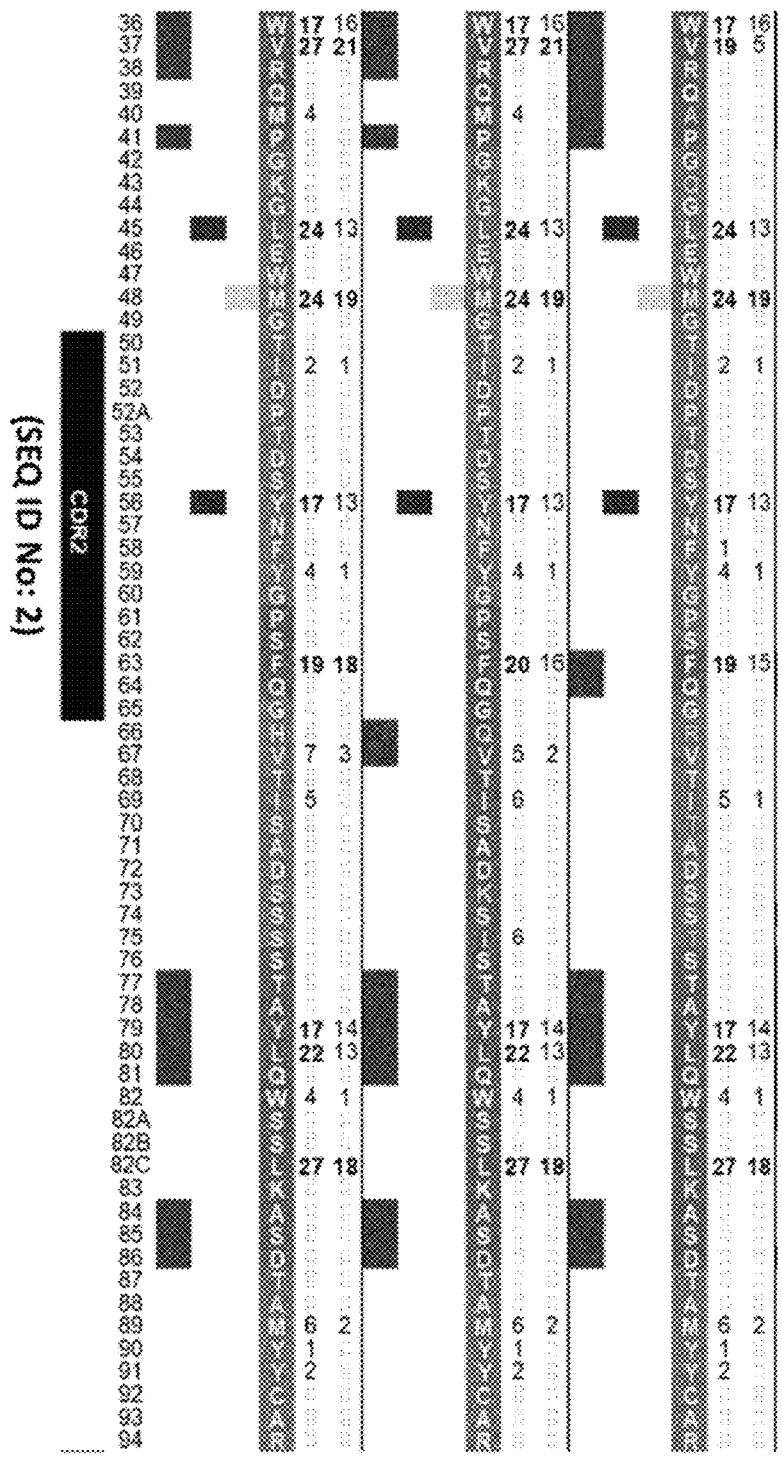
Figure 2C:
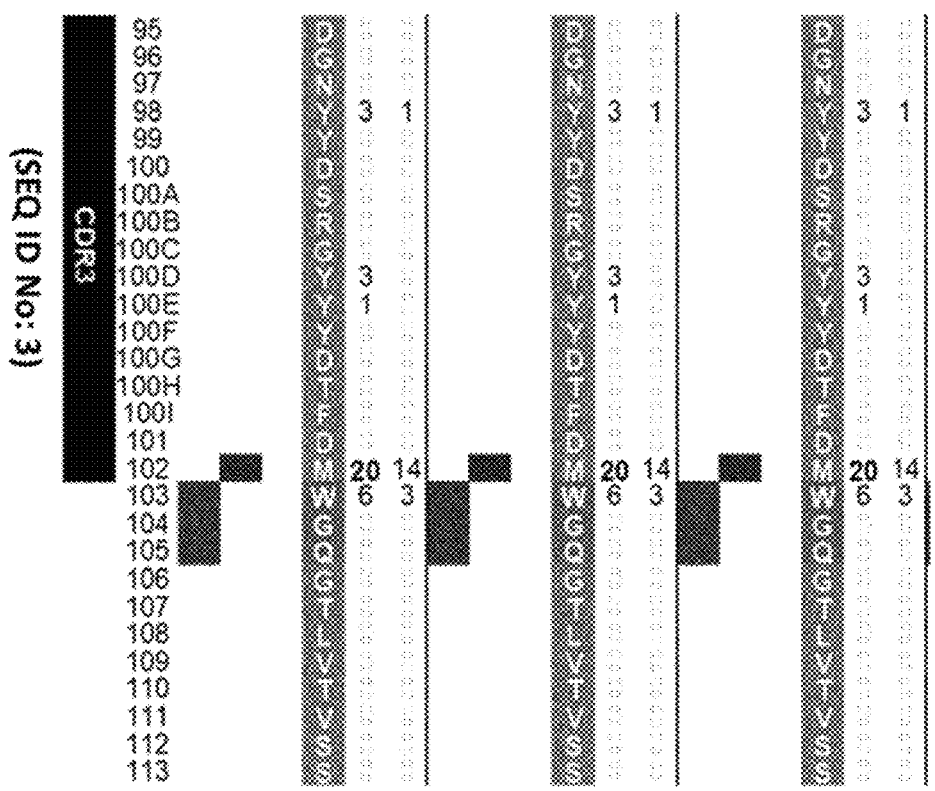
Figure 2D:
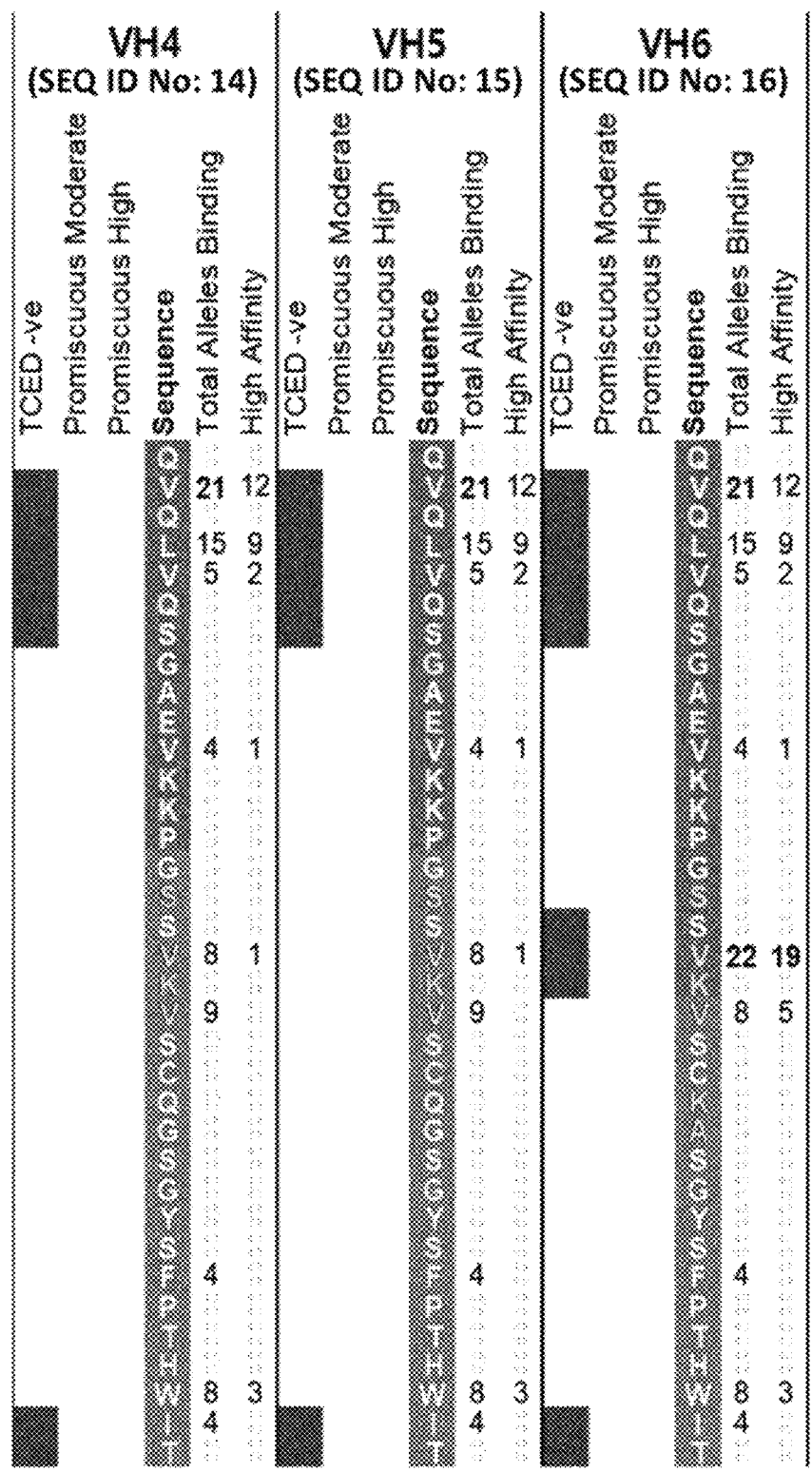
Figure 2E:
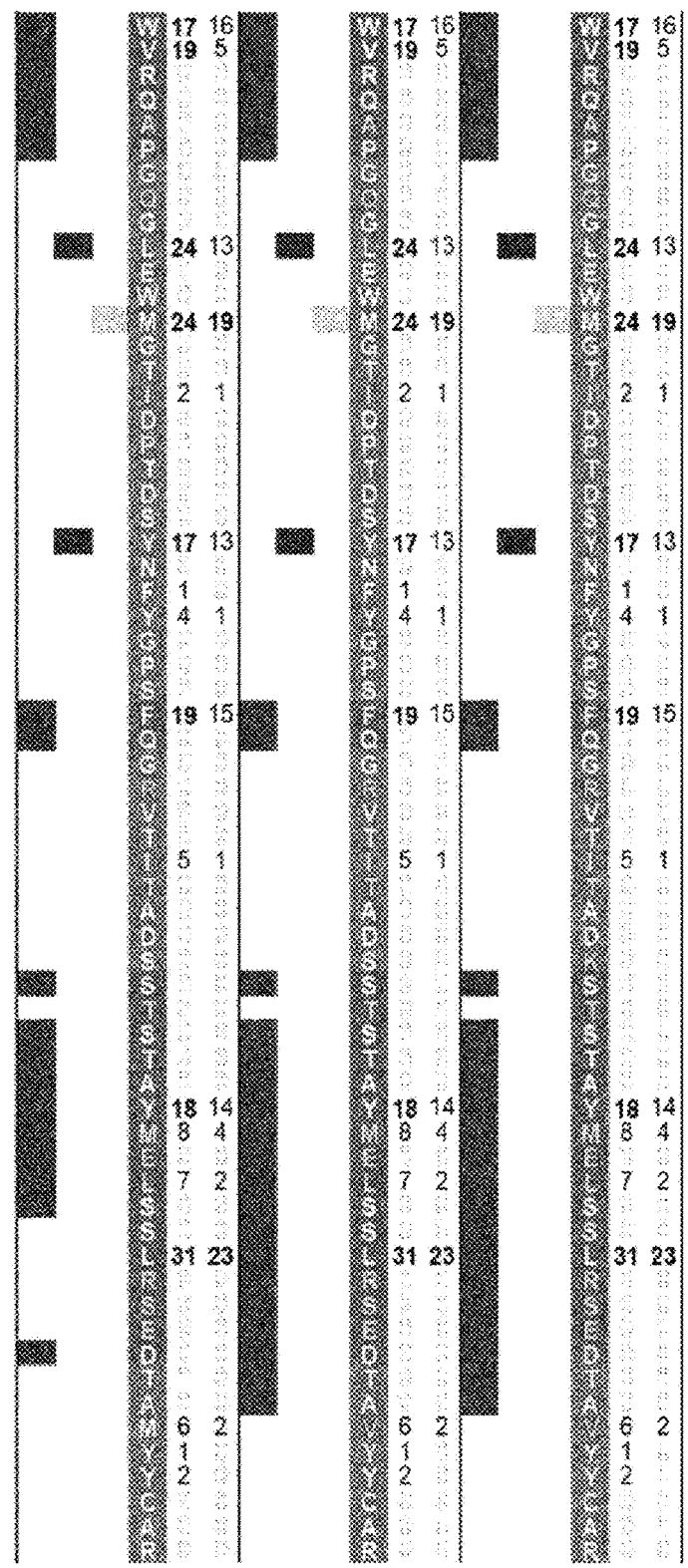
Figure 2F:
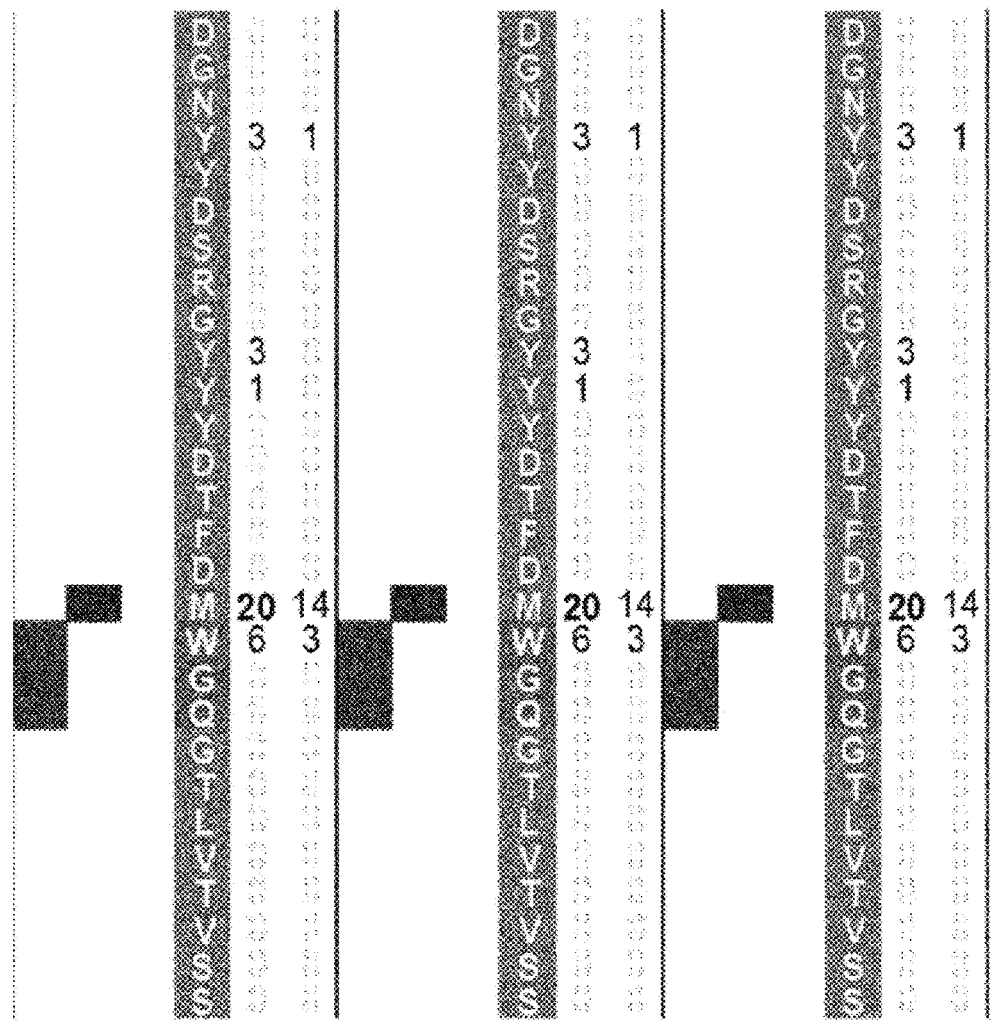
Figure 2G:
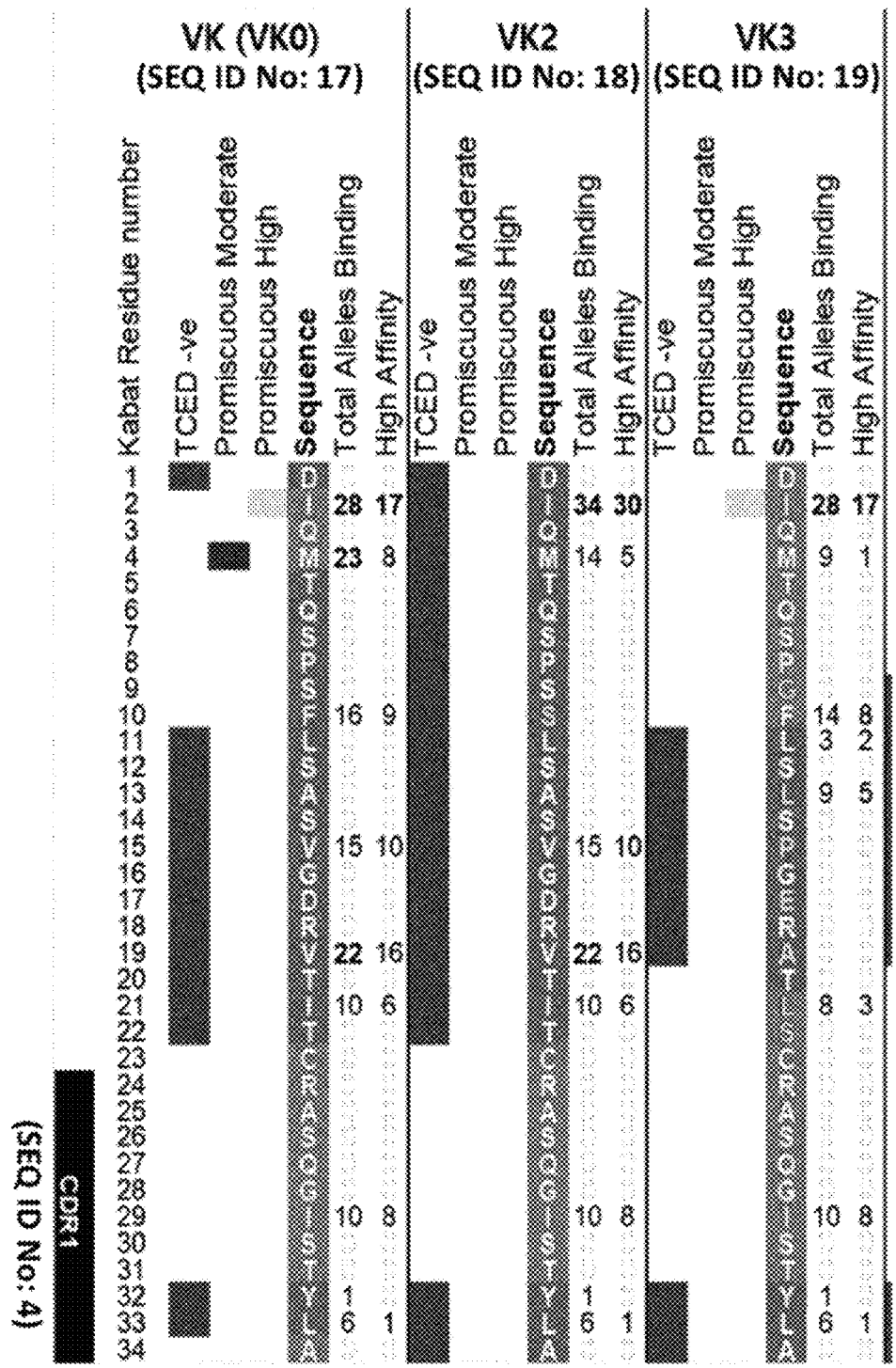
Figure 2I:
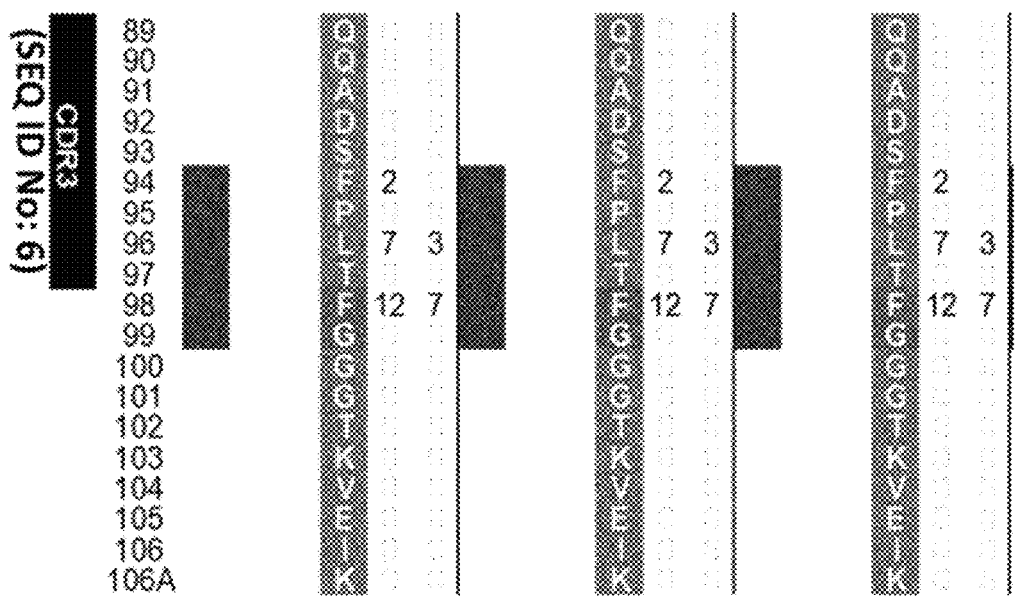
Figure 2J:
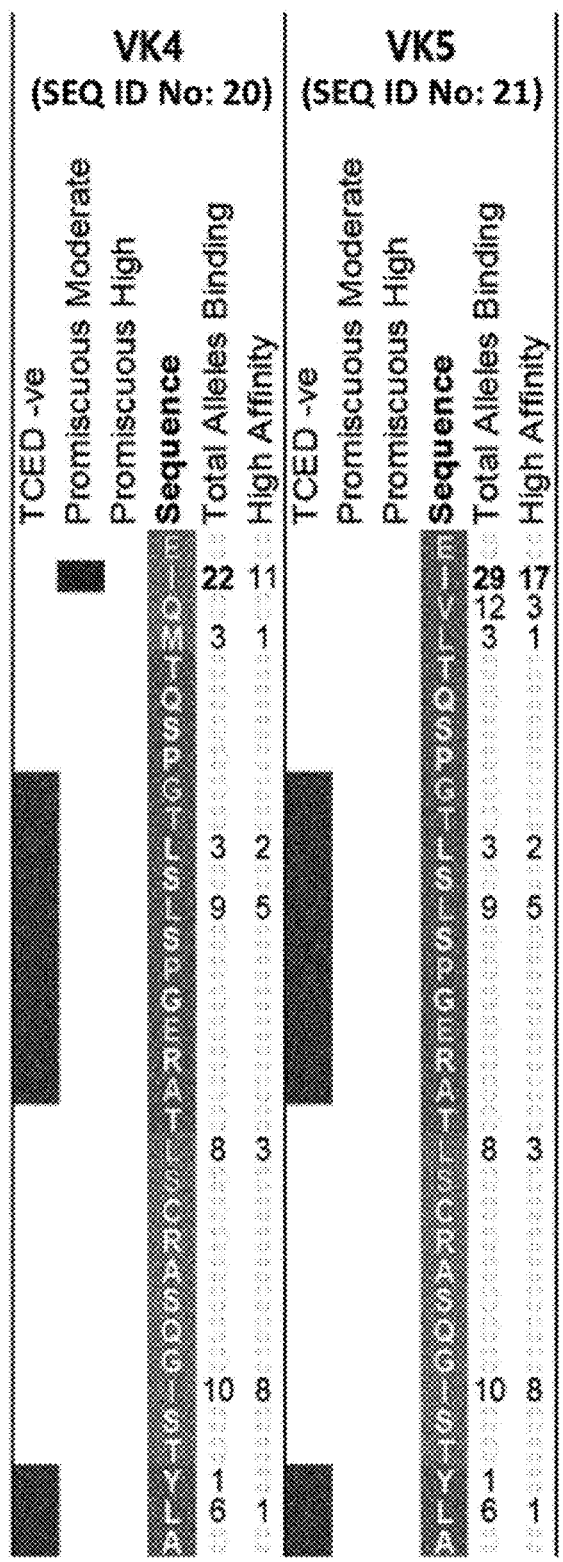
Figure 2K:
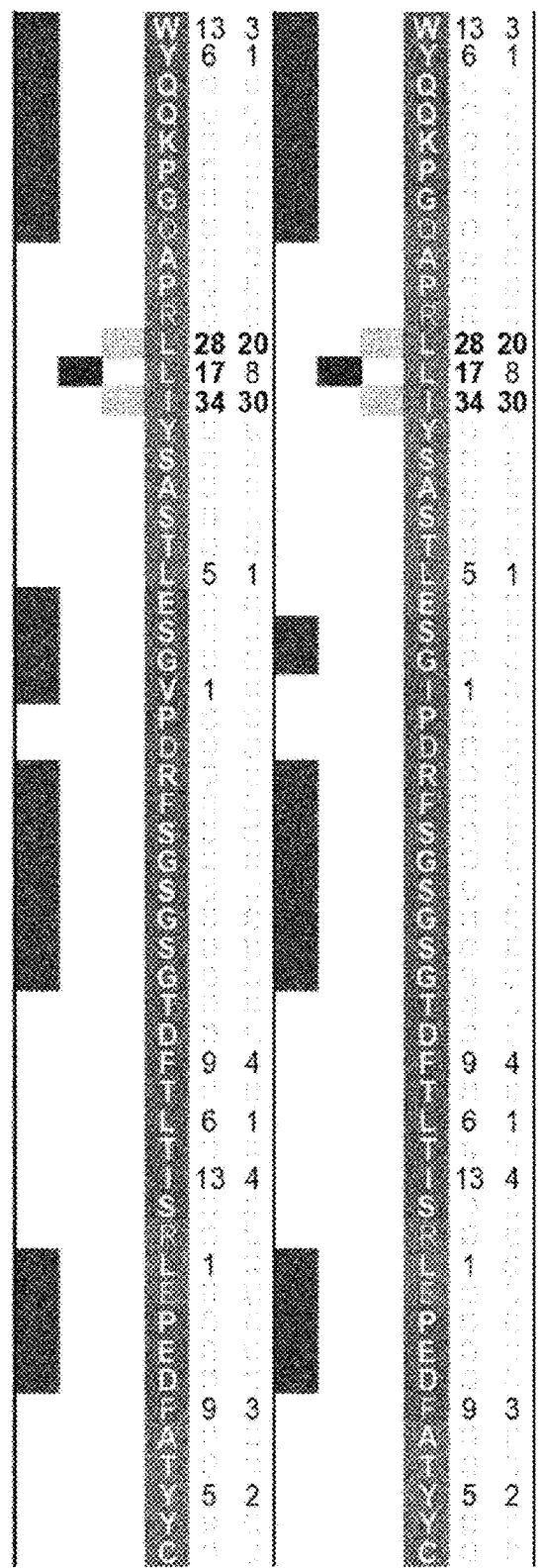
Figure 2I:
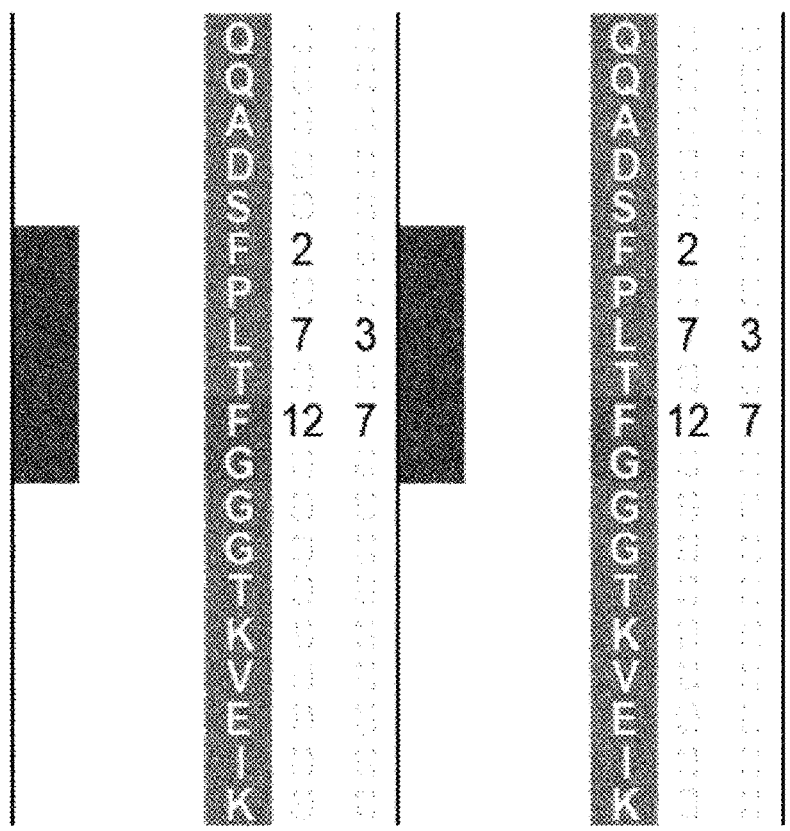

Based on the data of Table 1 and FIG. 1, the heavy chain variable domains IGHV5-51*01 and IGHV1-69*02 and the light chain variable domains IGKV1-39*01 and IGKV3-20*01, which had a sequence homology of 60% or more with the germline sequences and are more stable than the variable domains of 1E4 antibody, were selected as final candidate human germline sequences of the frameworks for CDR grafting of the anti-c-Met antibody.

Example 3: Establishment of Final Heavy Chain and Light Chain Variable Domain Sequences Through in Silico Assay for Immunogenicity Complementarity-determining regions (CDRs) of 1E4 antibody were grafted to the selected frameworks of Example 2 and the amino acid residues identified to play an important role in preserving antigen-antibody binding affinity were subjected to back-mutation, followed by in silico assaying for immunogenicity with the aid of iTope™ and TCED™ of ABZENA, UK (Perry et al. 2008; Bryson et al. 2010).

In brief, scanning analysis was performed on nine peptides of the framework candidate sequences selected in Example 2 while extending them by one amino acid per scanning. According to the analysis technique, the amino acid residues of the antibody variable domain sequences were numbered using the Kabat numbering system. Regions containing peptides with potential immunogenicity were expressed in the "iTope™" column. Promiscuous high affinity MHC class II binding peptides were represented in red while promiscuous moderate MHC class II binding peptides were represented in yellow. The "TCED™ (T Cell Epitope Database)" column represents in green amino acid regions analyzed to be negative peptides as compared to the T cell epitope data, and emphasized in red other amino acid residues present in the candidate variable domain sequences based on the variable domain sequences of VH0/Vk0 (FIG. 2).

As a result of the analysis, peptide sequences predicted to be MHC class II ligands of various promiscuous high/moderate affinities were found in the constant domain modified antibodies (VH0/Vk0) sharing the original variable domain of the anti-c-Met antibody 1E4 developed by the present inventors as well as in other modified sequences. However, the peptide sequences (epitopes) were inferred to cause poor immune responses due to T cell tolerance because they are known to be included in the human germline sequences. Likewise, the promiscuous moderate/high epitopes which were identified to be T cell negative peptides as analyzed by TCED™ were also determined to be low in the risk of immunogenicity. Peptide sequences expected to be non-germline promiscuous high and moderate affinity MHC class II binding ligands which are not included in human germline sequences were observed in some of the candidate sequences, but were, for the most part, removed by a humanization design process. For amino acid residues that were somewhat likely to cause immunogenicity, but associated with CDR (e.g., Vk CDR2), CDR grafting was performed without additional modification in order to preserve the binding affinity of the antibody. By doing this, final candidate heavy chain and light chain variable domain sequences that retained CDR sequences with the potential risk of immunogenicity minimized were secured in silico.

For the heavy chain variable domain, one IGHV5-51*01-based candidate sequence (code name: VH2) and four IGHV1-69*02-derived candidate sequences (code names: VH3, VH4, VH5, and VH6) were designed. For the light chain variable domain, one IGKV1-39*01-based candidate sequence (code name: Vk2) and three IGKV3-20*01-based candidate sequences (code name: Vk3, Vk4, and Vk5) were designed. These sequences are given in Table 2 and FIG. 3. Individual amino acid residues were numbered according to the Kabat system, with emphasis given to CDRs in blue and to amino acid residues different from those of the conventional antibody sequence in red in each candidate variable domain sequence (FIG. 3).

TABLE 2

Candidate sequence of heavy chain and light chain variable domains for CDR grafting

| heavy chain variable domain candidate sequence | | | light chain variable domain candidate sequence | | |
|---|---|---|---|---|---|
| Germline | Code name | SEQ ID NO: | Germline | Code name | SEQ ID NO: |
| IGHV5-10-01 | VH0 (1E4) | 11 | IGKV1-9 | Vk0 (1E4) | 17 |
| IGHV5-51*01 | VH2 | 12 | IGKV1-39*01 | Vk2 | 18 |
| IGHV1-69*02 | VH3 | 13 | IGKV3-20*01 | Vk3 | 19 |
|  | VH4 | 14 |  | Vk4 | 20 |
|  | VH5 | 15 |  | Vk5 | 21 |
|  | VH6 | 16 |  |  |  |

Example 4: IgG Expression and Purification of Candidate Anti-c-Met Antibody Variants A total of 30 combinations of candidate anti-c-Met antibody variants including the heavy chain and light chain variable domain amino acid sequences selected in Example 3 and the heavy chain and variable domain amino acid sequences (VH0 and Vk0) of 1E4 antibody was designed.

In order to express anti-c-Met antibody variants into IgG structures in the full antibody form, heavy chain and light chain expression vectors in which the heavy chain and light chain constant domains selected in Example 1 are combined with candidate variable domains were constructed using the pANT™ vector system of ABZENA. The antibody expression recombinant vectors were transfected into HEK 293 EBNA adherent cells (LGC Standards, Teddington, UK) by a polyethylenimine transfection method. After nine days of culturing, the cell supernatants (media) were collected. The collected supernatants were analyzed using IgG1 Quantitation ELISA to quantify antibody levels therein. Combinations and expression levels of c-Met antibody variants are summarized in Table 3, below.

Four candidate antibodies (VH0/Vk3, VH0/Vk4, VH0/Vk5, and VH3/Vk0) which were not expressed at all and five candidate antibodies (VH2/Vk3, VH2/Vk4, VH3/Vk3, VH3/Vk4, and VH3/Vk5) which exhibited an expression level of 1.5 pg/ml or

TABLE 3

Combinations and Expression Levels (μg/ml) of candidate anti-c-Met antibody variants

|  | VH0 | VH2 | VH3 | VH4 | VH5 | VH6 |
|---|---|---|---|---|---|---|
| Vk0 | 37.1 | 31.9 | Not Expressed | 22.4 | 21.6 | 30.2 |
| Vk2 | 32.4 | 21.1 | 17.2 | 49.7 | 46.4 | 40.5 |
| Vk3 | Not Expressed | 0.9 | 0.3 | 5.3 | 5.8 | 7.4 |
| Vk4 | Not Expressed | 1.3 | 0.5 | 6.7 | 3.4 | 7.9 |
| Vk5 | Not Expressed | 3.1 | 1.4 | 16.5 | 10.3 | 14.7 |

Figure 4:
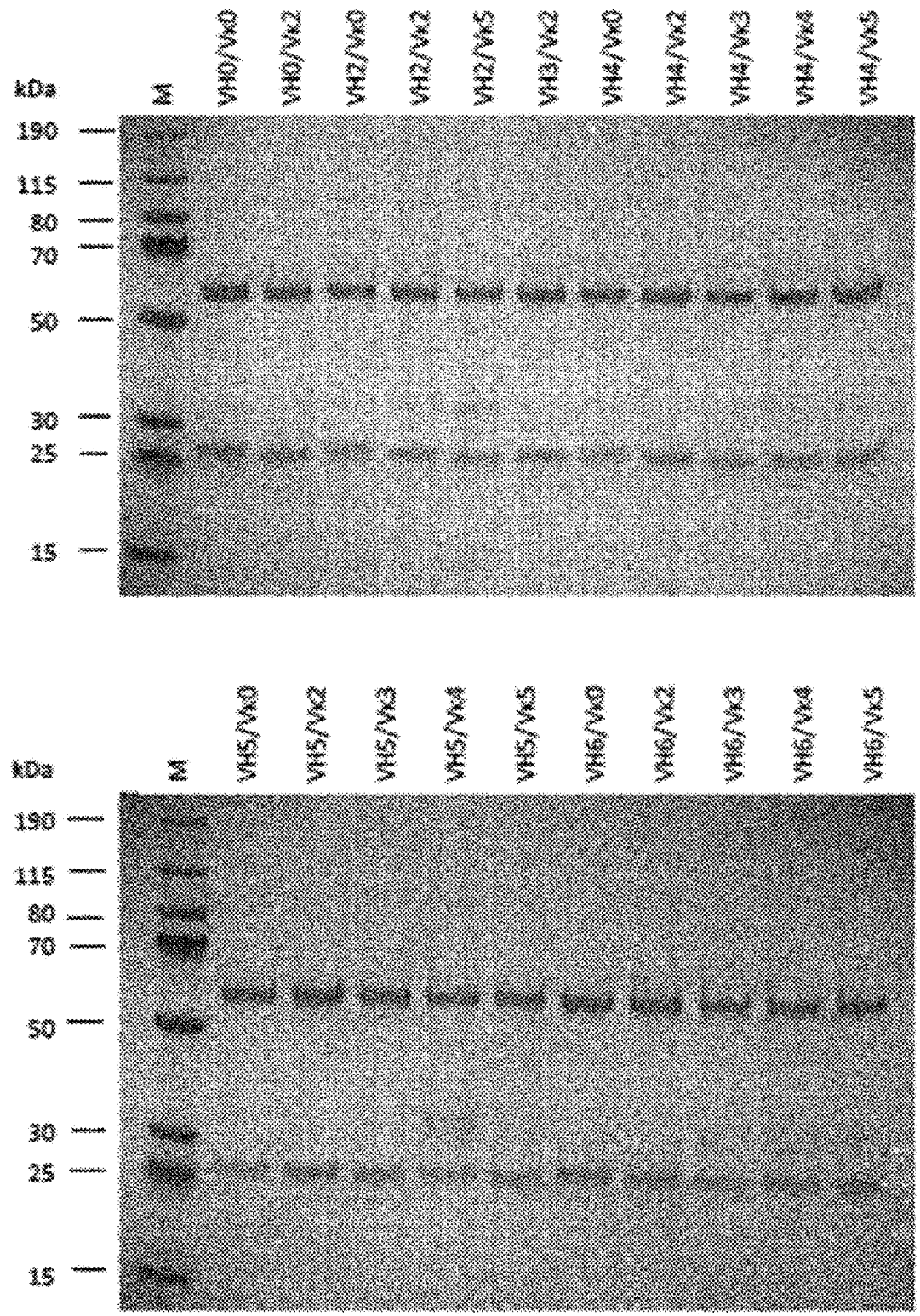
FIG. 4 shows SDS-PAGE results of the 21 candidate antibodies selected in the present disclosure.
Figure 5A:
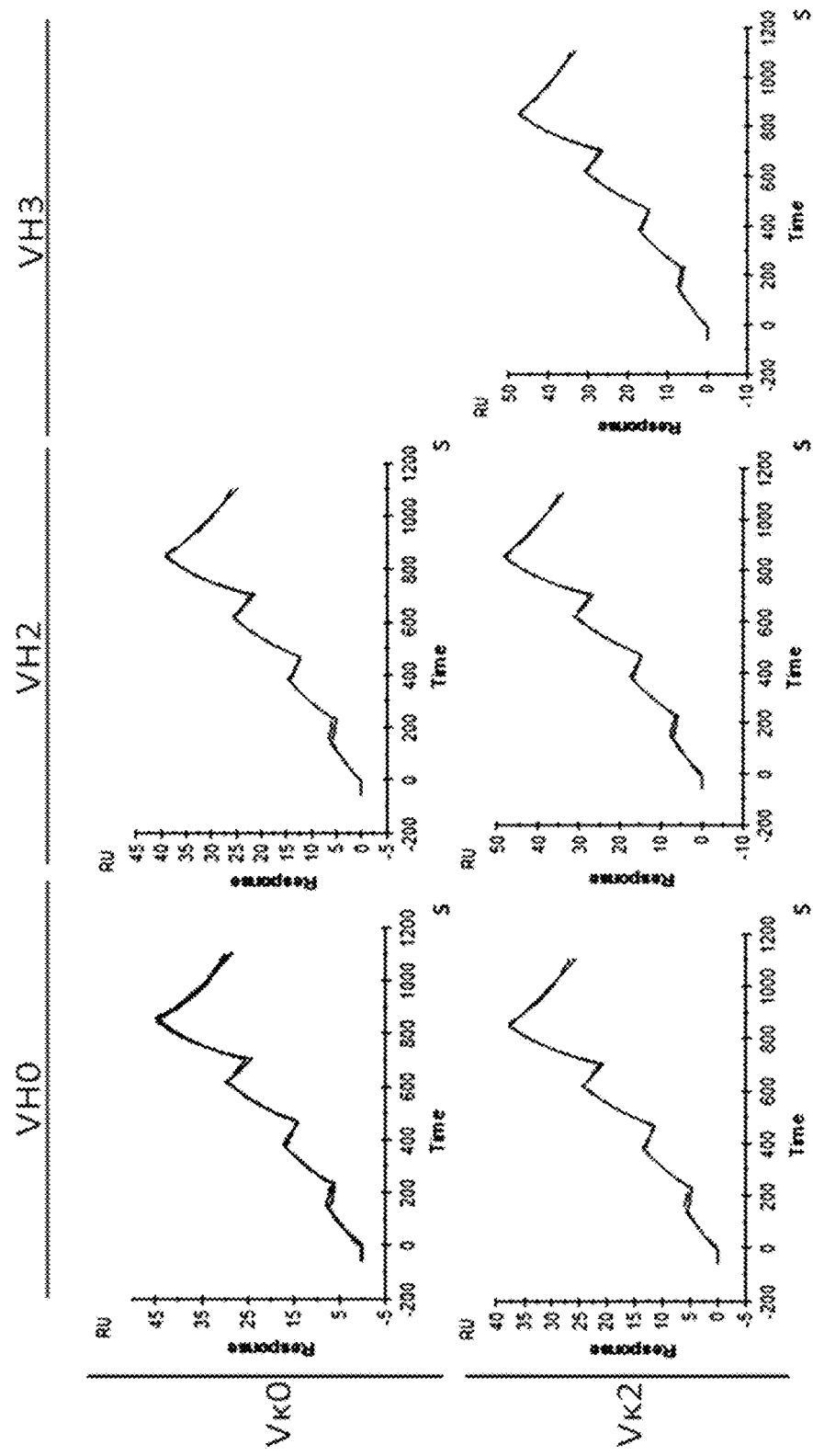
FIGS. 5a, 5b, 5c and 5d are sensorgrams showing binding affinity of the 21 candidate antibodies selected in the present disclosure for the antigen (c-Met).
Figure 5B:
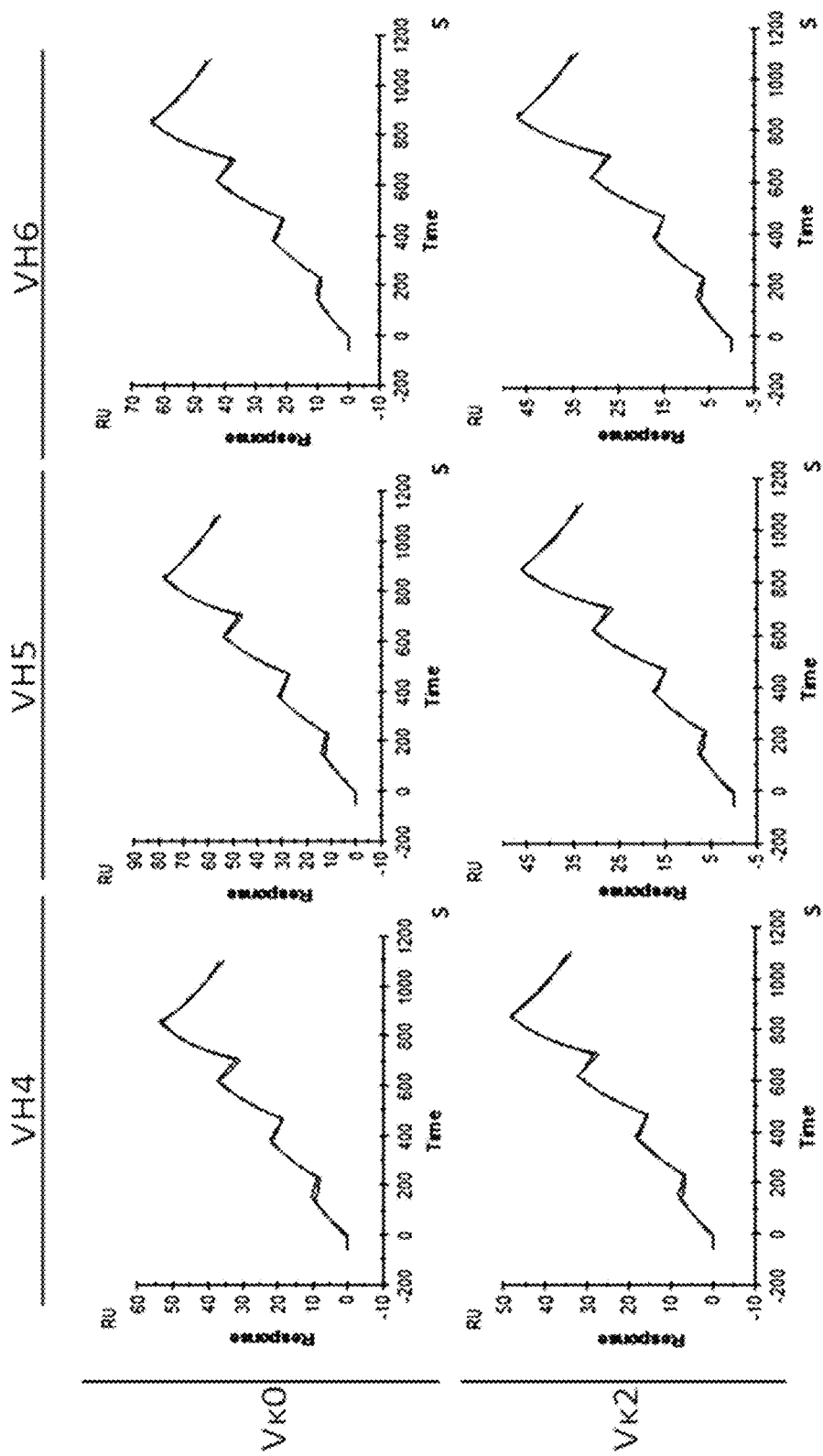
Figure 5C:
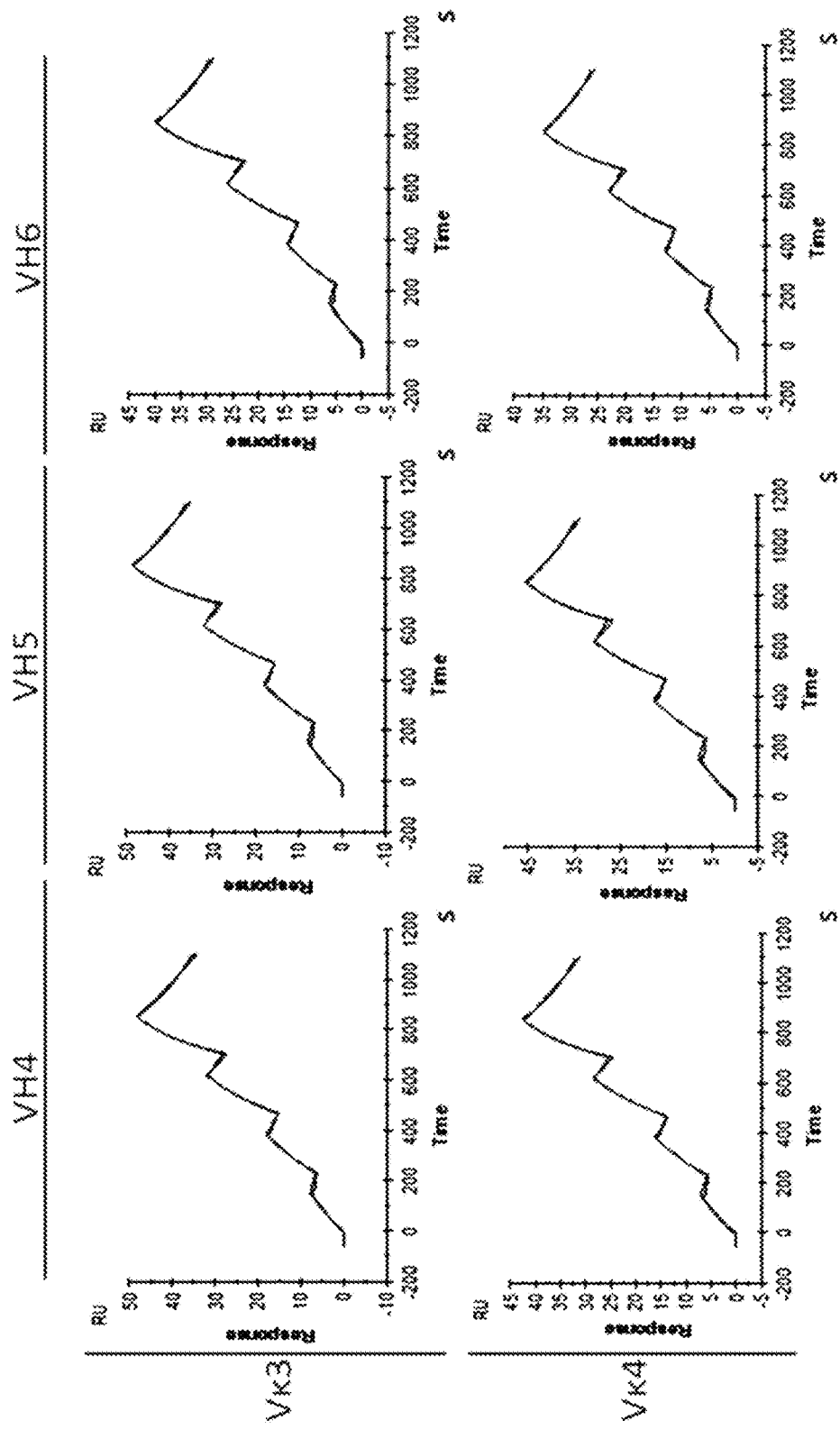
Figure 5D:
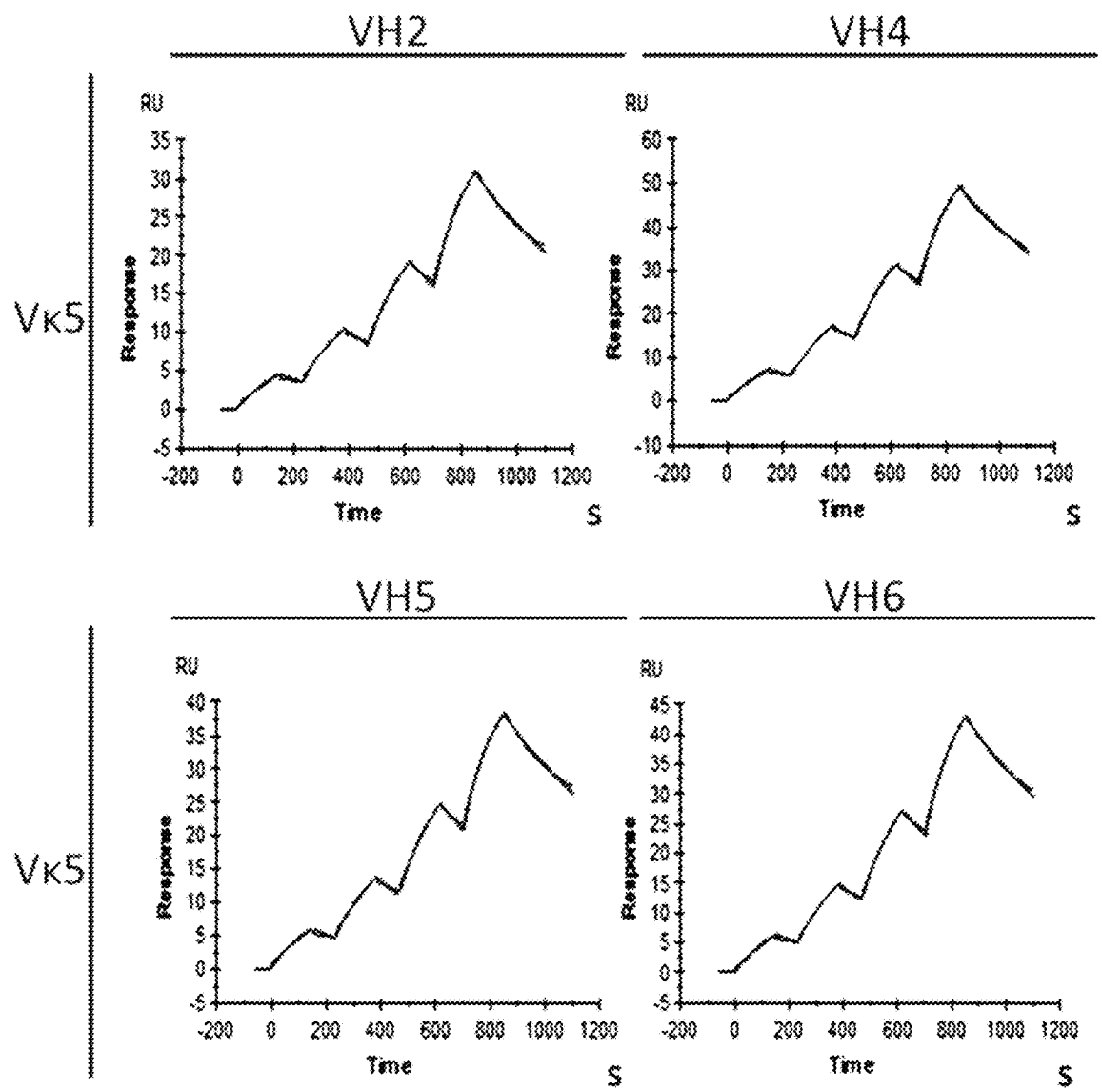

For additional analysis, antibodies were isolated from the cell supernatants, using Protein A sepharose columns (GE Healthcare, Little Chalfont, UK) according to the manufacturer's protocol. Dialysis against 1× PBS pH 7.2 gave a total of 21 final candidate antibodies isolated. Parts (1 µg) of the purified antibodies were reduced, electrophoresed on 4-12% bis-Tris SDS-PAGE gel (ThermoFisher, Loughborough, UK), stained with InstantBlue™ (Expedeon, Swavesey, UK) to analyze molecular weights. Experiment results are shown in FIG. 4. As can be seen in FIG. 4, the 21 candidate antibodies selected above were expressed well in human-derived cells.

Example 5: Binding Affinity of Candidate Antibody for Antigen (c-Met)

The candidate antibodies selected in Example 4 were measured for binding affinity for the antigen (c-Met) with the aid of Biacore™. The binding affinity of a total of 21 candidate antibodies for the antigen c-Met was measured in terms of dissociation constant ($K_D$ value) using Biacore™ T200 (serial no. 1909913), Biacore™ T200 Control Software V2.0.1, and Biacore™ T200 Evaluation Software V3.0 (GE Healthcare, Uppsala, Sweden). The anti-c-Met antibodies to be analyzed were immobilized on Protein A CM5 chips (GE Healthcare, Little Chalfont, UK) through which human c-Met antibody (Sino Biological, Beijing, China) with various concentrations ranging 0.15 to 2 nM was allowed to pass, thereby acquiring sensorgrams. On the basis of the acquired sensorgrams, association constants $k_{on}$ and dissociation constants $k_{off}$ were measured to calculate $K_D$ value, the ratio $k_{off}/k_{on}$. The results are given in FIG. 5 and Table 4. FIG. 5 shows single cycle kinetics sensorgrams of 21 candidate antibodies according to the present disclosure, and the binding affinities of the 21 antibodies are listed in a descending order in Table 4, below.

The data of Table 4 and FIG. 5 indicate that 20 candidate antibodies of the present disclosure vary in binding affinity within twice that of the modified antibody (VH0/Vk0) having the same variable domain as in the conventional antibody 1E4. In addition, all the 21 candidate antibodies were measured to have high binding affinity of as high as picomolar levels (pM, $K_D$ value: $10^{-10}$-$10^{-2}$).

TABLE 4

Binding affinities of candidate antibodies

| No. | Ligand | $K_D$ (M) | Relative $K_D$ to VMDO2 VH0/Vk0 | $R_{max}$ | Chi$^2$ (RU$^2$) |
|---|---|---|---|---|---|
| 1 | VH5/Vk4 | 3.49 × 10$^{-10}$ | 0.67 | 62.4 | 0.141 |
| 2 | VH5/Vk0 | 3.52 × 10$^{-10}$ | 0.68 | 102.8 | 0.515 |
| 3 | VH4/Vk4 | 3.72 × 10$^{-10}$ | 0.72 | 59.2 | 0.100 |
| 4 | VH6/Vk4 | 3.91 × 10$^{-10}$ | 0.75 | 49.4 | 0.0612 |
| 5 | VH4/Vk0 | 3.95 × 10$^{-10}$ | 0.76 | 70.5 | 0.354 |
| 6 | VH5/Vk3 | 4.02 × 10$^{-10}$ | 0.77 | 68.8 | 0.117 |
| 7 | VH6/Vk0 | 4.14 × 10$^{-10}$ | 0.80 | 89.0 | 0.249 |
| 8 | VH5/Vk2 | 4.20 × 10$^{-10}$ | 0.81 | 65.9 | 0.152 |
| 9 | VH4/Vk3 | 4.22 × 10$^{-10}$ | 0.81 | 68.9 | 0.119 |
| 10 | VH4/Vk2 | 4.23 × 10$^{-10}$ | 0.81 | 68.1 | 0.177 |
| 11 | VH6/Vk3 | 4.31 × 10$^{-10}$ | 0.83 | 58.0 | 0.0775 |
| 12 | VH6/Vk2 | 4.40 × 10$^{-10}$ | 0.85 | 69.6 | 0.133 |
| 13 | VH3/Vk2 | 4.77 × 10$^{-10}$ | 0.92 | 71.2 | 0.120 |
| 14 | VH2/Vk2 | 5.02 × 10$^{-10}$ | 0.97 | 73.9 | 0.156 |
| 15 | VH5/Vk5 | 5.06 × 10$^{-10}$ | 0.97 | 57.8 | 0.122 |
| 16 | VH0/Vk2 | 5.12 × 10$^{-10}$ | 0.98 | 57.1 | 0.115 |
| 17 | VH0/Vk0 | 5.20 × 10$^{-10}$ | 1.00 | 64.7 | 0.262 |
| 18 | VH4/Vk5 | 5.26 × 10$^{-10}$ | 1.01 | 76.1 | 0.158 |
| 19 | VH2/Vk0 | 5.34 × 10$^{-10}$ | 1.03 | 57.5 | 0.128 |
| 20 | VH6/Vk5 | 5.57 × 10$^{-10}$ | 1.07 | 68.3 | 0.105 |
| 21 | VH2/Vk5 | 6.85 × 10$^{-10}$ | 1.32 | 52.8 | 0.076 |

Example 6: Assay for Thermal Stability of Candidate Antibodies

In order to evaluate thermal stability of the candidate antibodies, SYPRO® Orange (ThermoFisher, Loughborough, UK) was used. While the temperature was increased over 56 min from 25° C. to 99° C. using StepOnePlus™ real-time PCR system (ThermoFisher, Loughborough, UK), the antibodies were analyzed for their misfolding points. Melting curves were drawn using Protein Thermal Shift Software version 1.2 (ThermoFisher, Loughborough, UK). The results are summarized in Table 5, below.

As is understood from data of Table 5, the thermal stability of the antibodies was affected mainly by the heavy chain domain and decreased in the order of VH6>VH4>VH5>VH0>>VH2>VH3. In addition, the five candidate antibodies, each including VH6, and the candidate antibodies VH4/Vk0 and VH5/Vk0 were observed to increase in thermal stability, compared to the reference antibody VH0/Vk0, on the basis of the melting temperature ($T_m 1$) at which the Fab (fragment antigen binding) structure is misfolded.

TABLE 5

Assay result for thermal stability of candidate antibodies

| No. | Antibody | Average $T_m 1$(° C.) | Average $T_m 2$(° C.) |
|---|---|---|---|
| 1 | VH6/Vk0 | 65.4 | * |
| 2 | VH6/Vk5 | 63.5 | * |
| 3 | VH6/Vk2 | 63.2 | * |
| 4 | VH6/Vk3 | 63.0 | * |
| 5 | VH5/Vk0 | 62.6 | ~68 |
| 6 | VH4/Vk0 | 62.6 | ~68 |
| 7 | VH6/Vk4 | 62.4 | * |
| 8 | VH0/Vk0 | 60.0 | 67.7 |
| 9 | VH5/Vk2 | 59.7 | 67.3 |
| 10 | VH4/Vk2 | 59.6 | 67.3 |
| 11 | VH5/Vk5 | 59.3 | 67.5 |
| 12 | VH2/Vk0 | 59.1 | 68.1 |
| 13 | VH4/Vk5 | 58.7 | 67.5 |
| 14 | VH5/Vk3 | 58.4 | 67.3 |
| 15 | VH4/Vk3 | 58.0 | 67.3 |
| 16 | VH5/Vk4 | 58.0 | 66.2 |
| 17 | VH0/Vk2 | 58.0 | 67.5 |
| 18 | VH2/Vk5 | 57.6 | 67.3 |
| 19 | VH2/Vk2 | 57.6 | 67.5 |
| 20 | VH4/Vk4 | 57.5 | 67.2 |
| 21 | VH3/Vk2 | 48.9 | 67.9 |

Example 7: Assay for Biopotency of Candidate Antibodies

HUVEC migration assay was performed in order to infer biopotency of the candidate antibodies. In HUVEC migration assay, HUVEC (Human umbilical vein endothelial cell) migrated when c-Met protein receptors on the cells were activated by a ligand such as HGF. The higher is the assay result % migration, the better the HUVEC migrates. Like HGF, the anti-c-Met antibody is expected to cause cell migration because it activates the antigen c-Met by phosphorylation. In a transwell (Corning Inc., USA) coated with 1% gelatin (Sigma Aldrich, USA), HUVEC (Lonza, USA) was incubated at a density of $2 \times 10^4$ cells/well in an upper chamber containing medium 199 (Gibco™, USA) supplemented 10% fetal bovine serum (Gibco™, New Zealand) and in a lower chamber containing Medium 199 (Gibco™, USA) supplemented with 1% fetal bovine serum at 37° C. under a 5% $CO_2$ condition. After incubation for 50 min, recombinant human hepatocyte growth factor (rhHGF) (R&D systems, USA) and each of the candidate antibodies were applied at a concentration of 50 ng/ml and 90 ng/ml, respectively, to the lower chamber. After 2 hours of incubation at 37° C. in 5% $CO_2$ atmosphere, the cells were fixed with 3.7% formaldehyde (VWR Life Science™, USA), dyed with crystal violet (VWR Life Science™, USA), and observed and photographed under a microscope to quantitate the distances by which the cells migrated from the inside to the outside. The results are depicted in FIG. 6.

Figure 6:
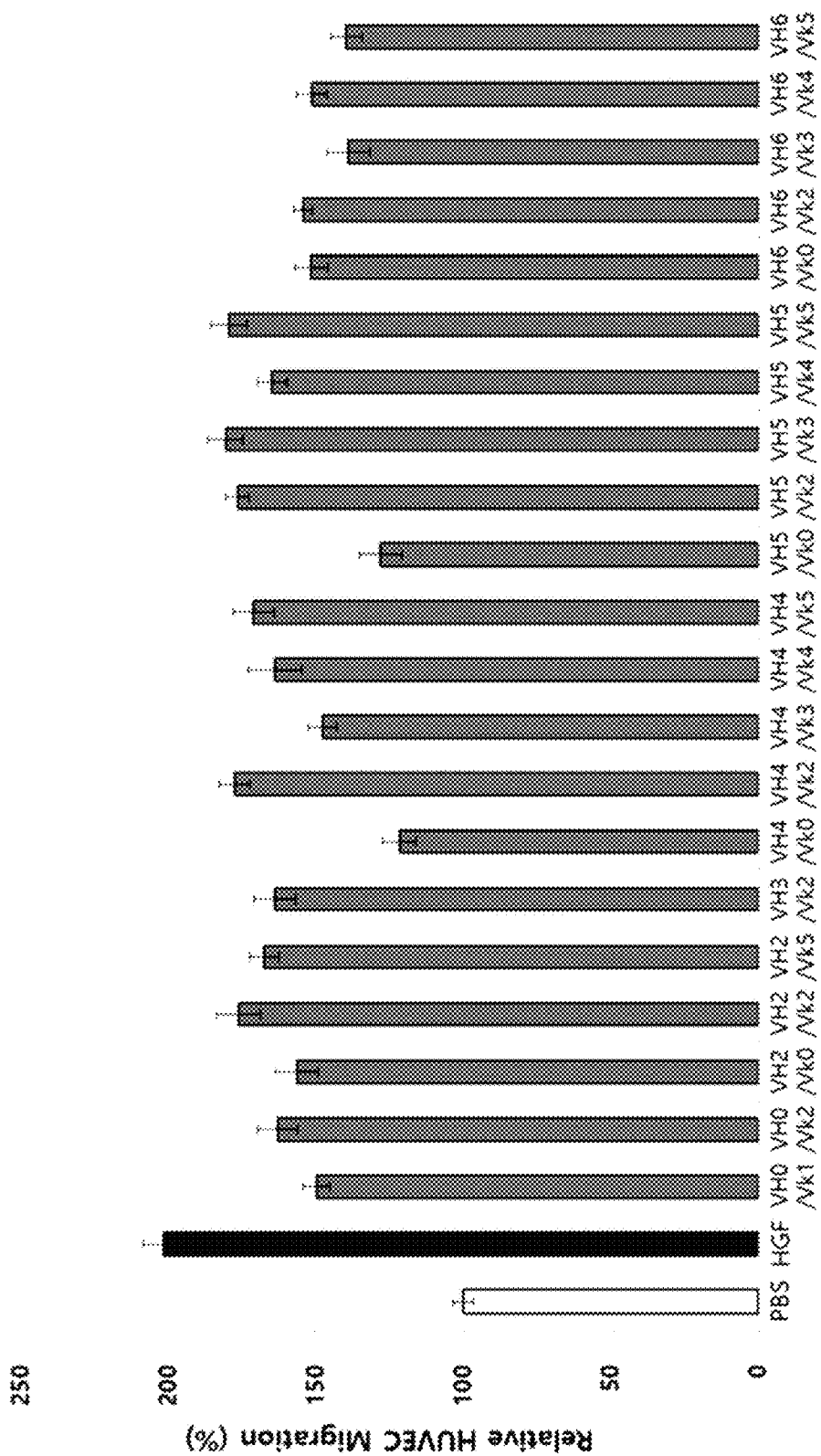
FIG. 6 is a graph showing the effect of the 21 candidate antibodies selected in the present disclosure on HUVEC migration to compare biopotency therebetween.

As a result, the 21 candidate antibodies were observed to promote cell migration, like the positive control recombinant human HGF (rhHFG), by about 120-179% compared to the negative control (FIG. 6). From the results, it is understood that the candidate antibodies of the present disclosure have excellent biopotency.

Example 8: Data Comparison and Analysis for Selecting Final Candidate Antibody

In order to select a final candidate group from the 21 candidate antibodies selected in Example 4, comparison was made according to criteria specified into expression level, binding affinity for antigen, thermal stability, and biopotency. As a rule, the expression level is considered to be the most important index when time and cost are taken into consideration from a point of view of production. Hence, the candidate antibodies with an expression level less than 15 μg/ml were excluded in primary consideration of smooth antibody production. Thereafter, degrees of improvement in each of the remaining candidate antibodies compared to the reference antibody (VH0/Vk0) were digitized with regard to the selected indices. For normalization, analysis index measurements for individual candidate antibodies were divided by average values to give ratios (index 1) which were in turn divided by the measurement for the antibody VH0/Vk0 (index 2) (Tables 6 to 9). In addition, the measurements for the four indices were multiplied for comprehensive comparison of the four indices of the candidate antibodies. The final results (index 3) are listed in a descending order in Table 10. With reference to the data, selection was made of four candidate antibodies VH4/Vk2, VH5/Vk2, VH6/Vk2, and VH6/Vk0, which are improved compared to the reference prototype (VH0/Vk0) (Table 10).

TABLE 6

Antibody Expression Level

| Antibody | Expression Level (μg/ml) | Index 1 | Index 2 |
|---|---|---|---|
| VH0/Vk0 | 37.1 | 1.213 | 1.000 |
| VH0/Vk2 | 32.4 | 1.059 | 0.873 |
| VH2/Vk0 | 31.9 | 1.043 | 0.860 |
| VH2/Vk2 | 21.2 | 0.693 | 0.571 |
| VH3/Vk2 | 17.2 | 0.562 | 0.464 |
| VH4/Vk0 | 22.4 | 0.732 | 0.604 |
| VH4/Vk2 | 49.7 | 1.625 | 1.340 |

TABLE 6-continued

Antibody Expression Level

| Antibody | Expression Level (μg/ml) | Index 1 | Index 2 |
|---|---|---|---|
| VH4/Vk5 | 16.5 | 0.539 | 0.445 |
| VH5/Vk0 | 21.6 | 0.706 | 0.582 |
| VH5/Vk2 | 46.4 | 1.517 | 1.251 |
| VH6/Vk0 | 30.2 | 0.987 | 0.814 |
| VH6/Vk2 | 40.5 | 1.324 | 1.092 |
| Average | 30.6 | — | — |

TABLE 7

Binding Affinity for Antigen

| Antibody | $K_D$ ($10^{-10}$ M) * | Index 1 | Index 2 |
|---|---|---|---|
| VH0/Vk0 | 5.20 | 0.677 | 1.000 |
| VH0/Vk2 | 5.12 | 0.688 | 1.016 |
| VH2/Vk0 | 5.34 | 0.659 | 0.974 |
| VH2/Vk2 | 5.02 | 0.701 | 1.036 |
| VH3/Vk2 | 4.77 | 0.738 | 1.090 |
| VH4/Vk0 | 3.95 | 0.891 | 1.316 |
| VH4/Vk2 | 4.23 | 0.832 | 1.229 |
| VH4/Vk5 | 5.26 | 0.669 | 0.989 |
| VH5/Vk0 | 3.52 | 1.000 | 1.477 |
| VH5/Vk2 | 4.20 | 0.838 | 1.238 |
| VH6/Vk0 | 4.14 | 0.850 | 1.256 |
| VH6/Vk2 | 4.40 | 0.800 | 1.182 |
| Average | 3.52 | — | — |

* inverse number because smaller $K_D$ values account for higher binding affinity.

TABLE 8

Thermal Stability

| Antibody | $T_m1$ (° C.) | Index 1 | Index 2 |
|---|---|---|---|
| VH0/Vk0 | 60 | 1.006 | 1.000 |
| VH0/Vk2 | 58 | 0.973 | 0.967 |
| VH2/Vk0 | 59.1 | 0.991 | 0.985 |
| VH2/Vk2 | 57.6 | 0.966 | 0.960 |
| VH3/Vk2 | 48.9 | 0.820 | 0.815 |
| VH4/Vk0 | 62.6 | 1.050 | 1.043 |
| VH4/Vk2 | 59.6 | 1.000 | 0.993 |
| VH4/Vk5 | 58.7 | 0.985 | 0.978 |
| VH5/Vk0 | 62.6 | 1.050 | 1.043 |
| VH5/Vk2 | 59.7 | 1.001 | 0.995 |
| VH6/Vk0 | 65.4 | 1.097 | 1.090 |
| VH6/Vk2 | 63.2 | 1.060 | 1.053 |
| Average | 59.6 | — | — |

TABLE 9

Biopotency

| Antibody | Relative Migration (%) | Index 1 | Index 2 |
|---|---|---|---|
| VH0/Vk0 | 149.8 | 0.951 | 1.000 |
| VH0/Vk2 | 162.8 | 1.034 | 1.087 |
| VH2/Vk0 | 156.4 | 0.993 | 1.044 |
| VH2/Vk2 | 176.1 | 1.118 | 1.176 |
| VH3/Vk2 | 163.9 | 1.041 | 1.095 |
| VH4/Vk0 | 121.7 | 0.773 | 0.812 |
| VH4/Vk2 | 177.4 | 1.127 | 1.185 |
| VH4/Vk5 | 171.0 | 1.086 | 1.142 |
| VH5/Vk0 | 128.1 | 0.813 | 0.855 |
| VH5/Vk2 | 176.5 | 1.121 | 1.179 |
| VH6/Vk0 | 151.5 | 0.962 | 1.012 |
| VH6/Vk2 | 154.2 | 0.979 | 1.030 |
| Average | 157.5 | — | — |

TABLE 10

Final Results of candidate antibodies according to 4 selection criteria (index 3)

| Antibody | Index 3 |
| --- | --- |
| VH4/Vk2 | 1.938 |
| VH5/Vk2 | 1.816 |
| VH6/Vk2 | 1.399 |
| VH6/Vk0 | 1.128 |
| VH0/Vk0 | 1.000 |
| VH0/Vk2 | 0.932 |
| VH2/Vk0 | 0.861 |
| VH5/Vk0 | 0.767 |
| VH4/Vk0 | 0.674 |
| VH2/Vk2 | 0.668 |
| VH4/Vk5 | 0.491 |
| VH3/Vk2 | 0.451 |

Although the present invention has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An anti-c-Met antibody or an antigen-binding fragment comprising:

(a) an immunoglobulin heavy chain variable domain comprising the structure of FRH1-CDRH1-FRH2-CDRH2-FRH3-CDRH3-FRH4; and (b) an immunoglobulin light chain variable domain comprising the structure of FRL1-CDRL1-FRL2-CDRL2-FRL3-CDRL3-FRL4:

wherein the CDRH1, the CDRH2, and the CDRH3 comprise the amino acid sequences of SEQ ID NOS: 1, 2, and 3, respectively, and the CDRL1, CDRL2, and CDRL3 comprise the amino acid sequences of SEQ ID NOS: 4, 5, and 6, respectively, wherein (a) and (b) are selected from the following group:

i) immunoglobulin heavy chain variable domain comprising an amino acid sequence of SEQ ID NO: 11 and immunoglobulin light chain variable domain comprising an amino acid sequence of SEQ ID NO: 18;

ii) immunoglobulin heavy chain variable domain comprising an amino acid sequence of SEQ ID NO: 12 and immunoglobulin light chain variable domain comprising an amino acid sequence of SEQ ID NO: 17;

iii) immunoglobulin heavy chain variable domain comprising an amino acid sequence of SEQ ID NO: 12 and immunoglobulin light chain variable domain comprising an amino acid sequence of SEQ ID NO: 18;

iv) immunoglobulin heavy chain variable domain comprising an amino acid sequence of SEQ ID NO: 14 and immunoglobulin light chain variable domain comprising an amino acid sequence of SEQ ID NO: 17;

v) immunoglobulin heavy chain variable domain comprising an amino acid sequence of SEQ ID NO: 14 and immunoglobulin light chain variable domain comprising an amino acid sequence of SEQ ID NO: 18 vi) immunoglobulin heavy chain variable domain comprising an amino acid sequence of SEQ ID NO: 14 and immunoglobulin light chain variable domain comprising an amino acid sequence of SEQ ID NO: 21;

vii) immunoglobulin heavy chain variable domain comprising an amino acid sequence of SEQ ID NO: 15 and immunoglobulin light chain variable domain comprising an amino acid sequence of SEQ ID NO: 17;

viii) immunoglobulin heavy chain variable domain comprising an amino acid sequence of SEQ ID NO: 15 and immunoglobulin light chain variable domain comprising an amino acid sequence of SEQ ID NO: 18;

ix) immunoglobulin heavy chain variable domain comprising an amino acid sequence of SEQ ID NO: 16 and immunoglobulin light chain variable domain comprising an amino acid sequence of SEQ ID NO: 17; and x) immunoglobulin heavy chain variable domain comprising an amino acid sequence of SEQ ID NO: 16 and immunoglobulin light chain variable domain comprising an amino acid sequence of SEQ ID NO: 18.

2. The anti-c-Met antibody or antigen-binding fragment of claim 1, comprising i) immunoglobulin heavy chain comprising an amino acid sequence of SEQ ID NO: 34 and immunoglobulin light chain comprising an amino acid sequence of SEQ ID NO: 42;

ii) immunoglobulin heavy chain comprising an amino acid sequence of SEQ ID NO: 35 and immunoglobulin light chain comprising an amino acid sequence of SEQ ID NO: 41;

iii) immunoglobulin heavy chain comprising an amino acid sequence of SEQ ID NO: 35 and immunoglobulin light chain comprising an amino acid sequence of SEQ ID NO: 42;

iv) immunoglobulin heavy chain comprising an amino acid sequence of SEQ ID NO: 37 and immunoglobulin light chain comprising an amino acid sequence of SEQ ID NO: 41;

v) immunoglobulin heavy chain comprising an amino acid sequence of SEQ ID NO: 37 and immunoglobulin light chain comprising an amino acid sequence of SEQ ID NO: 42;

vi) immunoglobulin heavy chain comprising an amino acid sequence of SEQ ID NO: 37 and immunoglobulin light chain comprising an amino acid sequence of SEQ ID NO: 45;

vii) immunoglobulin heavy chain comprising an amino acid sequence of SEQ ID NO: 38 and immunoglobulin light chain comprising an amino acid sequence of SEQ ID NO: 41;

viii) immunoglobulin heavy chain comprising an amino acid sequence of SEQ ID NO: 38 and immunoglobulin light chain comprising an amino acid sequence of SEQ ID NO: 42;

ix) immunoglobulin heavy chain comprising an amino acid sequence of SEQ ID NO: 39 and immunoglobulin light chain comprising an amino acid sequence of SEQ ID NO: 41 and x) immunoglobulin heavy chain comprising an amino acid sequence of SEQ ID NO: 39 and immunoglobulin light chain comprising an amino acid sequence of SEQ ID NO: 42.

3. The anti-c-Met antibody or antigen-binding fragment of claim 1, wherein the antigen-binding fragment is Fab, Fab', F(ab')$_2$, Fv, scFv or chemically linked F(ab')$_2$.

4. An anti-c-Met antibody or antigen-binding fragment, comprising:

(a) a heavy chain variable domain comprising CDRH1 (complementarity determining region 1 of heavy chain) of SEQ ID NO: 1, CDRH2 of SEQ ID NO: 2, and CDRH3 of SEQ ID NO: 3;

(b) an immunoglobulin heavy chain constant domain comprising CH1 (constant domain 1 of heavy chain) of SEQ ID NO: 7;

(c) an immunoglobulin light chain variable domain comprising CDRL1 (complementarity determining region 1 of light chain) of SEQ ID NO: 4, CDRL2 of SEQ ID NO: 5, and CDRL3 of SEQ ID NO: 6; and (d) an immunoglobulin light chain constant domain comprising Ck (kappa-constant domain) of SEQ ID NO: 8, wherein at least one of the amino acid residue at position 97 in CH1 of SEQ ID NO: 7 and the amino acid residue at position 2 in Ck of SEQ ID NO: 8 is mutated by substitution with arginine or threonine, wherein (a) and (b) are selected from the following group:

i) immunoglobulin heavy chain variable domain comprising an amino acid sequence of SEQ ID NO: 11 and immunoglobulin light chain variable domain comprising an amino acid sequence of SEQ ID NO: 18;

ii) immunoglobulin heavy chain variable domain comprising an amino acid sequence of SEQ ID NO: 12 and immunoglobulin light chain variable domain comprising an amino acid sequence of SEQ ID NO: 17;

iii) immunoglobulin heavy chain variable domain comprising an amino acid sequence of SEQ ID NO: 12 and immunoglobulin light chain variable domain comprising an amino acid sequence of SEQ ID NO: 18;

iv) immunoglobulin heavy chain variable domain comprising an amino acid sequence of SEQ ID NO: 14 and immunoglobulin light chain variable domain comprising an amino acid sequence of SEQ ID NO: 17;

v) immunoglobulin heavy chain variable domain comprising an amino acid sequence of SEQ ID NO: 14 and immunoglobulin light chain variable domain comprising an amino acid sequence of SEQ ID NO: 18 vi) immunoglobulin heavy chain variable domain comprising an amino acid sequence of SEQ ID NO: 14 and immunoglobulin light chain variable domain comprising an amino acid sequence of SEQ ID NO: 21;

vii) immunoglobulin heavy chain variable domain comprising an amino acid sequence of SEQ ID NO: 15 and immunoglobulin light chain variable domain comprising an amino acid sequence of SEQ ID NO: 17;

viii) immunoglobulin heavy chain variable domain comprising an amino acid sequence of SEQ ID NO: 15 and immunoglobulin light chain variable domain comprising an amino acid sequence of SEQ ID NO: 18;

ix) immunoglobulin heavy chain variable domain comprising an amino acid sequence of SEQ ID NO: 16 and immunoglobulin light chain variable domain comprising an amino acid sequence of SEQ ID NO: 17; and x) immunoglobulin heavy chain variable domain comprising an amino acid sequence of SEQ ID NO: 16 and immunoglobulin light chain variable domain comprising an amino acid sequence of SEQ ID NO: 18.

5. The anti-c-Met antibody or antigen-binding fragment of claim 4, wherein the amino acid residue at position 97 in CH1 of SEQ ID NO: 7 and the amino acid residue at position 2 in Ck of SEQ ID NO: 8 are mutated by substitution with arginine and threonine, respectively.

* * * * *